(12) United States Patent
Chauhan et al.

(10) Patent No.: US 11,033,457 B2
(45) Date of Patent: Jun. 15, 2021

(54) PRESERVATIVE REMOVAL FROM EYE DROPS CONTAINING HYDROPHILIC DRUGS

(71) Applicant: University of Florida Research Foundation, Inc., Gainesville, FL (US)

(72) Inventors: Anuj Chauhan, Golden, CO (US); Phillip J. Dixon, Gainesville, FL (US); Poorvajan Sekar, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1 day.

(21) Appl. No.: 16/388,470

(22) Filed: Apr. 18, 2019

(65) Prior Publication Data

US 2019/0269575 A1    Sep. 5, 2019

Related U.S. Application Data

(63) Continuation of application No. PCT/US2018/052477, filed on Sep. 24, 2018.

(60) Provisional application No. 62/562,702, filed on Sep. 25, 2017.

(51) Int. Cl.

| | | |
|---|---|---|
| *A61J 1/14* | (2006.01) | |
| *B01J 20/26* | (2006.01) | |
| *B01J 20/28* | (2006.01) | |
| *A61K 9/00* | (2006.01) | |
| *A61K 9/08* | (2006.01) | |
| *A61K 31/498* | (2006.01) | |
| *A61K 31/5377* | (2006.01) | |
| *A61K 47/18* | (2017.01) | |
| *B01D 15/00* | (2006.01) | |

(52) U.S. Cl.
CPC .......... *A61J 1/1468* (2015.05); *A61J 1/1443* (2013.01); *A61J 1/1475* (2013.01); *B01J 20/261* (2013.01); *B01J 20/267* (2013.01); *B01J 20/28016* (2013.01); *B01J 20/28042* (2013.01); *A61J 1/1456* (2015.05); *A61K 9/0048* (2013.01); *A61K 9/08* (2013.01); *A61K 31/498* (2013.01); *A61K 31/5377* (2013.01); *A61K 47/186* (2013.01); *B01D 15/00* (2013.01)

(58) Field of Classification Search
None
See application file for complete search history.

(56) References Cited

U.S. PATENT DOCUMENTS

| | | | |
|---|---|---|---|
| 5,080,800 A | 1/1992 | Heyl et al. | |
| 2003/0199507 A1* | 10/2003 | Chang | A61K 31/498 514/235.8 |
| 2006/0093999 A1 | 5/2006 | Hei | |
| 2008/0269105 A1* | 10/2008 | Taft | A61K 9/0019 514/1.1 |
| 2015/0374633 A1 | 12/2015 | Fedorchak et al. | |
| 2017/0224531 A1* | 8/2017 | Chauhan | A61J 1/1456 |

FOREIGN PATENT DOCUMENTS

WO    WO-2009032266 A2 *   3/2009

OTHER PUBLICATIONS

International Search Report and Written Opinion, PCT/US2018/52477 (dated Dec. 20, 2018).

* cited by examiner

*Primary Examiner* — Robert A Wax
*Assistant Examiner* — Randeep Singh
(74) *Attorney, Agent, or Firm* — Marshall, Gerstein & Borun LLP

(57) ABSTRACT

A particulate plug for removing a preservative from a solution, suspension, or emulsion comprising a drug is presented. The plug comprises microparticles of a homopolymer comprising a hydrophilic repeating unit or of a copolymer comprising at least one hydrophilic repeating unit and at least one hydrophobic repeating unit. The microparticles are irregular-shaped rigid aggregates and are sized and packed to yield a hydraulic permeability greater than 0.01 Da. The homopolymers have absorbed portions of a preservative to be removed and/or a drug for delivery in solution, as can the copolymer.

22 Claims, 30 Drawing Sheets

PRESERVATIVE REMOVAL FROM EYE DROPS CONTAINING HYDROPHILIC DRUGS

CROSS-REFERENCE

This application is a continuation of International Patent Application No. PCT/US18/52477, filed Sep. 24, 2018, which claims the benefit of U.S. Provisional Application No. 62/562,702, filed Sep. 25, 2017, which applications are incorporated herein by reference.

BACKGROUND

Ophthalmic diseases are commonly treated with prescribed multi-dose medications packaged in eye drop bottles due to ease of use, availability, affordability, and patient compliance. The frequency of topical eye drop application varies from one or two times a day for diseases like glaucoma to as many as ten times a day for severe infections. Although eye drops formulations are packed under sterile conditions, the potential risk of contamination after prolonged use or improper handling can be a key factor contributing to ocular infections. In some cases, as a frugal measure, multiple patients tend to use the same multi-dose containers to administer medications, overlooking the possibility of ocular infections due to cross-contamination, particularly if the protocol for disinfecting the nozzle is not followed. Most ophthalmic formulations now contain an added preservative to maintain the shelf life of the sterile medication and eliminate microbial growth. The US Food and Drug Administration has imposed regulations on multi-dose ophthalmic formulations, mandating the addition of preservatives to providing microbe-free medication. A variety of preservatives are used to serve this purpose. Preservatives are needed for maintaining sterility, but the benefit is often offset by adverse side effects of the preservatives, even among healthy subjects.

Benzalkonium chloride (BAK), a quaternary ammonium compound with high efficacy, is used prominently. BAK is an active detergent disinfecting agent, which interrupts the lipid membranes of cells, thereby inhibiting the growth of microorganisms. Despite an acceptable tolerance and safety profile of BAK, many studies have shown commercial topical medications with added BAK content to induce severe toxic side effects. Well-documented adverse effects of BAK include tear film instability, trabecular and corneal cells growth retardation and corneal and conjunctival inflammation. Cytotoxicity studies show that BAK disrupts ocular surface cells and tissues, whose impact in glaucoma and dry eye patients requiring long-term and frequent dosing is deleterious. Corneal endothelial damage occurs upon prolonged use of topical medication with added benzalkonium chloride. High tear film instability and disruption of the corneal barrier is observed using the preserved glaucoma drug Timolol to a greater extent than when using preservative-free Timolol in healthy subjects. The detergent action of BAK solution disrupts superficial lipid layers of the tear film into oil droplets solubilized by a single drop of 0.01% BAK solution.

In 2009, the European Medicines Agency's Committee for Medicinal Products for Human Use concluded that unpreserved formulations "are needed for patients with lower tolerance to preservatives." and "for long-term treatment, formulations without preservatives are valuable alternatives." Considering the adverse effects of preservatives, the development of safe eye drop dispensing devices to deliver preservative-free formulations has been pursued for more than a decade. Preservative-free formulations are available in single-dose containers to eliminate the need for preservatives; however, these are not convenient and too expensive for wide public use.

U.S. Pat. No. 5,080,800 teaches a process for removing components from solutions, including preservatives from eye-drops. The process involves the use of ion exchange resins to selectively remove ocular preservatives. Ion exchange resins have not been tested extensively for biocompatibility and cytotoxicity and inherently are non-selective for molecules of same charge, adsorb ionic drugs as readily as any ionic preservative such as BAK. The hydraulic permeability of these resins is not addressed although this characteristic is critical for devices that allow formation of drops without excessive pressure. U.S. Pat. No. 5,080,800 does not teach on the importance of ensuring that the filters are designed to resist growth of microorganisms that may remain trapped. U.S. Pat. No. 5,080,800 does not teach on the necessary requirements to ensure that the concentration of the active drug in the drops coming out of the device do not fall below the minimum requirements based. Hence a practical way of retaining the beneficial behavior of preservatives while avoiding their toxic effects in the eye remains a need.

SUMMARY

Embodiments of the disclosure are directed to particulate plugs for selectively removing a large fraction of the preservative without significantly removing the drug and specifically directed to achieving this for each eluting drop. The material of the plug may be designed to minimize drug binding. The material of the plug may depend on the properties of the drug whose binding is to be minimized. The binding may depend on the structure of the drug and/or the detailed structure of the matrix materials of the particles of the tip. Broadly, ophthalmic drugs can be divided into hydrophobic and hydrophilic categories depending of the affinity of the drug for water. Hydrophilic drugs are more soluble in water while hydrophobic drugs are less soluble. By combining one or more different monomers into the formulation for making the particles, the material may selectively remove a preservative while minimizing binding of the drug.

Embodiments of the disclosure are directed to particulate plugs for removing a preservative from a drug solution where microparticles comprising the plug are a homopolymer comprising hydrophilic or hydrophobic repeating units or a copolymer comprising multiple hydrophilic or hydrophobic monomers, or a copolymer comprising at least one hydrophilic monomer and at least one hydrophobic monomer. In some embodiments, microparticles are made by polymerizing a mixture of monomers to achieve a high partitioning of the preservative BAK and low partitioning of drug. For hydrophilic drugs, according to an embodiment of the disclosure, the particulate plug can comprise a homopolymer comprising hydrophilic repeating units or a copolymer comprising at least one hydrophilic repeating unit and at least one hydrophobic repeating unit. The microparticles are irregular-shaped rigid aggregates that form a particulate plug having a hydraulic permeability greater than 0.01 Da and where the plug fits an outlet of a container for a solution, emulsion, or suspension. The homopolymers can further comprise absorbed portions of a preservative to be removed and/or a drug for delivery in solution, wherein the particulate plug rapidly and selectively removes a preservative from the solution, emulsion, or suspension. The copolymer can further comprise absorbed portions of a preservative to be removed and/or a drug for delivery in solution. The hydrophilic repeating units (i.e. monomers) may comprise hydroxyethyl methacrylate (HEMA) and/or dimethylacrylamide (DMA) and hydrophobic repeating units (i.e. monomers) may comprise t-butyl methacrylate and/or Methacryloxypropyltris(trimethylsiloxy)silane (TRIS) and/or t-amyl methacrylate and/or n-octyl methacrylate and/or iso-decyl methacrylate and/or n-decyl methacrylate and/or n-dodecyl acrylate and/or n-hexyl acrylate and/or n-dodectyl acrylate and/or N-(n-Octadecyl)acrylamide, and/or any other monomer.

The drug can be a hydrophilic drug, for example, Timolol Maleate, Levofloxacin, Dorzolamide, Brimonidine Tartrate, and/or hydrophobic drugs, for example, latanoprost or bimatoprost, and/or a combination of drugs, for example, Combigan. The preservative may be Benzalkonium chloride (BAK). For removal of BAK from formulations containing hydrophobic drugs, the plug can be formed from hydrophilic monomers to minimize the binding of the hydrophobic drugs such as latonoprost, bimatoprost, dexamethasone, cyclosporine, etc. The plug for example can be prepared from copolymers of hydroxyethyl methacrylate (HEMA) and methacrylic acid or from just methacrylic acid.

Another embodiment of the disclosure is directed to a method of removing a preservative from a drug solution, where a container has an extended outlet and a chamber for holding a drug solution comprising at least one drug and a preservative where the extended outlet is packed with a particulate plug and the drug solution is forced through the particulate plug. The particulate plug can be preloaded with the drug or with the preservative.

In an aspect, the present disclosure provides a particulate plug for removing a preservative from a solution comprising a drug. The plug may comprise microparticles of a homopolymer comprising hydrophilic repeating units or a copolymer comprising at least one hydrophilic repeating units and at least one hydrophobic repeating unit, wherein the microparticles are irregular-shaped rigid aggregates and form a particulate plug having a hydraulic permeability greater than 0.01 Da and fits an outlet of a container for a solution, emulsion, or suspension, wherein the homopolymers further comprises or the copolymer optionally further comprises absorbed portions of a preservative to be removed and/or a drug for delivery in solution, wherein the particulate plug rapidly and selectively removes a preservative from the solution, emulsion, or suspension.

In some embodiments, the hydrophilic repeating units comprise hydroxyethyl methacrylate (HEMA) and/or dimethylacrylamide (DMA). In some embodiments, the hydrophobic repeating units comprise t-butyl methacrylate and/or Methacryloxypropyltris(trimethylsiloxy)silane (TRIS). In some embodiments, the drug comprises Timolol Maleate; Levofloxacin; Dorzolamide; Brimonidine Tartrate; Combigan; or combinations thereof. In some embodiments, the preservative comprises Benzalkonium chloride (BAK). In some embodiments, the hydrophilic repeating units comprise HEMA. In some embodiments, the hydrophilic repeating units comprise HEMA and the hydrophobic repeating unit comprises t-butyl methacrylate. In some embodiments, the hydrophilic repeating units comprise HEMA and the hydrophobic repeating unit comprises t-butyl methacrylate and TRIS. In some embodiments, the hydrophilic repeating units comprise DMA and the hydrophobic repeating unit comprises TRIS. In some embodiments, the particulate plug comprises pHEMA with absorbed Timolol. In some embodiments, the particulate plug comprises pHEMA and t-butyl methacrylate with absorbed BAK.

In another aspect, the present disclosure provides a method of removing a preservative from a drug solution, suspension, or emulsion. The method may comprise providing a container having an extended outlet and a chamber for holding the drug solution, suspension, or emulsion comprising at least one drug and a preservative; the container comprising a particulate plug according to claim 1 within the extended outlet; and forcing the drug solution, suspension, or emulsion through the particulate plug.

In some embodiments, the method further comprises preloading the particulate plug with the drug and/or with the preservative. In some embodiments, the drug comprises Timolol Malcate, Levofloxacin, Dorzolamide, Brimonidine Tartrate, Combigan, or a combination thereof. In some embodiments, the preservative is Benzalkonium chloride (BAK). In some embodiments, the plug comprises HEMA and/or DMA. In some embodiments, the plug comprises t-butyl methacrylate and/or TRIS.

In another aspect, the present disclosure provides a device for delivery of a pharmaceutical formulation, the device comprising the particulate plug any embodiment and a pharmaceutical formulation comprising one or more active components and a preservative, wherein when the pharmaceutical formulation is forced through the particulate plug at least 90% of the preservative is selectively removed, while at least 90% of the one or more active components are retained in the delivered pharmaceutical formulation.

In some embodiments, the device is an eye drop bottle for dispensing drops of the pharmaceutical formulation and wherein the concentration of the one or more active components in a dispensed drop is at least 90% of that of the formulation inside the eye drop bottle, for every drop of the formulation forced through the plug. In some embodiments, the particulate plug comprises a packed bed of particles. In some embodiments, the device has a holder assembly to retain the particulate plug while forcing the formulation through the plug. In some embodiments, the particulate plug comprises a formulation entry face and a formulation exit face, and the holder assembly comprises filters on the solutions entry and exit faces of the particulate plug. In some embodiments, the holder assembly comprises a solution permeable bag around the particulate plug. In some embodiments, the particulate plug is sintered to fuse the particulate plug as a porous monolith. In some embodiments, the particulate plug has a partition coefficient for the preservative that is at least 100 and a partition coefficient for each active component that is less than 1. In some embodiments, the particulate plug is pre-equilibrated with the drug. In some embodiments, the device further comprises packaging that holds the device in a position for forcing the formulation through the particulate plug from manufacture until the device is received by a patient for use.

In another aspect, the present disclosure provides a preservative removing device. The preservative removing device may comprise microparticles of a homopolymer comprising hydrophilic repeating unit, wherein the microparticles are irregular-shaped rigid aggregates, wherein the microparticles form a particulate plug having a hydraulic permeability greater than 0.01 Da, wherein the plug fits an outlet of a container for a solution, emulsion, or suspension, wherein the homopolymer further comprises absorbed portions of a preservative to be removed and a therapeutic agent for delivery, and wherein the particulate plug rapidly and selectively removes a preservative from the solution, emulsion, or suspension.

In another aspect, the present disclosure provides a preservative removing device. The preservative removing device may comprise microparticles of a copolymer comprising a least one hydrophilic repeating unit and at least one hydrophobic repeating unit, wherein the microparticles are irregular-shaped rigid aggregates, wherein the microparticles form a particulate plug having a hydraulic permeability greater than 0.01 Da, wherein the plug fits an outlet of a container for a solution, emulsion, or suspension, wherein the co-polymer optionally comprises absorbed portions of a preservative to be removed and a therapeutic agent for delivery, and wherein the particulate plug rapidly and selectively removes the preservative from the solution, emulsion, or suspension.

In some embodiments, the device further comprises a cross-linker, wherein the cross-linker is a hydrophilic cross linker. In some embodiments, the hydrophilic cross-linker comprises SR9035, diethylene glycol dimethacrylate (DEGDMA), or ethylene glycol dimethacrylate (EDGMA). In some embodiments, the hydrophilic repeating unit comprises one or more of hydroxyethyl methacrylate (HEMA), methacrylic acid (MAA), N-vinyl-pyrrolidone (NVP), or dimethylacrylamide (DMA). In some embodiments, the at least one hydrophobic repeating unit comprises one or more of t-butyl methacrylate (TBM) or Methacryloxypropyltris (trimethylsiloxy)silane (TRIS). In some embodiments, the hydrophilic repeating unit comprises HEMA. In some embodiments, the hydrophilic repeating unit comprises NVP. In some embodiments, the hydrophilic repeating unit comprises MAA. In some embodiments, the hydrophilic repeating unit comprises DMA. In some embodiments, the hydrophilic repeating unit comprises HEMA and the at least one hydrophobic repeating unit comprises TBM. In some embodiments, the device comprises 5% to 25% HEMA and 75% to 95% TBM. In some embodiments, the hydrophilic repeating unit comprises MAA and the at least one hydrophobic repeating unit comprises TBM. In some embodiments, the device comprises 5% to 25% MAA and 75% to 95% TBM. In some embodiments, the hydrophilic repeating unit comprises HEMA and the at least one hydrophobic repeating unit comprises TRIS. In some embodiments, the device comprises 5% to 50% HEMA and 50% to 95% TRIS. In some embodiments, the hydrophilic repeating unit comprises DMA and the at least one hydrophobic repeating unit comprises TRIS. In some embodiments, the device comprises 5% to 25% DMA and 75% to 95% TRIS.

In some embodiments, the device further comprises a cross-linker, wherein the cross-linker is a hydrophilic cross linker. In some embodiments, the hydrophilic cross-linker comprises SR9035, diethylene glycol dimethacrylate (DEGDMA), or ethylene glycol dimethacrylate (EDGMA). In some embodiments, the irregular-shaped rigid aggregates are rough edged particles and the rough edged particles comprise a diameter less than 250 microns. In some embodiments, the rough edged particles comprise a diameter less than 150 microns. In some embodiments, the preservative comprises Benzalkonium chloride. In some embodiments, the preservative is SofZia or Purite. In some embodiments, the therapeutic agent comprises at least one of Timolol Maleate, Levofloxacin, Dorzolamide, Brimonidine Tartrate, Bimatoprost, Tetrahydrozolin, or Olopatadine. In some embodiments, the therapeutic agent comprises Timolol Maleate and Brimonidine Tartrate. In some embodiments, the therapeutic agent comprises Timolol Maleate.

In another aspect, the present disclosure provides a method of removing a preservative from a drug solution, suspension, or emulsion, according to any embodiment. The method may comprise providing a container having an extended outlet and a chamber for holding the drug solution, suspension, or emulsion, the drug solution, suspension, or emulsion comprising at least one drug and a preservative; wherein the container comprises a particulate plug for removing the preservative from the solution, suspension, or emulsion, the particulate plug provided within the extended outlet; and forcing the drug solution, suspension, or emulsion through the particulate plug. In some embodiments, the method further comprises preloading the particulate plug with the drug or with the preservative.

In another aspect, the present disclosure provides a device for delivery of a pharmaceutical formulation, comprising the particulate plug of any embodiment and a pharmaceutical formulation comprising one or more active components and a preservative, wherein when the pharmaceutical formulation is forced through the particulate plug at least 90% of the preservative is selectively removed while at least 90% of all active components are retained in the delivered pharmaceutical formulation.

In some embodiments, the device is an eye drop bottle for dispensing drops of the pharmaceutical formulation, wherein the concentration of the active components in a dispensed drop is at least 90% of that of the formulation inside the eye drop bottle for every drop of the solution forced through the plug. In some embodiments, the device has a holder assembly to retain the particulate plug while forcing the solution through the particulate plug. In some embodiments, the particulate plug comprises a formulation entry face and a formulation exit face, and the holder assembly comprises filters on the entry and exit faces of the particulate plug. In some embodiments, the device further comprises packaging that holds the device in a position for forcing the solution, suspension, or emulsion through the particulate plug from manufacture until the device is received by a patient for use.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1:
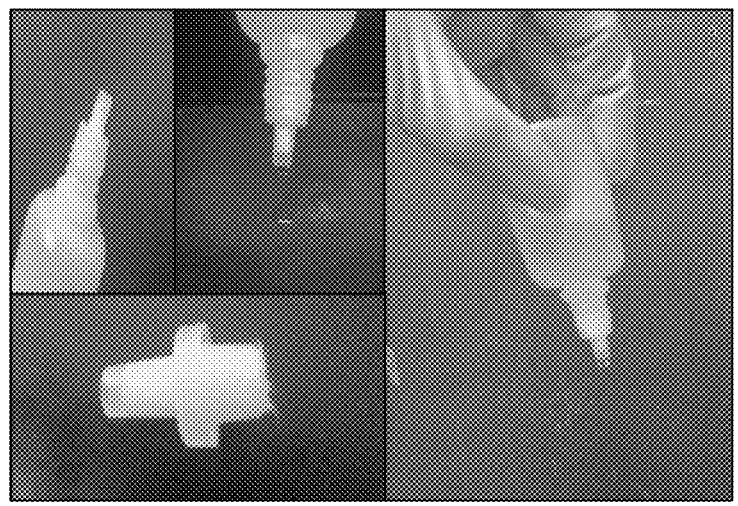
FIG. 1 shows photographs of an eye-drop filter bottle with a tapered plug embedded with approximately 0.1 g of poly(hydroxyethyl methacrylate) (p-HEMA) or 0.07 g of poly(hydroxyethyl methacrylate-co-tert-butyl methacrylate) (p-HEMA/Tert-Butyl Methacrylate) particle matrix, according to an embodiment of the disclosure.

The present disclosure provides a preservative removal agent. A preservative removal agent may rapidly and selectively remove preservatives of the present disclosure from a solution, emulsion, or suspension comprising a therapeutic agent. The preservative removal agent may rapidly and selectively extract the preservative, allowing the eye drop formulation to flow through the plug with minimal pressure drop, yet with sufficient time to remove the preservative and with sufficient surface area to adsorb the preservative. The matrix may comprise a material with a high affinity for the preservative, such as for example benzalkonium chloride (BAK), and low affinity for a therapeutic agent, such as a drug or other opthalmological agent.

Aspects of the present disclosure provide a preservative removal agent which may comprise a porous polymer matrix. In some cases, the preservative removal agent may comprise a homopolymer comprising a hydrophilic repeating unit. In some cases, the preservative removal agent may comprise a homopolymer comprising a hydrophobic repeating unit. The preservative removal agent may comprise a copolymer comprising at least one hydrophobic repeating unit and a least one hydrophilic repeating unit. In some cases, the polymer is copolymer. In some cases, the homopolymer or the co-polymer comprises a hydrophobic cross-linker. In some cases, the homopolymer of the co-polymer comprises a hydrophilic cross-linker. The polymer matrix may comprise a particulate plug.

In some embodiments, the present disclosure provides particles of polymers formed from hydroxyethyl methacrylate and hydrophobic methacrylates to form a medium to remove BAK selectively from an aqueous eye drop solution where the BAK is selectively absorbed from hydrophilic drugs in the solution. The presence of the hydrophobic portion of the copolymer allows for a significant reduction in the removal of the hydrophilic drugs from the solution compared to the drug removal using equivalent amounts of poly(hydroxyethyl methacrylate) (denoted "pHEMA" or "p-HEMA," herein) particles.

The present disclosure provides a particulate plug for removing a preservative from a solution comprising a drug. The particulate plug may comprise microparticles of a homopolymer comprising a hydrophilic repeating unit or a copolymer comprising at least one hydrophilic repeating unit and at least one hydrophobic repeating unit. The microparticles may be irregular-shaped rigid aggregates and may form a particulate plug having a hydraulic permeability greater than 0.01 Darcy (Da). The plug may fit an outlet of a container for a solution, emulsion, or suspension. In some cases, the homopolymer or the copolymer further comprises absorbed portions of a preservative to be removed and/or a drug for delivery in solution, emulsion, or suspension. The particulate plug may rapidly and selectively remove a preservative from the solution, emulsion, or suspension.

According to an embodiment of the disclosure, particles were formulated to include at least one hydrophobic monomer to discourage significant uptake of a hydrophilic drug. Particles that would cater to a system of hydrophilic ophthalmic drug formulations used for different treatment procedures and by different subjects are needed. To achieve this goal, t-Butyl Methacrylate, a hydrophobic monomer, is added along with HEMA to the monomer mixture without further altering the composition of the batch used for the preparation of p-HEMA particles, where the ratio of Tert-Butyl Methacrylate and HEMA in the monomer mixture was adjusted to minimize drug uptake also retain high partition coefficient of the system used to obtain high BAK removal rates.

The selectivity of a matrix material of the present disclosure may refer to the degree to which a preservative is absorbed by the matrix versus the degree to which therapeutic agent is absorbed. The selectivity may be related to the relative partition coefficients of the preservative and the therapeutic agent. The selectivity may be related to the relative concentrations of preservative and the therapeutic agent in a dose. The selectivity may be related to the change in the relative concentrations of the preservative and the therapeutic agent in a dose versus in a pharmaceutical formulation before exposure to the preservative removal agent. The selectivity may be related to the change in the relative concentrations of the preservative and the therapeutic agent over time in a dose or in a formulation. In some cases, the selectivity may be quantified spectroscopically.

Preservative Removal Agent

In some embodiments, the disclosure provides pharmaceutical formulations comprising a preservative and a therapeutic agent. The formulation may comprise a solution, emulsion, or suspension of a therapeutic agent and a preservative. In some embodiments, the formulation may comprise a preservative removal agent. (e.g. in embodiments where the preservative removal agent may comprise a portion of a solution, emulsion, or suspension comprising a therapeutic agent and a preservative). In other embodiments, the preservative removal agent may be separate from the solution, emulsion, or suspension comprising the therapeutic agent and the preservative (e.g. in embodiments where the preservative removal agent may be located within the neck of a bottle). Optionally in any embodiment, the solution, emulsion, or suspension may additionally comprise one or more pharmaceutically acceptable excipients.

In some embodiments, a matrix disposed within a nozzle may be a porous polymeric matrix. Applying a pressure behind the nozzle may cause fluid to flow through the nozzle via the flow path, along which path the preservative may be removed by adsorption onto the matrix. The polymer material, the hydraulic permeability, the partition coefficient, the adsorption rate, and the pore size in combination may aid in the absorption of all or most of the preservative from the solution and thus patient eye drops. The reduced preservative solution may subsequently be delivered directly to the eye. The porous polymeric matrix may rapidly and selectively extract the preservative, allowing the eye drop formulation to flow through the plug with minimal pressure drop, yet with sufficient time to remove the preservative and with sufficient surface area to adsorb the preservative.

The porous polymeric matrix may comprise a variety of materials. Such material may be safe and biocompatible. Such material may comprise but is not limited to, for example, Poly(2-hydroxyethyl methacrylate) (pHEMA), poly(hydroxylethyl methacrylate-co-methacrylic acid) (p-HEMA/MAA), poly(hydroxyethyl methacrylate-co-tert-butyl methacrylate) (p-HEMA/TBM), dimethyl acrylamide, methyl methacrylate, silicones, and/or any combination of the preceding materials. The matrix may comprise a material with a high affinity for the preservative, such as for example benzalkonium chloride (BAK), and low affinity for a drug or other opthalmological agent. The porous polymeric matrix may comprise a high selectivity and affinity for the preservative, such that at least 50 percent of the preservative may be removed and at least 50 percent of the drug may be retained by the solution. In some embodiments, a matrix disposed within a nozzle may be a porous polymeric matrix. The porous polymeric matrix may comprise a variety of materials. Such material may be safe and biocompatible.

In some embodiments, the matrix material is a copolymer. A copolymer may comprise more than one species of monomer. Copolymers may be branched. Copolymers may be linear. Copolymers may comprise crosslinkers. Copolymers may be block copolymers, may be alternating copolymers, may be periodic copolymers, may be gradient copolymers may be statistical copolymers, may be sterablock copolymers. The copolymers may exhibit phases of differing hydrophobicity or hydrophilicity. The hydrophobicity and/or hydrophilicity of the one or more monomers or cross-linkers may control the binding of a therapeutic agent or a preservative to the plug material.

Non-limiting examples of a preservative removal agents may comprise solid, gel, and/or particulate matrices. The preservative removal agent may act as a physical barrier or filter. Additionally or alternatively, the preservative removal agent may chemically remove a preservative such as by adsorption of the preservative onto the matrix. The preservative removal agent may be disposed in the outlet of a container, which container may contain the solution, emulsion, or suspension.

While exemplary systems and methods of the present disclosure may be directed to Poly(2-hydroxyethyl methacrylate) (pHEMA), poly(hydroxylethyl methacrylate-co-methacrylic acid), poly(hydroxyethyl methacrylate-co-tert-butyl methacrylate) (p-HEMA/TBM), dimethyl acrylamide, methyl methacrylate in combination with BAK, any matrix material and any preservative may be used such that the drug's partition coefficient into the matrix may be lower by at least an order of magnitude, and more preferably by two-orders of magnitude than the matrix's affinity for the preservative. For example, pHEMA may bind BAK with a partition coefficient of about 100-500 depending on the BAK concentration and the structure of the matrix. In some embodiments, the matrix may comprise a partition coefficient for the preservative from the solution, emulsion, or suspension of, for example, at least 10, at least 100, at least 1000, at least 10,000, or within a range defined by any two of the preceding values. By contrast, the desired partition coefficient of the drug is lower than 1 and more preferably lower than 0.5, and even more preferably less than 0.1. In embodiments, the matrix material can be selective for the preservative relative to the drug such that, for example, the partition coefficient for the preservative can be at least tenfold, at least fiftyfold, or at least one hundred fold greater than the partition coefficient the drug. Additionally or alternatively, the adsorption rate constant may be sufficiently high so that the time for adsorption of a drug molecule to the polymer may be less than the time to form a drop. The time to form a drop may comprise a time within a range from 0.1 to 10 seconds.

The matrix may display a high hydraulic permeability such that relatively little pressure may be required to dispense a fluid. The hydraulic permeability may depend on the design of the filter. Larger pores may allow for higher flow for a given pressure drop. In some embodiments, hydraulic permeability may be larger than about 0.01 Darcy (Da). A nozzle may comprise a permeability of about 0.1 Darcy. A hydraulic permeability of 1 to 10 Darcy may allow fluid to be retained in the filter during instances when the pressure may be lowered subsequent to formation of a drop. A larger hydraulic permeability may allow the same plug to work for a wide range of formulations including, for example, high viscosity formulations, such as rewetting eye drops. In some embodiments, the porous polymeric matrix comprises a hydraulic permeability of, for example, 0.01 Da, 0.1 Da, 1 Da, 10 Da, 100 Da, 1000 Da or a hydraulic permeability within a range defined by any two of the preceding values.

In some embodiments, the matrix may be highly porous containing large channels through which liquid can flow. The pore or channel size in the matrix may be small enough so that the molecules, which may initially be far from the surface of the polymer in the matrix, may diffuse towards the polymer and adsorb. A matrix may comprise large interconnected pores or channels which may allow flow of solution and adsorption of the preservative into the pores or channels. The matrix may be formed as a porous gel, as a packed bed, and/or a structure formed by 3D printing soft lithography, electrospinning, or any other appropriate method. In some embodiments, the matrix may comprise a microporous gel. In some embodiments, the matrix may comprise a packed bed of pHEMA or other polymeric particles. The particles may be macroporous. The particles may be spherical or non-spherical. In some embodiments, the polymeric matrix may comprise nano or micron sized polymeric particles (e.g., nanogels or microgels). In some embodiments, the polymeric matrix may comprise a cryogel. In some embodiments, the particles themselves may directly impart the preservative effect, such as colloidal silver nanoparticles.

In some embodiments, the particles may need to be stably held in the nozzle from which the formulation elutes from a container and thereby prevented from eluting from the nozzle. In some cases, the matrix may be sintered to fuse the particulate plug into porous monolith. In some cases, the device may have a cartridge or other assembly to retain the matrix in the nozzle. The device may have a solution permeable bag to retain the matrix. The device may comprise solid walls with a solution permeable bottom. The device may comprise entrance and exit faces with a matrix material therebetween. The entrance and exit faces may comprise solution permeable membranes. The entry and exit faces may comprise a filter. The entrance and exit faces may comprise a screen. The particles may be attached to the container walls through long polymeric chains and/or by placing a filter at the exit from the device. The device may comprise a packaging for delivery to a patient. The packaging may secure the device such that the device may not be compressed until the device is delivered to the patient. The packaging may secure the exit face from allowing the formulation to exit the bottle. The packaging may comprise a removable cap, a break-off cap, etc.

In some embodiments, the filter placed at the exit to prevent particles from eluting could also provide other functionalities such as antibacterial surface. Additionally or alternatively, the walls of the container or other surfaces may comprise preservative attached thereupon and/or incorporated therein. In some embodiments, a preservative source comprises a pHEMA membrane with 1-10% by volume equilibrated with BAK could be incorporated into the container. In some embodiments, the matrix comprises a pHEMA membrane pre-loaded with BAK at a concentration to inhibit microbial growth over time.

In certain embodiments, particles described herein have an average largest dimension from about 1 nm to about 10 m, about 1 nm to about 5 m, about 1 nm to about 2 μm, about 1 nm to about 1 μm, about 1 nm to about 900 nm, about 1 nm to about 800 nm, about 1 nm to about 700, about 1 nm to about 600 nm, about 1 nm to about 500 nm, about 1 nm to about 400 am, about 1 nm to about 300 nm, about 1 nm to about 200 nm, or even from about 1 nm to about 100 nm. In certain embodiments, the average largest dimension is the average largest diameter or the average equivalent diameter.

In certain embodiments, greater than 80% of the particles, such as greater than 90% or greater than 95% of the particles in the formulation have an average largest particle diameter of from about 1 nm to about 10 μm, about 1 nm to about 5 μm, about 1 nm to about 2 μm, about 1 nm to about 1 m, about 1 nm to about 900 μm, about 1 nm to about 800 nm, about 1 nm to about 700, about 1 nm to about 600 am, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, particles described herein have an average diameter from about 100 nm to about 10 μm, about 100 nm to about 5 μm, about 100 nm to about 2 μm, about 100 nm to about 1 μm, about 100 nm to about 900 nm, about 100 nm to about 800 nm, about 100 nm to about 700, about 100 nm to about 600 nm, about 200 nm to about 500 nm, about 250 nm to about 600 am, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In certain embodiments, greater than 80% of the particles, such as greater than 90% or greater than 95% of the particles in the formulation have an average diameter from about 100 nm to about 10 µm, about 100 µm to about 5 µm, about 100 nm to about 2 µm, about 100 nm to about 1 µm, about 100 nm to about 900 nm, about 100 nm to about 800 nm, about 100 nm to about 700, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter The matrix may comprise a tortuosity such that the flow path of a solution, emulsion, or suspension through the nozzle may be significantly increased. In an embodiment where the matrix is a packed bed of macroporous particles, the packed beds of macroporous particles may have three levels of porosity: the space between the particles, the macropores in the particles, and the inherent porosity of the polymer. In such an embodiment, all three levels of porosity may contribute to the tortuosity of the matrix.

Therapeutic Agent

Embodiments of the present disclosure may provide a therapeutic agent for delivery to an eye. A therapeutic agent may be integrated into a fluid, which may flow from a container to an eye through a nozzle. In some embodiments, the fluid may comprise a solution, emulsion, or suspension comprising a therapeutic agent. The solution, emulsion, or suspension may comprise a therapeutic agent.

Exemplary therapeutic agents which may be used in conjunction with a nozzle include but are not limited to: timolol malcate, dorzolamide, dexamethoasone phosphate, dexamethasone. Betimol®, olopatadine, brimonidine, trahydrozoline, latanoprostene bunod, latanoprost, and combinations of any two or more thereof. Therapeutic agents may comprise brand name drugs and formulations including, but not limited to, Timoptic, Xalatan, Combingan, Lumigan, Pataday, Pazeo, Trusopt, Cosopt, Alphagan, Visine, Vyzulta, Veseneo, and other agents described herein such as in the following tables. The therapeutic agents may be dissolved in aqueous solution. The solution may be sterilized and buffered to appropriate pH. In some embodiments, the solution may comprise inactive ingredients such as sodium chloride, sodium citrate, hydroxyethyl cellulose, sodium phosphate, citric acid, sodium dihydrogen phosphate, polyoxyl 40 hydrogenated castor oil, tromethamine, boric acid, mannitol, edetate disodium, sodium hydrdroxide, and/or hydrochloric acid. In some embodiments, the fluid comprises a preservative in addition to a therapeutic agent Exemplary preservatives include but are not limited to: benzalkonium chloride (BAK), alcohols, parahens, methyl parahen, propylparahen, EDTA, chlorbexidine, quaternary ammonium compounds, Purite®, stabilized oxychloro complexes, Sofzia®, sorbic acid. Sodium perborate, polyquarternium-1, chlorobutanol, cetrimonium chloride, edatate disodium, etc.

Therapeutic agents for the treatment of for example, dry eye, bacterial infection, glaucoma, hypertension, inflammation, allergic conjunctivitis, hypotrichosis of the eyelashes, fungal infection, etc. and therapeutic agents used for local anesthetic, pupil dilation, etc. may be administered to a patient as a solution, emulsion, or suspension delivered to an eye topically via a dropper bottle or similar delivery mechanism. The solution, emulsion, or suspension may be subject to contamination such as microbial, fungal, or particulate contamination, which may be adverse to patient health. In order to prevent such contamination a preservative may be added to the solution, emulsion, or suspension; however, patient exposure to preservatives may have adverse effects to eye health.

The present disclosure provides one or more therapeutic agents removable by a preservative removing device of the present disclosure, which may comprise one or more ophthalmic agents. Therapeutic agents may comprise compounds and salts, for use in the treatment of ophthalmic diseases. The disclosed compounds and salts can be used, for example, for the treatment or prevention of vision disorders and/or for use during opthalmological procedures for the prevention and/or treatment of ophthalmic disorders. The flowing list of examples are not intended to be limiting.

In some embodiments, the therapeutic agent to be dispensed comprises an active ingredient selected from cyclosporine and lifitegrast. In such embodiments, the therapeutic agent may be an active ingredient in the treatment of dry eye.

In some embodiments, the therapeutic agent to be dispensed comprises an active ingredient selected from sulfacetamide sodium, ofloxacin, gatifloxacin, ciprofloxacin, moxifloxacin, tobramycin, levofloxacin, prednisolone acetate, polymyxin B sulfate, and trimethoprim. In some embodiments, the therapeutic formulation to be dispensed comprises the active ingredients sulfacetamide sodium and prednisolone acetate. In some embodiments, the therapeutic formulation to be dispensed comprises the active ingredients polymyxin B sulfate and trimethoprim. In such embodiments, the therapeutic agent may be an active ingredient in the treatment of a bacterial infection.

In some embodiments, the therapeutic agent to be dispensed comprises an active ingredient selected from brimonidine tartrate, bimatroprost, levobunolol hydrochloride, brinzolamide, betaxolol hydrochloride, pilocarpine hydrochloride, apraclonidine, travoprost, timolol maleate, latanoprost, dorzolamide hydrochloride, and tafluprost. In some embodiments, the therapeutic formulation to be dispensed comprises the active ingredients brimonidine tartrate and timolol maleate. In some embodiments, the therapeutic formulation to be dispensed comprises the active ingredients brinzolamide and brimonidine tartrate. In such embodiments, the therapeutic agent may be an active ingredient in the treatment of glaucoma or hypertension.

In some embodiments, the therapeutic agent to be dispensed comprises an active ingredient selected from ketorolac tromethamine, fluorometholone, prednisolone acetate, difluprednate, fluorometholone acetate, nepafenae, dexamethasone, diclofenac sodium, bromfenac, gentamicin, tobramycin, neomycin, and polymyxin B sulfate. In some embodiments, the therapeutic formulation to be dispensed comprises the active ingredients gentamicin and prednisolone acetate. In some embodiments, the therapeutic formulation to be dispensed comprises the active ingredients tobramycin and dexamethasone. In some embodiments, the therapeutic formulation to be dispensed comprises the active ingredients neomycin, polymyxin B sulfate and dexamethasone. In such an embodiment, the therapeutic agent may be an active ingredient in the treatment of inflammation.

In some embodiments, the therapeutic agent to be dispensed comprises an active ingredient selected from nedocromil sodium, epinastine HCl, alcaftadine, lodoxamide tromethamine, emedastine difumarate, and olopatadine hydrochloride. In such embodiments, the therapeutic agent may be an active ingredient in the treatment of allergic conjunctivitis.

In some embodiments, the therapeutic agent to be dispensed comprises an active ingredient selected from proparacaine hydrochloride and tetracaine hydrochloride. In such embodiments, the therapeutic agent may be a local anesthetic.

In some embodiments, the therapeutic agent to be dispensed comprises an active ingredient selected from cyclopentolate hydrochloride, atropine sulfate, and tropicamide. In some embodiments, the therapeutic formulation to be dispensed comprises the active ingredients cyclopentolate hydrochloride and phenylephrine hydrochloride. In such embodiments, the therapeutic agent may dilate pupils.

In some embodiments, the therapeutic agent to be dispensed comprises the active ingredient natamycin. In such embodiments, the therapeutic agent may be an active ingredient in the treatment of fungal infection.

In some embodiments, the therapeutic agent to be dispensed comprises an active ingredient selected from lipoic acid choline ester chloride, rebamipide, pilocarpine, aceclidine, tropicamide, sodium hyaluronate, diclofenac sodium, pilocarpine HCl, and ketorolac. In some embodiments, the therapeutic formulation to be dispensed comprises the active ingredients aceclidine and tropicamide. In some embodiments, the therapeutic formulation to be dispensed comprises the active ingredients sodium hyaluronate and diclofenac sodium and pilocarpine HCl. In some embodiments, the therapeutic formulation to be dispensed comprises the active ingredients pilocarpine and ketorolac. In such embodiments, the therapeutic agent may be an active ingredient in the treatment of presbyopia.

Preservative

The present disclosure provides one or more preservatives for solutions, emulsions, or suspensions of therapeutic agents of the present disclosure. Preservatives may comprise compounds and salts, for use as preservatives for solutions, emulsions, or suspensions of therapeutic agents. The one or more preservatives may for example prevent microbial and/or fungal growth. The one or more preservatives may for example prevent physical or chemical deterioration of a therapeutic agent.

Non-limiting examples of preservative agents include benzalkonium chloride, ethylenediaminetetraacetic acid (EDTA), chlorbutanol, phenylmercuric acetate, phenylmercuric nitrate, chlorhexidine acetate, thimerosal, benzethonium chloride, sorbic acid, alcohols, parabens (e.g., methylparaben, polyparaben), chlorhexidine, quaternary ammonium compounds, polyquaternium-1 (Polyquad®), Purite®, stabilized oxychloro complexes, Sofzia®, sodium perborate (GenAqua®), cetrimonium chloride, edetate disodium, etc. In some embodiments, a formulation of the disclosure does not include a preservative.

In some embodiments, the particulate plug may further include a preservative removing compound or a preservative deactivating compound. Preservative removing or deactivating compounds can decrease toxicity of a formulation to be delivered through typical separation methods including, but not limited to, adsorption, ion exchange, chemical precipitation, or solvent extraction. Preservative removing or deactivating compounds can include, but are not limited to, activated charcoal, antioxidants, metal chelating compounds, anionic hydrogels, cationic compounds, neutralizing agents, or combinations thereof.

The Purite® preservative system includes Stabilized Oxychloro Complex (SOC), a combination of chlorine dioxide, chlorite and chlorate. When exposed to light, SOC dissociates into water, oxygen, sodium and chlorine free radicals which cause oxidation of intracellular lipids and glutathione, interrupting vital enzymes for cell function and maintenance. For preservatives such as Purite® which produce chlorine free radicals the particulate plug of the disclosure can include a material that has a high affinity for free radicals such as activated charcoal or antioxidants such as vitamin E.

The SofZia® preservative system in Travatan Z (Alcon Laboratories, Fort Worth, Tex.) contains borate, sorbitol, propylene glycol, and zinc. Without intending to be bound by theory, it is believed that the preservative effect is from a combination of borate and zinc. For preservatives including borate and zinc, such as SofZia®, the particulate plug of the disclosure can include a metal chelating agent such as EDTA, anionic hydrogels that can extract cationic zinc through electrostatic interactions, cationic hydrogels or resins that can extract anionic borate ions through electrostatic interactions, or a neutralizing agent that can neutralize boric acid.

The materials that can sequester the preservative can be incorporated into the particulate plug as microparticles, such as particles of activated charcoal. The microparticles can be packed into the particulate plug such that the liquid has sufficient space in between the particles to flow out, while also providing sufficient contact area for binding. Alternatively, the sequestering materials could be incorporated into particles of other suitable materials such as the polymer particles of the disclosure to facilitate the contact between the eluding formulation and the sequestering material. In some cases, the sequestration material can be integrated into the polymer covalently. For example, negative ions that can complex with zinc could be incorporated into polymers. The sequestering material can be a nanoparticle or can be incorporated into a nanoparticle, which could in turn be dispersed into the polymer particles that form a packed bed in the tip. The nanoparticle could also be deposited just on the surface of the larger particles. The sequestering material could also form tubes that can be arranged in parallel to provide the path for liquid to flow out and sequestration to occur on the surface.

The materials present in the particulate plug to neutralize the free radicals in the formulation, for example, vitamins, can be incorporated into the polymer particles that form the particulate plug. Bases can be incorporated to bring the pH to a level that is comfortable in the eyes. The polymer particles can be loaded with vitamin E for example by soaking the particles in a solution of vitamin E dissolved in an organic liquid, leading to uptake of vitamin E into the particles. Subsequently, the organic liquid such as ethanol can be evaporated or extracted into water to form particles loaded with vitamin E. The material of the particles that is loaded with vitamin E could be chosen to achieve other beneficial purposes such as extraction of some other component of the preservative. Bases could be directly integrated into the hydrogel preparations.

The preservative effect of the formulations can be improved by incorporation of another preservative such as Benzalkonium Chloride so that the formulation can pass EP-A criterion as well. The added BAK or the other preservative can be removed by the particulate plug to achieve improved preservative performance without increasing toxicity.

The particulate plug including a preservative removing compound or preservative deactivating compound can be formed in various shapes such as spheres, cylinders, tubes, highly irregular, flat sheets etc, where the surface could be rough or smooth. The particles or other shapes integrated into the tip can contain some preservative to ensure that the tip itself remains sterile. The preservative pre-loaded into the tip could be loaded via adsorption or be chemically attached to the material through a bond. For example, Polyquaternium can be integrated into the polymer forming the particles. The covalent attachment will prevent diffusion of the pre-loaded preservative into the tear film. Alternatively, the pre-loaded preservative could be sufficiently large in molecular weight or have very low partitioning into the eluding formulation.

In cases wherein the particulate plug including a preservative removing compound or a preservative deactivating compound is intended to add a component to the eluding formulation, the amount of that material in the particulate plug will be sufficiently large to ensure that there is sufficient amount remaining for the entire bottle, or at least 90% of the bottle. In cases wherein the particulate plug including a preservative removing compound or a preservative deactivating compound is intended to sequester a component from the eluding formulation, the volume and area in the particulate plug will be sufficiently large to sequester the desired component from at least 90% of the formulation in the bottle.

The present disclosure provides salts of any one or both of a therapeutic agent and a preservative. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is an ammonium salt, a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

The methods and formulations described herein include the use of amorphous forms as well as crystalline forms (also known as polymorphs). Active metabolites of compounds or salts of any one of the compounds of the present disclosure having the same type of activity are included in the scope of the present disclosure. In addition, the compounds described herein can exist in unsolvated as well as solvated forms with pharmaceutically acceptable solvents such as water, ethanol, and the like. The solvated forms of the compounds and salts presented herein are also considered to be disclosed herein.

The compounds may be synthesized using conventional techniques. Advantageously, these compounds are conveniently synthesized from readily available starting materials. Synthetic chemistry transformations and methodologies useful in synthesizing the compounds described herein are known in the art.

Solution, Emulsion, or Suspension

Provided herein are solutions, emulsions, or suspensions of a therapeutic agent and a preservative. In some embodiments, provided herein are compositions comprising a therapeutically effective amount of any compound or salt of any one of the preservatives and/or therapeutic agents of the present disclosure. In some embodiments, a therapeutic solution, emulsion, or suspension may be used in any of the methods described herein. The solution, emulsion, or suspension may additionally comprise one or more pharmaceutically acceptable excipients.

In some embodiments, a compound of preservative and/or therapeutic agent may be used for the treatment of a therapeutic disorder such as, dry eye, bacterial infection, glaucoma, hypertension, inflammation, allergic conjunctivitis, hypotrichosis of the eyelashes, fungal infection, etc. Additionally or alternatively, a compound of a preservative and/or therapeutic agent may be used during a preventative, diagnostic, or therapeutic opthalmological procedure, for example, local anesthetic, pupil dilation, etc. A formulation administered to the eye may be administered topically, for example, with an eye drop.

A compound of the therapeutic agent described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a therapeutic agent described herein may be present in a solution, emulsion, or suspension within a range of concentrations, the range being defined by an upper and lower value selected from any of the preceding concentrations. For example, the compound or salt of a therapeutic agent of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

In some embodiments, a solution, emulsion, or suspension such as an aqueous solution of the disclosure, comprises from about 0.001 wt % to about 0.3 wt % of the compound of any one of the preservatives disclosed herein. In some embodiments, a solution, emulsion, or suspension such as an aqueous solution of the disclosure, comprises about 0.001 wt %, about 0.002 wt %, about 0.003 wt %, about 0.004 wt %, about 0.005 wt %, about 0.006 wt %, about 0.007 wt %, about 0.008 wt %, about 0.009 wt %, about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 3 wt %, about 4 wt %, about 5 wt %, about 6 wt %, about 7 wt %, about 8 wt %, about 9 wt %, or about 10 wt % of a compound of the preservative described herein.

The preservative described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a preservative described herein may be present in a composition within a range of concentrations, the range being defined by an upper and lower value selected from any of the preceding concentrations. For example, the compound of a preservative of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Solutions, emulsions, or suspensions of the disclosure can be formulated at any suitable pH. In some embodiments, the pH of the solution emulsion or suspension is about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9 pH units. In some embodiments, the pH of the solution, emulsion, or suspension is from about 4 to about 10, about 5 to about 9, about 6 to about 8, about 6.5 to about 8, about 7 to about 8, about 7.2 to about 8, about 7.2 to about 7.8, about 7.3 to about 7.5, or about 7.35 to about 7.45. In some embodiments the pH of the solution, emulsion, or suspension is about 7.4.

In some embodiments, solutions, emulsions, or suspensions of the present disclosure further comprise one or more physiologically acceptable carriers including excipients and auxiliaries which facilitate processing of the pharmaceutical agent into preparations which are used pharmaceutically. Proper formulation is dependent upon the route of administration chosen.

In some embodiments, the addition of an excipient to a pharmaceutical formulation of the present disclosure can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical formulation of the present disclosure can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%. Examples of ranges which the viscosity change falls within can be created by combining any two of the preceding percentages. For example the addition of an excipient can increase or decrease the viscosity of the composition by 5% to 99%, by 10% to 95%, by 20% to 70% or by 35% to 55%.

In some embodiments, solutions, emulsions, or suspensions of the present disclosure further comprise an agent for adjusting the osmolarity of the solution, emulsion, or suspension. e.g., mannitol, sodium chloride, sodium sulfate, dextrose, potassium chloride, glycerin, propylene glycol, calcium chloride, and magnesium chloride. In some embodiments, the solution, emulsion, or suspension comprises from about 0.1 wt % to about 10 wt %, about 0.5 wt % to about 8 wt %, about 1 wt % to about 5 wt %, about 1 wt % to about 4 wt %, or about 1 wt % to about 3 wt % of an agent for adjusting the osmolarity of the solution, emulsion, or suspension. In some embodiments, the solution, emulsion, or suspension of the disclosure has an osmolarity from about 10 mOsm to about 1000 mOsm, about 100 mOsm to about 700 mOsm, about 200 mOsm to about 400 mOsm, about 250 mOsm to about 350 mOsm or even about 290 mOsm to about 310 mOsm.

The amount of the excipient in a solution, emulsion, or suspension of the present disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form. The amount of the excipient in a solution, emulsion, or suspension can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass or by volume of the unit dosage form.

The ratio of a compound of a therapeutic agent of the present disclosure to an excipient in a pharmaceutical formulation of the present disclosure can be about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1 about 30:about 1, about 25:about 1, about 20:about 1, about 15:about 1, about 10:about 1, about 9:about 1, about 8:about 1, about 7:about 1, about 6:about 1, about 5:about 1, about 4:about 1, about 3:about 1, about 2:about 1, about 1:about 1, about 1:about 2, about 1:about 3, about 1:about 4, about 1:about 5, about 1:about 6, about 1:about 7, about 1:about 8, about 1:about 9, or about 1:about 10. The ratio of a compound of a therapeutic agent to an excipient in a solution, emulsion, or suspension of the present disclosure can be within the range of between about 100:about 1 and about 1 to about 10, between about 10:about 1 and about 1:about 1, between about 5:about 1 and about 2:about 1.

Pharmaceutically acceptable carriers are well known in the art and include, for example, aqueous solutions such as water or physiologically buffered saline or other solvents or vehicles such as glycols, glycerol, oils such as olive oil, or organic esters. The excipients can be chosen, for example, to effect delayed release of an agent or to selectively target one or more cells, tissues or organs. The composition can also be present in a solution suitable for topical administration, such as an eye drop.

In some embodiments, the solution emulsion or suspension provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and combinations thereof.

Methods for the preparation of compositions comprising the compounds described herein can include formulating the compounds with one or more inert, pharmaceutically-acceptable excipients. Liquid compositions include, for example, solutions in which a compound is dissolved, emulsions comprising a compound, or a solution containing liposomes, micelles, or nanoparticles comprising a compound as disclosed herein. These compositions can also contain minor amounts of nontoxic, auxiliary substances, such as wetting or emulsifying agents, pH buffering agents, and other pharmaceutically-acceptable additives.

EXAMPLES

Hydrophilic Drugs
Partition Coefficient of API and BAK in the Particle Matrix

Figure 7:
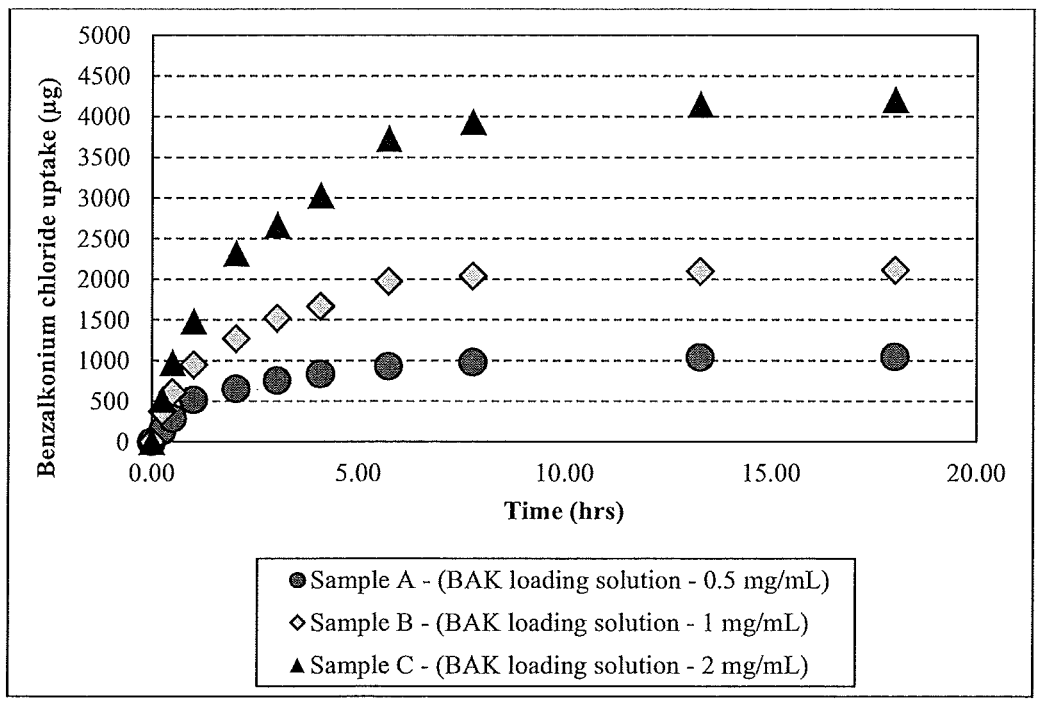
FIG. 7 is a plot of the uptake profiles of Benzalkonium chloride (BAK)/PBS aqueous solution in lab-made a 100 pm thick p-HEMA hydrogels for BAK/PBS concentrations uptake that range from 0.5 mg/ml to 2 mg/ml with volumes of aqueous BAK/PBS solution lens of 2.5 mL for the three concentrations tested with uptake data plotted as mean±SD with n=1.

The partition coefficients of hydrophilic drugs and BAK in p-HEMA. p-HEMA/t-butyl methacrylate, and p-HEMA/TRIS/t-butyl methacrylate particles were obtained by drug uptake studies. The mass of drug or BAK partitioned into p-HEMA hydrogel matrix was determined by monitoring the amount of drug or BAK lost in the concentrated aqueous drug/PBS or BAK/PBS loading solutions. The amount of drug loss from the concentrated aqueous phase was quantified by time-dependent absorbance measurements using UV-Vis spectrophotometry in a broad spectral range. FIG. 7 is a plot of the uptake profiles of Benzalkonium chloride (BAK)/PBS aqueous solution in lab-made a 100 μm thick p-HEMA hydrogels for BAK/PBS concentrations uptake that range from 0.5 mg/ml to 2 mg/ml with volumes of aqueous BAK/PBS solution lens of 2.5 mL for the three concentrations tested with uptake data plotted as mean±SD with n=1. The initial loading concentration of BAK used for partition coefficient studies with p-HEMA/Tert-butyl methacrylate particles was 0.1 mg/ml, whose magnitude of absorbance in the UV-spectra recorded at a 258 nm was around 0.1.

Time-dependent equilibrium interfacial tension measured via pendant drop tensiometry can be used to quantify the amount of BAK loss from the concentrated aqueous phase. A loading solution was withdrawn from the vial for recording of the equilibrium interfacial tension and dynamic interfacial tension of the suspended formulation. The loading solution was replaced after the duration of dynamic interfacial tension measurement. Similar measurements were repeated periodically for successive batches of loading solution until the system reached equilibrium. The dynamic concentration of the BAK in the loading solution was calculated based on the steady state Langmuir adsorption isotherm.

All interfacial tension measurements were conducted at a room temperature of approximately 25° C. The partition coefficient of drug or BAK solution in the particle matrix is given by $$k = \frac{C_{p,f}}{C_{w,f}} = \frac{V_w(C_{w,f} - C_{w,i})}{V_p C_{w,f}}, \quad \text{(Equation 1)}$$

where $V_w$ and $V_p$ are volumes of drug-PBS/BAK-PBS aqueous solution and volume of the particle matrix respectively, $C_{p,f}$ and $C_{w,f}$ denote the drug or BAK concentration in the particle matrix and aqueous phase at equilibrium, and $C_{w,i}$ i represents the initial concentration of the drug or BAK loading solution. The calculated partition coefficient of BAK of >400 in both p-HEMA gels and particles estimated by both UV spectra and interfacial tension measurements showed promise of p-HEMA as a filter material. Further, the calculated BAK partition coefficient of 322.94 in p-HEMA (25 v/v %)/Tert-butyl (75 v/v %) methacrylate particles showed promise for filter materials compatible with a wide range of hydrophilic drugs. Table 1 provides a summary of calculated partition coefficient of BAK in a 100 μm thick p-HEMA hydrogel.

TABLE 1

Summary of BAK loading experiments in lab made p-HEMA gels. Data are shown for 1 experimental run per loading BAK/PBS concentrated solution.

|  | Material A p-HEMA | Material B p-HEMA | Material C p-HEMA |
| --- | --- | --- | --- |
| BAK loading solution concentration (mg/ml) | 0.5 | 1 | 1.94 |
| Loaded BAK Content (μg) [a] | 1048.02 | 2110.72 | 4209.94 |
| Partition coefficient of BAK (K-BAK) [b] | 411.2 | 451.8 | 548.8 |

[a] Loading duration time is defined as the time to reach 90% of the cumulative drug uptake at equilibrium.
[b] The amount of drug loaded in lens as the lens was soaked in 2.5 mL of 0.5 mg/mL, 1 mg/mL, and 1.94 mg/mL BAK/PBS solution.
[b] Partition coefficient of BAK calculated based on measured mass of the lens with an approximate gel density of 1 g/cc (~30 μL). The ratio of volume of the loading solution to the gel's volume is ~83.33.

The partition coefficient of BAK in p-HEMA and p-HEMA/Tert-butyl methacrylate particle matrices were obtained by uptake studies. 12.5 mg of synthesized, cleaned and dried p-HEMA and p-HEMA/TBM particle matrices with different volume fractions of HEMA and TBM were soaked in BAK/PBS loading solutions with BAK concentrations ranging from 0.5-1 mg/ml. The mass of BAK partitioned in the p-HEMA and p-HEMA/TBM particle matrix was determined by monitoring the amount of BAK lost in the concentrated aqueous BAK/PBS loading solutions. The amount of BAK lost from the concentrated aqueous phase was quantified by time-dependent absorbance measurements using UV-Vis spectrophotometry (Genesys™ 10 UV, Thermo Spectronic, Rochester. N.Y., USA) over a wavelength range of 190-500 nm. Similar measurements were repeated periodically for successive batches of loading solution until the system reached equilibrium.

Figure 24:
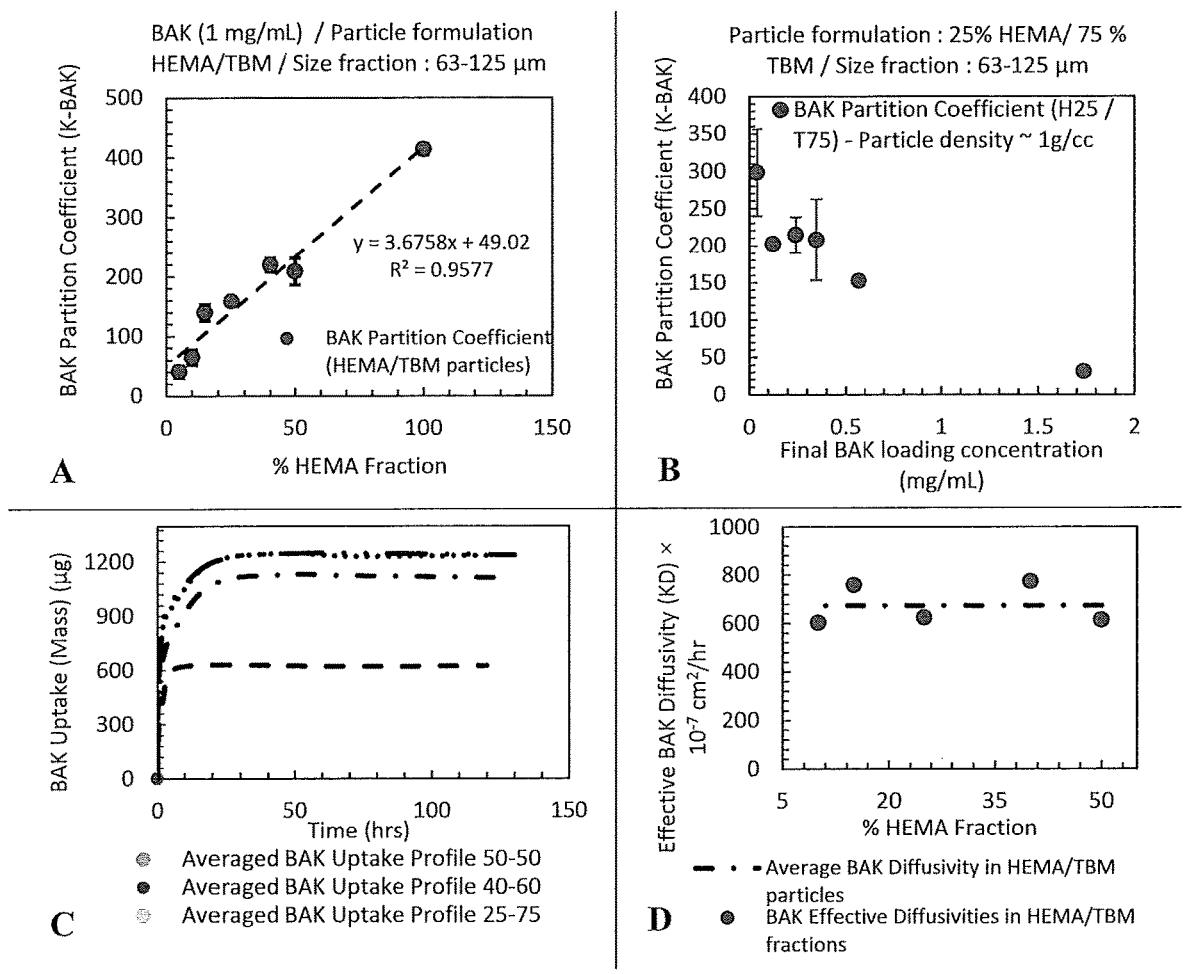
FIG. 24 shows a summary of A and B: BAK partition coefficients in p-HEMA/TBM matrices and its concentration dependence in the optimized 25% HEMA/75% TBM particles. C: A 20 hour BAK equilibration within the particle matrix indicates that a day's waiting period is critical for BAK redistribution within the filter bed. The corresponding effective diffusivities of BAK in p-HEMA/TBM systems are shown in D. Effective diffusivity of BAK is independent of composition type.

The calculated partition coefficient of BAK of >400 in p-HEMA particles estimated by UV spectral measurements showed promise of p-HEMA as a filter material. Further, the calculated BAK partition coefficient of 158 in p-HEMA (25 v/v %)/Tert-butyl (75 v/v %) methacrylate particles (FIG. 24B) showed promise for filter materials compatible with a wide range of hydrophilic drugs. FIG. 24A summarizes the calculated partition coefficient of BAK from experimental uptake data for p-HEMA and p-HEMA/TBM particle matrices.

The partition coefficient of hydrophilic drugs tested (Timolol Maleate. Levofloxacin, Dorzolamide, Brimonidine Tartrate. Combigan, and commercial Visine eye drops) were too low to be measured by this approach because the particle volume in the tests were too low to cause measurable decrease in the concentration during equilibration. As an alternative, to get an approximate estimate of partition coefficient in these particles matrices, the uptake of the active pharmaceutical ingredient (API) in the TIP assembled on an eye drop bottle was used. The volume ratio between the particle in the filter plug and the drop entrained in the plug after dosing the first drop is approximately 1:1. Thus, if a TIP is filled with a drug solution and left undisturbed for sufficiently long time, the concentration of the drug in the formulation may decrease due to absorption and adsorption of the drug into the particles. If a drop is squeezed out of the TIP after equilibration, the concentration of the drug in the drop can be used to determine the partition coefficient.

Estimating mass transport properties may be beneficial to gain insight on the preservative removal process. Diffusivity of BAK governs its equilibration within the particle matrix and gives an estimate of a waiting period that is critical for >95% BAK removal in the subsequent drops dosed. The average diameter of the sieved HEMA/TBM particle matrices of different compositions was 94 μm. The solute diffusion (BAK transport) into the particle matrix was assumed to be a one-dimensional transport along the radial direction. To substantiate the assumption of one dimensional radial diffusion of BAK in these particle matrices, preservative uptake profiles were plotted as BAK uptake % as a function of square root of time. For diffusion controlled transport, during the first 40% of BAK uptake in HEMA/TBM particles, a linear dependence of % preservative uptake on square root of time was a characteristic feature of such transport.

A more accurate estimate BAK diffusivity was obtained by fitting the experimental BAK uptake data to a transient diffusion model under non-perfect sink conditions. The transport of solute through these polymerized hydrogel materials occurred through swelling of the gel, bulk and surface diffusion. To maintain the model's simplicity, we assumed preservative diffusion through the filter material to be purely Fickian. Assuming the BAK diffusivity, $D_g$ and partition coefficient K are independent of concentration of BAK, transport in the radial direction can be described as:

$$\frac{\partial C_g}{\partial t} = D_g \left( \frac{\partial^2 C_g}{\partial r^2} + \frac{2}{r} \frac{\partial C_g}{\partial r} \right), \quad (2)$$

where $C_g$ is the BAK concentration in the HEMA/TBM particle matrix. The boundary and initial conditions for diffusion in the particle matrix are $$\frac{\partial C_g}{\partial y_2}(y_2 = 0) = 0 \quad (3)$$

$$C(y_2 = h_g) = KC_f(t) \quad (4)$$

$$C_g(t=0) = 0. \quad (5)$$

The boundary condition (3) arises from symmetry of the particle matrix and that in (4) assumes equilibrium between concentration of the preservative in the gel matrix and the surrounding formulation present in the aqueous BAK solution in the vial. A mass balance on the aqueous BAK reservoir in the scintillation vial yields the following equation:

$$V_w \frac{dC_w}{dt} = -D_g A_g n_d \frac{\partial C_g}{\partial r}(r = R) \quad (6)$$

$$V_w \frac{dC_w}{dt} = -D_g \frac{3V_g}{R} \frac{\partial C_g}{\partial r}(r = R), \quad (7)$$

where $V_w$ is the volume of BAK/PBS solution in the aqueous reservoir whose concentration is 1 mg/mL The modelled diffusion equation was solved using finite difference schemes in MATLAB with BAK diffusivity and partition coefficient determined by curve fitting experimental BAK uptake data for different p-HEMA/TBM compositions to the model and optimization through fminsearch module. Reasonable fits between the uptake data and the model indicates validity of the proposed model. It is observed that for all HEMA/TBM particle compositions, there is no observable trend of effective diffusivity of BAK with monomer composition in these particles (FIG. 24D) in comparison to BAK diffusivity in the particle matrices which show a decreasing trend with increasing HEMA fraction (not shown). A 20 hour BAK equilibration within the particle matrix shown in FIG. 24C) indicates that a day's waiting period is advantageous for BAK redistribution within the filter bed prior dosing out successive drops of the medication.

Preservative Removal and Drug Uptake Studies—Lab-Made and Commercial Timolol Maleate/PBS Formulations Equilibrium interfacial surface tension of filtered 0.5% timolol formulation containing 0.01% (100 ppm) BAK monitored daily for 14 days along with the % of BAK removed is determined by measured surface tension and equivalent experiments carried out 0.01% BAK/PBS as an aqueous phase without timolol shows an increase in interfacial surface tension of the aqueous Timolol/BAK solution validating the removal of BAK from the formulation. A stark difference in interfacial tension values of 0.01% BAK calibration solution and the filtered formulation indicate at least 1 or higher log reduction of BAK concentration in the filtered aliquot dosed, which indicates a high partition coefficient of BAK into the p-HEMA particle matrix. In each run, 0.5 ml of Timolol/BAK solution dosed from the eye drop filter bottle with a pre-packed plug is used for surface tension measurements with the procedure repeated daily for 30 days.

To enhance the accuracy of the % BAK removal estimates, the equilibrium surface tension of a single batch of 0.5 ml PBS solution pushed through a control filter with ~0.1 g p-HEMA filter was recorded. The difference in measured equilibrium surface tension estimates between pure PBS solution and PBS-dosed from the filter packed with p-HEMA particles suggests impurities leached out of the particle matrix. To account for this difference, equilibrium surface tension of PBS-dosed from the filter with packed particles is taken as a reference for evaluation of % BAK removal from the drug formulation. A day long waiting period was considered a simulation of drop administration through the ocular route. From the perspective of selective preservative removal and drug uptake, a waiting period of 24 hours was favored to allow redistribution of the absorbed BAK and drug within the particle phase.

Since diffusion limits the rate of BAK and drug absorption into the particle matrix, it is potentially advantageous to estimate the time scale for diffusion from the aqueous formulation into the particle phase to allow mass transfer boundary layer growth and ensure redistribution within the particle matrix. Further, if the time scale of the waiting period is kept significantly lower than the diffusion time, there is a possibility of accumulation of BAK near the interface of the particle phase due to incomplete boundary layer growth. A possible outcome of a shorter waiting period may be a reduction in fractional preservative removal for successive formulation batch eluted. The thickness of the mass transfer boundary layer in the particles during this waiting period $t_d$ can be scaled as $\sqrt{4D_g t_d}$ where, $D_g$ is the diffusivity of DAK in the particles. A conservative estimate of diffusivity of BAK, $D_g$ in the particles of an average size of 1-mm size is determined to be larger than $1\times10^{-13}$ m$^2$/s. The mass of BAK taken up in this boundary layer can be approximated as $KC_0 S \sqrt{4D_g t_d}$, where K is the partition coefficient, $C_0$ is the BAK concentration in the formulation. S is the total surface area of the particles in the packet bed. The surface area S can be approximated as $3\varnothing V_{plug}/R_{particle}$, where $\varnothing$=0.5 and $V_{plug}$=0.1 mL are the volume fraction of the particles and volume of the packed bed respectively. To achieve a high efficacy of selective BAK removal, the mass of preservative in the boundary layer may exceed the mass in each drop dosed. Hence, the constraint on the time of elution $t_d$, $$K(3\varnothing V_{tip}/R_{particles})O\sqrt{4Dt_d} > V_{drop}, \quad \text{(Equation 8)}$$

where $V_{drop}$=30 µL is the volume of the drop. The threshold value for the time for elution is determined to be around 0.16 seconds, whose order of magnitude is lower than the 4 second duration needed for drop creation. The degree of BAK removal was nearly 98.5% for the first batch of filtered solution (0.5 mL) and remain above 96% for the subsequent batches measured. Interfacial surface tension measurements indicate that more than 95% BAK is selectively removed from more than 30 successive batches of 0.5 ml filtered Timolol/BAK formulation, thus showing no sign of saturation of p-HEMA particles with BAK. This analysis is a guide for designing the filter tip to achieve the desired removal of BAK.

Small particles may be beneficial to achieve a more effective removal of BAK. This is due to a larger surface area and also due to the shorter time needed for the BAK to diffuse to the center of the particles. However, without being limited by theory, small particles may lead to low hydraulic permeability which would increase the pressure drop needed to squeeze out the drops. A porous particles in the size range of 0.1 mm to a 10 mm may satisfy both of the objectives by increasing the available area while keeping hydraulic permeability high. Similarly, 0.1 mm to a 10 mm size particles that are aggregates of smaller particles may allow high hydraulic permeability while allowing fast diffusion into the entire aggregate particle. It may be preferable to design the device using porous particles or particles that are aggregates of smaller particles.

The % BAK removal was assessed for the commercially available 10 mL Timolol Maleate ophthalmic solution from Sandoz Inc. The concentration of timolol maleate and BAK in the commercial formulation was 0.5% and 0.01% respectively. Prior to dosing the first batch of filtered commercial timolol maleate solution, the commercial filter bottle packed with ~0.1 g p-HEMA particles in the plug was inverted for 2 weeks to allow pre-equilibration of particles with the drug formulation. This protocol is followed to reduce the uptake of timolol by p-HEMA particles by saturating them with the same drug formulation. Interfacial tension measurements were done for successive batches of 0.5 mL of the filtered commercial timolol maleate formulation with a waiting period of 24 hours. The % BAK removal data agrees with the measurements on lab-made formulations. The efficiency of BAK removal was nearly 98.06% for the first batch of filtered timolol solution (0.5 mL) and remain above 96% for the subsequent batches measured. The results from interfacial surface tension measurements validate a 96% selective BAK removal from more than 16 successive batches of 0.5 ml filtered timolol/BAK formulation, which is close to the volume provided in the commercial Sandoz Timolol Maleate formulation.

Although p-HEMA particle systems show a high efficacy of BAK removal, drop-based drug uptake indicates timolol uptake in these particles is as high as 58% for the second drop tested. It is also noted that the drug removal is higher for the $2^{nd}$ day compared to the $1^{st}$ day. When the first day drop is squeezed out, the fresh formulation flows through the packed bed leading to partitioning of the drug into the filter material. Due to the short transit time, the concentration in the eluting drop is not in equilibrium with that in the particles. After the first drop is instilled and the pressure applied on the bottle to squeeze the drop is removed, the vacuum in the bottle sucks the liquid back into the bottle. However the return of liquid to the bottle is not complete before there is relief of the vacuum in the bottle. Thus, residual drug from the particle wetting formulation diffuse over time into the particles. Hence, a large part of the liquid in the $2^{nd}$ drop comes from the packed bed, which had equilibrated with the particles and the drug concentration is lower than the drug in the $1^{st}$ drop. If there was no waiting period during the $1^{st}$ and the $2^{nd}$ drop, for example if patients instills a drop in each eye, the $3^{rd}$ drop would likely be the one with the lowest drug concentration. If the formulation equilibrates with the particles, the final concentration would be $1/(1+K*(1-\varepsilon)/\varepsilon)$ where is a is the liquid fraction in the plug during equilibration and K is the partition coefficient of the drug in the material of the plug. For approximate 50% void fraction, the ratio of the drug concentration I the eluting drop after equilibration may be $1/(1+K)$. So if the outlet concentration is targeted to be within 2% of the formulation concentration, the value of K may be <0.02. If the outlet concentration is targeted to be within 5% of the formulation concentration, the value of K may be <0.05. Similarly, if the outlet concentration is targeted to be within 10% of the formulation concentration, the value of K may be <0.11. It is further noted that this partition coefficient represents the portion of the drug that is adsorbed on the polymer comprising the plug. Any swelling of the material may also lead to drug going into the plug material with the aqueous portion but such uptake may not result in decrease in the concentration outside in the liquid portion of the plug. In this specific example, subsequent samples after the $2^{nd}$ drop show a slow increase in drug concentration eventually reaching negligible drug removal after about 15 days. To establish a consistent drug concentration for the initial dosages, the bottle with the particle plug tip can be inverted for a sufficient period, for example, but not limited to 2-weeks allowing the drug to diffuse into the particles and achieve a nearly drug saturated particle state. The procedure of pre-equilibration with timolol/BAK formulation to saturate the particle matrix with the drug of interest allows for negligible uptake with subsequent doses without compromising the high efficacy of BAK removal.

Due to the high disparity in the partition coefficients of timolol and BAK into a p-HEMA particle matrix an effective approach involves the saturation of the drug into the hydrophilic polymer plug. A 2-week period for pre-equilibration was chosen based on the time scale of diffusion of timolol within the particle matrix. Based on a threshold timolol diffusivity of $1 \times 10-13$ m2/s within the particle phase, the time scale of drug diffusion in particles of an average size of 1 mm is determined to be around 11 days. The uptake of timolol by pre-equilibrated particles was low, with the quantity of timolol uptake being 0.65% for first drop tested. The quantity of timolol uptake is negligible after the fourth drop of the filtered timolol/PBS formulation (0.5%), indicating saturation of p-HEMA particles by the drug solution. UV-spectral measurements validated a low timolol uptake of 4% by pre-equilibrated p-HEMA particles for lab made formulations. The % timolol uptake by p-HEMA particles was assessed for the commercially available 10 mL timolol Maleate ophthalmic solution from Sandoz Inc. The concentration of timolol maleate and BAK in the commercial formulation was 0.5% and 0.01% respectively. Prior to dosing the first drop of filtered commercial timolol solution, the commercial filter bottle packed with ~0.1 g p-HEMA particles in the plug was inverted for 2 weeks to allow pre-equilibration of particles with drug formulation. The quantity of timolol uptake by the pre-equilibrated p-HEMA particles were as high as 22% for the first drop tested, however, subsequent formulation drops tested show decreasing timolol uptake by the particle with timolol uptake being 0.1% for third drop tested and negligible uptake after the fourth drop of the filtered commercial timolol/PBS formulation (0.5%) indicating saturation of p-HEMA particles by the drug solution. The high selectivity of BAK removal with timolol drug pre-equilibration of p-HEMA particles with the drug formulation prior to delivering multiple formulation dosages unfortunately may require a pre-equilibrating the p-HEMA particle system with the drug of interest. The long period of pre-equilibration may be undesirable in drug solution manufacturing.

According to an embodiment of the disclosure, particles were formulated to include at least one hydrophobic monomer to discourage significant uptake of the drug. Particles that would cater to a system of hydrophilic ophthalmic drug formulations used for different treatment procedures and by different subjects are needed. To achieve this goal, t-butyl methacrylate, a hydrophobic monomer, is added along with HEMA to the monomer mixture without further altering the composition of the batch used for the preparation of p-HEMA particles where the ratio of tert-butyl methacrylate and HEMA in the monomer mixture was adjusted to minimize drug uptake also retain high partition coefficient of the system used to obtain high BAK removal rates.

Figure 8:
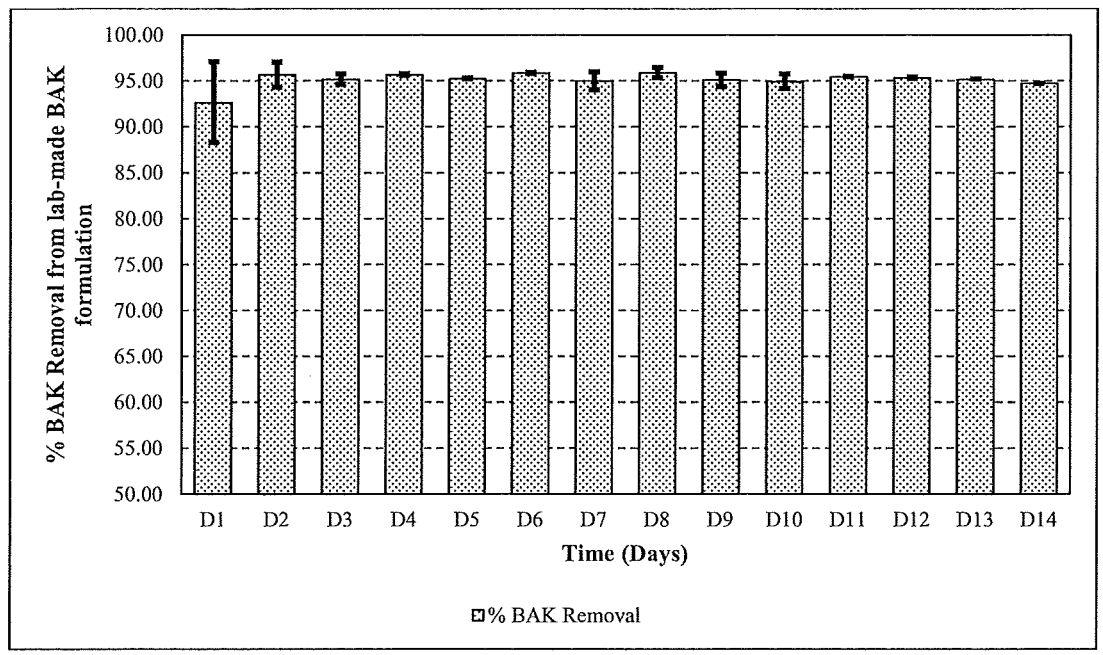
FIG. 8 is a bar chart for the percentage BAK removal after passing a 0.5 ml of (0.5%) Timolol/(0.01%) BAK solution through the packed p-HEMA (25 v/v %)/Tert-Butyl Methacrylate (75 v/v %) particles synthesized with SR9035 as cross linker, according to an embodiment of the disclosure.

The particles according to embodiments of the disclosure may be synthesized by UV curing a batch of, for example, 25 (v/v %) HEMA monomer and 75 (v/v %) tert-butyl methacrylate monomer. FIG. 8 shows the fractional removal of BAK from multiple batches of 0.5 ml of the filtered timolol/BAK formulation. The % BAK removal data indicate that p-HEMA/tert-butyl methacrylate particles, according to an embodiment of the disclosure, are as efficient as their p-HEMA counterpart for selective removal of preservative from ophthalmic formulations.

To enhance the accuracy of % BAK removal determinations, equilibrium surface tension of PBS solution is pushed through a control filter with ~0.070 g p-HEMA/tert-butyl methacrylate filter is monitored along with the surface tension measurements of the filtered drug formulation. The difference in measured equilibrium surface tension between pure PBS solution and PBS-dosed from the filter packed with p-HEMA/tert-butyl methacrylate particles can be attributed to impurities leached out of the particle matrix. Hence, surface tension of PBS-dosed from the filter with packed particles is used as reference for evaluation of % BAK removal from the drug formulation. The degree of BAK removal is nearly 98.04% for the fourth aliquot of filtered solution (0.5 mL) and remains above 96% for the subsequent batches measured. The results from interfacial surface tension measurements show a 96% selective BAK removal from more than 14 successive aliquots of 0.5 ml filtered timolol/BAK formulation, indicating that that the particles, according to an embodiment of the disclosure can be integrated into the commercially available eye drop filter bottles.

Figure 9:
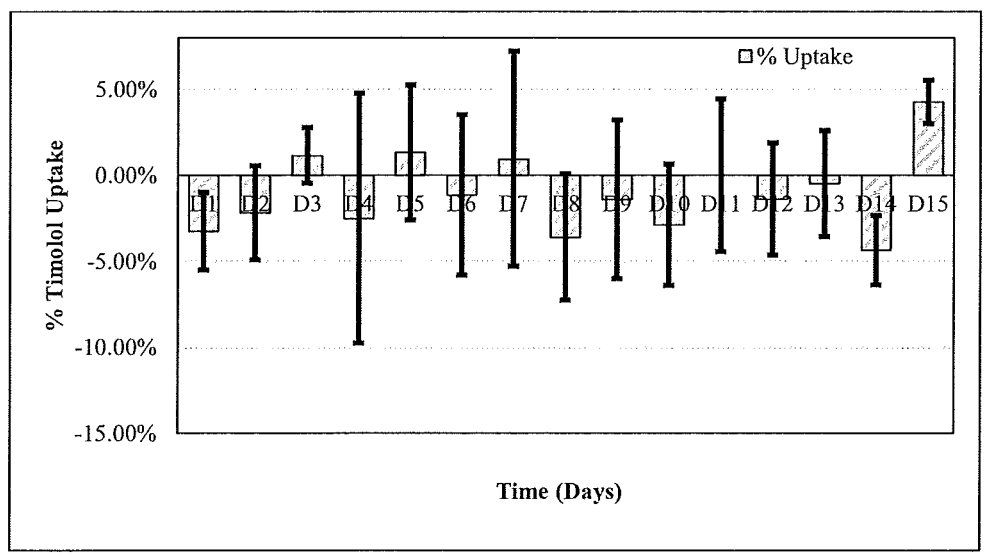
FIG. 9 is a bar chart of Timolol uptake based on passing approximately 30 μL of lab-made (0.5%) Timolol/(0.01%) BAK solution through the packed p-HEMA/Tert-Butyl Methacrylate particles, according to an embodiment of the disclosure, that are synthesized using SR9035 as a cross linker over 15 days, where the 30 μL Timolol formulation drops were diluted 100-fold to obtained UV-spectra of the formulation.

FIG. 9 is a plot of the degree of timolol uptake as a percentage from approximately 30 μL of the filtered timolol formulation by filter plugs packed with approximately 0.07 g of p-HEMA (25 v/v %)/tert-butyl methacrylate (75 v/v %) particles, according to an embodiment of the disclosure. The degree of timolol uptake by these particles were negligible for the cumulative filtered aliquots (15 drops ~0.45 ml) tested. UV-spectral measurements indicated the presence of >99% retention of timolol in the filtered drug formulation showing no signs of uptake by the p-HEMA/tert-butyl methacrylate particles for more than 15 drop aliquots removed daily over 15 days.

Figure 26:
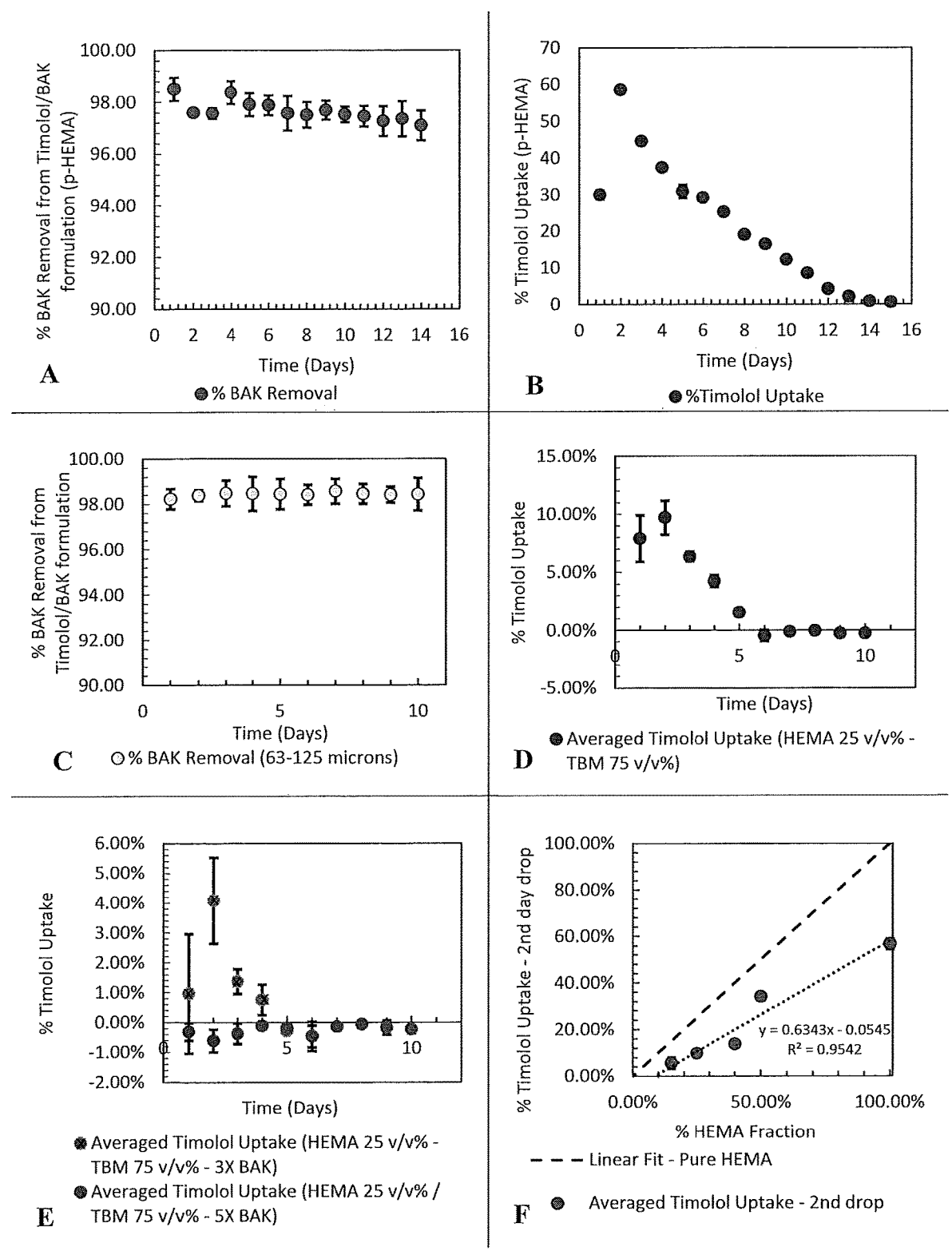
FIG. 26 shows A: Fractional BAK removal and B: fractional drug uptake from Timolol/BAK formulation from p-HEMA filters. C: Fractional BAK removal and D: fractional drug uptake from Timolol/BAK formulation from 25 v/v % HEMA/75 v/v % TBM filters. E: Improved drug uptake rates of Timolol in 25 v/v % HEMA/75 v/v % TBM filters pre-loaded with 3× and 5×BAK. F: Relationship between % Timolol uptake from the second formulation drop dosed versus % HEMA content in the polymer matrix.

FIG. 26A shows the % of BAK removed determined by using the measured equilibrium interfacial surface tension of filtered 0.5 wt. % timolol formulation containing 0.01 wt. % (100 ppm) BAK, 14 batches of 0.5 ml of the filtered formulation was monitored daily in succession. Similar experiments were done with 0.01 wt. % RAK/PRS as an aqueous phase (without Timolol—data not shown). As expected, the results of measurements on the filtered formulation show an increase in interfacial surface tension of the aqueous timolol/BAK solution validating the removal of BAK from the formulation. A stark difference in interfacial tension values of 0.01 wt. % BAK calibration solution and the filtered formulation indicate at least 1 or higher log reduction of BAK concentration in the filtered aliquot dosed and validates a high partition coefficient of BAK in the p-HEMA particle matrix.

FIG. 26B shows the corresponding percentage of BAK removed from multiple 0.5 mL batches of the filtered timolol/BAK formulation. The % BAK removal data indicate that p-HEMA particles are candidates for selective removal of preservative from ophthalmic formulations. The rate of BAK removal was nearly 98.5% for the first batch of filtered solution (0.5 mL) and remain above 96% for the subsequent batches measured. Interfacial surface tension measurements indicate that more than 95% BAK is selectively removed from more than 30 successive batches of 0.5 mL filtered timolol/BAK formulation (data shown for 14 days), thus showing no sign of saturation of p-HEMA particles with BAK. With interfacial tension measurements validating high efficacy of BAK removal by p-HEMA particles for lab made formulations, our next approach was to demonstrate the same for commercial timolol formulations that are available in the market. The % BAK removal data was in agreement with the measurements on lab-made formulations (FIG. 26A). This result further validates the high performance for selective removal of BAK from ophthalmic formulations and demonstrates the ease of integrating p-HEMA particles into pre-existing multi-dose commercial eye drop bottles. FIG. 26B shows the % of drug removed from the eluding drop when the timolol+BAK formulation was filtered. Although p-HEMA particle systems show a high efficacy of BAK removal, drop-based drug uptake study presented in FIG. 26B indicates the rate of timolol uptake in these particles to be as high as 58% for the second drop tested. It is also noted that the drug removal is higher for the 2nd day compared to the 1st day. When the first day drop is squeezed out, the fresh formulation flows through the packed bed leading to partitioning of the drug into the filter material. Due to the short transit time, the concentration in the eluting drop is not in equilibrium with that in the particles. After the first drop is instilled and the pressure applied on the bottle to squeeze the drop is removed, there is vacuum in the bottle due to which liquid in the packed bed may be sucked back in. It is however likely that liquid may be sucked back from only the large channels which may then allow an air channel to form relieving the vacuum. Thus, in the 24 hours in between the 1st and the 2nd drop, the drug from the formulation in the packed bed continues to diffuse into the particles. When the 2nd drop is instilled, a large part of the liquid in the drop came from the packed bed, which had equilibrated with the particles, and so the drug concentration is lower than that in the 1st drop. Subsequent samples show a slow increase in drug concentration eventually reaching a negligible drug removal after about 15 days. Although our design showed a high efficacy of BAK removal, it was essential to address the drawback of pre-equilibration of p-HEMA particles with the drug formulation prior delivering multiple formulation dosages. Though pre-equilibrating the p-HEMA particle system with the drug of interest addresses the issue of high drug uptake, long pre-equilibration durations of 2 or more weeks may be undesirable in manufacturing. Further, stringent FDA guidelines on ophthalmic formulations limits drug loss on a drop by drop basis to <0.1%. The approach adopted to resolving this issue was to formulate particle systems with an additional hydrophobic monomer to avoid significant uptake of the drug. This technique may eliminate the additional procedure of particle pre-equilibration without compromising the effectiveness of BAK removal. TBM was chosen as the hydrophobic monomer and different compositions of HEMA/TBM were prepared.

FIG. 26C and FIG. 26D show the % BAK removal and the corresponding uptake of Timolol by filter packed with p-HEMA (25%)/TBM (75%). The rate of BAK removal is unaffected and is nearly 98.04% for the fourth batch of filtered solution (0.5 mL) and remain above 96% for the subsequent batches measured. The results from interfacial surface tension measurements validate a 96% selective BAK removal from more than 14 successive batches of 0.5 mL filtered timolol/BAK formulation, showing promise of an efficient design that could be integrated into the commercially available eye drop filter bottles. It should be noted that the particle systems were not hydrated by a 10 mL PBS pass for additional cleaning. A 10% drug was noticed in the second drops dosed. Six batches of 0.5 g of p-HEMA particle matrices was pre-loaded with BAK concentrations ranging from 0.3 mg/mL-2 mg/mL, i.e., 3 to 10-fold higher than the regulated concentration limit of BAK in commercial formulation. A 48-hour pre-equilibration duration allotted for soaking the p-HEMA particle matrix in 0.02 mg/ml BAK/PBS solution medium based on the dynamic concentration data recorded for partition coefficient estimation in these particles. The technique was proposed based on the speculation of charge-charge repulsion between BAK, a cationic surfactant loaded in p-HEMA/tert-butyl methacrylate particle matrix and the hydrophilic drug formulations like timolol and brimonidine in PBS, whose charge is positive at physiological pH of 7.4. The preloaded BAK present near the particle surface contributes to a potential screening of timolol and brimonidine formulation, thereby reducing drug uptake. For particle systems with partition coefficients >100, equation 1 can be approximated as $$K = \frac{C_{p,f}}{C_{w,f}} \cong \frac{V_w C_{w,i}}{V_p C_{w,f}} \qquad \text{(Equation 9)}$$

$$C_{p,f} \cong \frac{V_w C_{w,i}}{V_p}. \qquad \text{(Equation 10)}$$

Since the mass of BAK in the aqueous phase at equilibrium is negligible for particle systems with a high BAK partition coefficient, this approximation is valid. The volume ratio between the concentrated BAK loading solution and the p-HEMA/tert-butyl particle matrix is potentially advantageous for the procedure of pre-loading particles with BAK prior employing them for selective preservative removal or drug uptake studies. Since the calculated partition coefficient of p-HEMA particles is ~400, it allows implementation of this simple yet effective pre-loading procedure and does not compromise the high efficacy of BAK removal by pre-loaded p-HEMA particle matrix. Based on the simple approximation given by equation 14 and assuming the particle density to be around 1 g/cc, 1 g of p-HEMA particles soaked in 15 mL of 0.02 mg/mL BAK/PBS solution till equilibration would yield a 0.3 mg/mL BAK pre-loading (i.e., 3-fold times higher than the regulated concentration limit of BAK in commercial formulation) in these particles. A similar protocol was adopted to pre-load the particles with a higher concentration of BAK by fixing the BAK loading solution concentration of 0.02 mg/mL and changing the volume ratio of loading solution and the particles. The 25/75 p-HEMA/TBM BAK pre-loaded particles show <4% timolol uptake without any compromise in BAK removal performance of the filter material (FIG. 26E). The uptake of timolol was also quantified as a function of % HEMA fraction in the synthesized particle matrix (FIG. 26F). It is observed that BAK preferentially binds more with HEMA fraction in the particle matrix. A summary of formulations for timolol is summarized in Table 2.

TABLE 2

Summary of formulations for Timolol Maleate.

| Drug Formulation | Particle Formulation | Size Fraction of particles | Cross-linker | Polymerization method | Pre-loaded BAK Concentration (mg/mL) | Drug Partition Coefficient | BAK Partition Coefficient | % Drug in the dosed drop |
|---|---|---|---|---|---|---|---|---|
| 5 mg/mL of Timolol Maleate | 25%/75%-HEMA/TBM | (63-125 μm) | SR9035 | UV | 0.3 (3X) | 0.086 | 159 | 92.149% |
| | 25%/75%-HEMA/TBM | (63-125 μm) | SR9035 | UV | 0.5 (5X) | <0.04 | 159 | 100.00% |
| | 15%/85%-HEMA/TBM | (63-125 μm) | SR9035 | UV | 0.3 (3X) | <0.04 | 143 | 100% |
| | 10%/90%-HEMA/TBM | (63-125 μm) | SR9035 | UV | 0 (0X) | <0.04 | 64.76 | 100% |
| | 5%/95%-MAA/TBM | Mixed | SR9035 | UV | 0 (0X) | 0.0563 | 237.05 | 94.67% |
| | 1TC8020938 25%/75%-HEMA/TBM | (63-125 μm) | SR9035 | UV | 0 (0X) | <0.04 | 165 | 100.00% |
| | 1TC18041759 25%/75%-HEMA/TBM | (63-125 μm) | KPS | Thermal | 0 (0X) | 0.204 | 225 | 82.75% |
| | 1TC18050769 25%/75%-HEMA/TBM | (63-125 μm) | KPS | Thermal | 0 (0X) | 0.34 | 540 | 63.45% |

Preservative Removal and Drug Uptake Studies—Levofloxacin, Dorzolamide and Brimonidine Formulations Levofloxacin is an oral fluoroquinolone and an antibacterial agent prescribed as a preoperative and postoperative medication to control infections after eye surgery. Dorzolamide Hydrochloride is a potent water-soluble inhibitor of human carbonic anhydrase isoenzymes prescribed for use by patients with ocular hypertension or open-angle glaucoma. It acts as an anti-glaucoma agent by decreasing the aqueous humor inflow, thereby lowering the IOP and improving blood flow to the retina and optic nerve. Though clinical studies have demonstrated the safety and tolerability profile of both commercial levofloxacin and dorzolamide medications, there are reported incidences of common side effects including peripheral nerve damage, severe eye irritation, and visual discomfort due to enhanced light sensitivity. PRK surgery is a refractive procedure where the patent receives a bandage contact lens (BCL) for faster corneal re-epithelialization. PRK patients are prescribed Levofloxacin as a medication. Although, epithelial healing takes around 2-4 days with a BCL, a topical antibiotic like Levaquin (levofloxacin) is administered after healing to prevent ocular epithelial infections, reduce pain, and reduce ocular discomfort. Most commercial antibiotics, including Levofloxacin, contain added preservatives, such as like BAK. Patients who may require a frequent dosage of such medications are likely to encounter epithelial cell and tissue damage.

Glaucomatous patients with a severe affliction are often recommended frequent topical dorzolamide administration for managing symptoms. The frequency of drop administration in such cases may vary from 2 to as many as 4 times a day, thereby enhancing the chances of epithelial cell damage due to high BAK exposure. BAK induced allergies coupled with these side effects due to prolonged use of topical medications profoundly impacts the benefits of Glaucoma treatment. Thus, there is a need for preservative-free antibiotics and anti-glaucoma medications to lessen the chances of post-operative and preservative-induced infections accompanied by no or less adverse side-effects. Levofloxacin and dorzolamide are hydrophilic in nature, and p-HEMA/Tert-Butyl methacrylate particles can be employed as filter materials to achieve selective preservative removal during dosing.

Aqueous concentrations of levofloxacin and dorzolamide in PBS examined with 5 mg/ml (0.5%) and 20 mg/ml (2%), respectively, with 0.1 mg/ml of BAK showed consistent % BAK removal, indicating that p-HEMA/Tert-Butyl Methacrylate particles are suitable systems for all three hydrophilic medications including Timolol, Dorzolamide, and Levofloxacin. Timolol, Levofloxacin, and Dorzolamide are surface-inactive components, such that measured interfacial tension data are accurate and reliable for two-component formulations involving BAK as preservative. The magnitude of BAK removal, >95%, is a high BAK partition into these particles, which are small in size (<1 mm and >0.5 mm) relative to p-HEMA particles. Results from interfacial surface tension measurements indicate a 96% selective BAK removal in each aliquot over 14 successive 0.5 ml batches of both levofloxacin/BAK and dorzolamide/BAK formulations.

Figure 10:
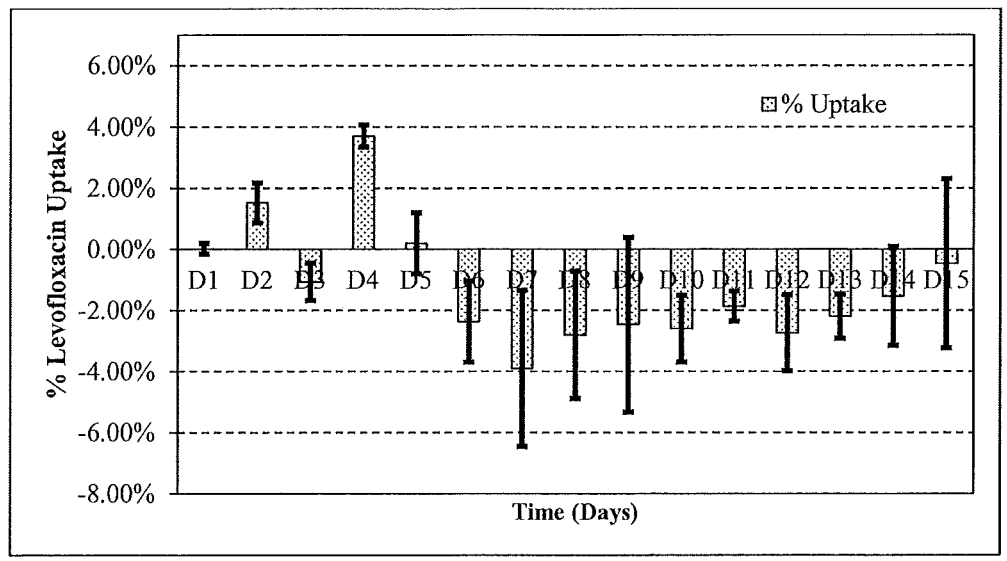
FIG. 10 is a bar chart of Levofloxacin uptake based on passing approximately 30 μL, of lab-made (0.5%) Levofloxacin/(0.01%) BAK solution through the packed p-HEMA/Tert-Butyl Methacrylate particles, according to an embodiment of the disclosure, synthesized using SR9035 as cross linker over 15 days, where the 30 μL Levofloxacin formulation drops were diluted 100-fold to obtained UV-spectra of the formulation.
Figure 11:
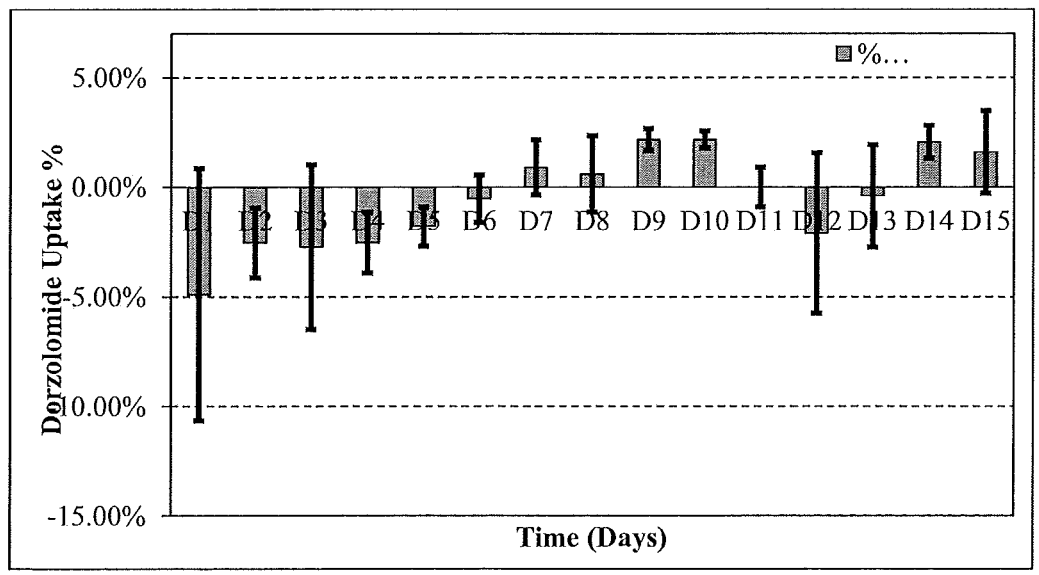
FIG. 11 is a bar chart of Dorzolamide uptake based on passing approximately 30 μL of lab-made (2%) Dorzolamide/(0.01%) BAK solution through the packed p-HEMA/Tert-Butyl Methacrylate particles, according to an embodiment of the disclosure, synthesized using SR9035 as cross linker over 15 days, where 30 μL Levofloxacin formulation drops were diluted 300-fold to obtained UV-spectra of the formulation.

FIG. 10 and FIG. 11 show the rate of levofloxacin and dorzolamide uptake from approximately 30 μL/day of the filtered Levofloxacin formulation by filters packed with approximately 0.07 g of p-HEMA/tert-butyl methacrylate particles, according to an embodiment of the disclosure. The degree of levofloxacin uptake by these particles is negligible for the cumulative filtered solution (15 drops—0.45 ml) tested. The % drug uptake for levofloxacin and dorzolamide, within an average standard deviation, is 1.31% and 1.86% respectively, illustrating the low partition coefficients of both levofloxacin and dorzolamide into p-HEMA/tert-butyl methacrylate particle matrix. UV-spectral measurements confirm the presence of more than 99% levofloxacin and dorzolamide in the filtered drug aliquots, showing no signs of significant uptake by p-HEMA/tert-butyl methacrylate particles for more than 15 aliquots.

Figure 12:
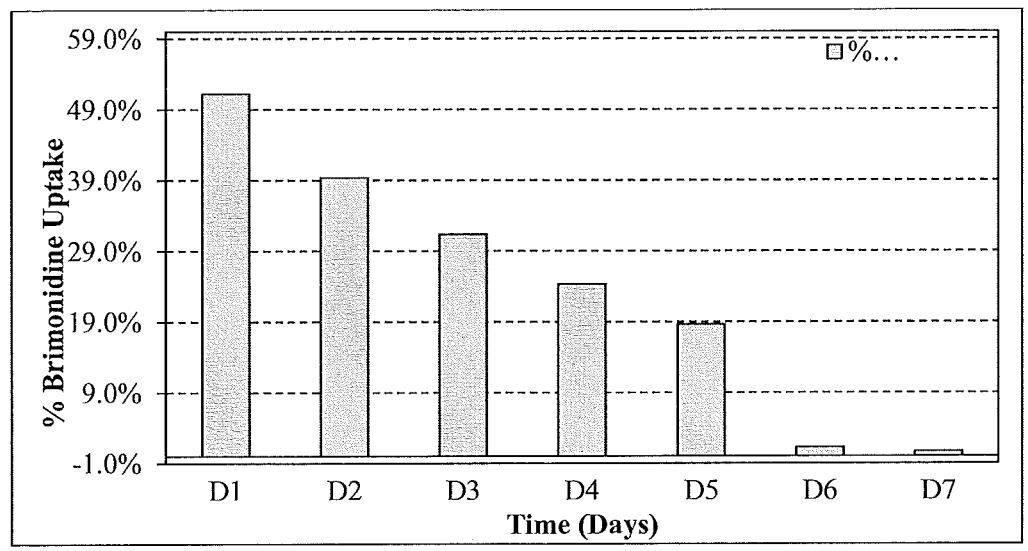
FIG. 12 is a bar chart of Brimonidine uptake profile based on passing approximately 30 μL of lab-made (2%) Brimonidine/(0.01%) BAK solution through the packed p-HEMA/Tert-Butyl Methacrylate particles, according to an embodiment of the disclosure, synthesized with SR9035 as cross linker over 7 days, where the 30 μL Levofloxacin formulation drops were diluted 100-fold to obtained UV-spectra of the formulation.

Brimonidine tartrate, a topical beta-blocker is an effective intraocular pressure lowering agent prescribed for the glaucomatous patient population. As a selective alpha-adrenoreceptor, brimonidine tartrate is a safer alternative to beta-blockers like timolol, whose long-term clinical dosages can compromise cardiovascular and pulmonary functions. Combigan is a second-line therapeutic anti-glaucoma medication containing a fixed combination of 0.2% Brimonidine Tartrate and 0.5% timolol maleate formulations. It is usually prescribed if monotherapy of either timolol or brimonidine does not lower the TOP in patients afflicted by chronic glaucoma sufficiently. Although there is an increased potential of side effects induced by multiple medications, a combinational therapy involving Combigan allows a lower and convenient dosing regimen, thereby reaching the target 10P. Randomized human trials have demonstrated the efficacy of both Brimonidine and Combigan treatment without a notable chronic effect on heart, incidences of common allergic reactions have occurred characterized by follicular conjunctivitis, lid edema, dry mouth, and temporary stinging sensation are still prevalent among Glaucoma subjects. Preservative (BAK) induced allergic manifestations coupled with these adverse effects due to prolonged use of Brimonidine or Combigan therapy profoundly impacts the benefits of Glaucoma treatment, thus necessitating the need for preservative-free glaucoma medications. The efficacy of benzalkonium chloride removal and the quantity of drug absorbed were assessed using a lab-made 0.2% brimonidine tartrate/PBS ophthalmic formulation. The prototype eye drop bottle was filled with drug/PBS solution (i.e., 0.2% brimonidine tartrate/PBS ophthalmic formulation) prior mounting a preservative removing polymer plug, according to an embodiment of the disclosure. The UV spectral measurements of filtered formulation obtained for drop filtered daily were used to determine drug absorption by p-HEMA/TRIS/tert-butyl Methacrylate particles with UV-Vis measurements for high drug concentration in aqueous PBS solution (0.2%), with the filtered aliquots of brimonidine tartrate (0.2%) diluted 100-fold. Although the low partition coefficient of a system of hydrophilic drugs timolol, levofloxacin, and dorzolamide in the HEMA (25 v/v %/tert-butyl methacrylate (75 v/v %) particles, according to an embodiment of the disclosure, restrains the maximum drug uptake rate to less than 5%, that same particle matrix is not compatible with 0.2% brimonidine tartrate ophthalmic formulation. As shown in FIG. 12, brimonidine has a partition coefficient of 1 for the particle systems as indicated by a drug uptake of 51% for the first aliquot tested, based on a 1:1 volume ratio of particles to formulation entrained within the plug. Though the mechanism of interaction between brimonidine and the p-HEMA/tert-butyl methacrylate particle matrix may not be well-understood, it can be speculated that the higher drug uptake estimates can be attributed to interactions between Brimonidine and the hydrophilic p-HEMA fraction present in the particle matrix.

Figure 13:
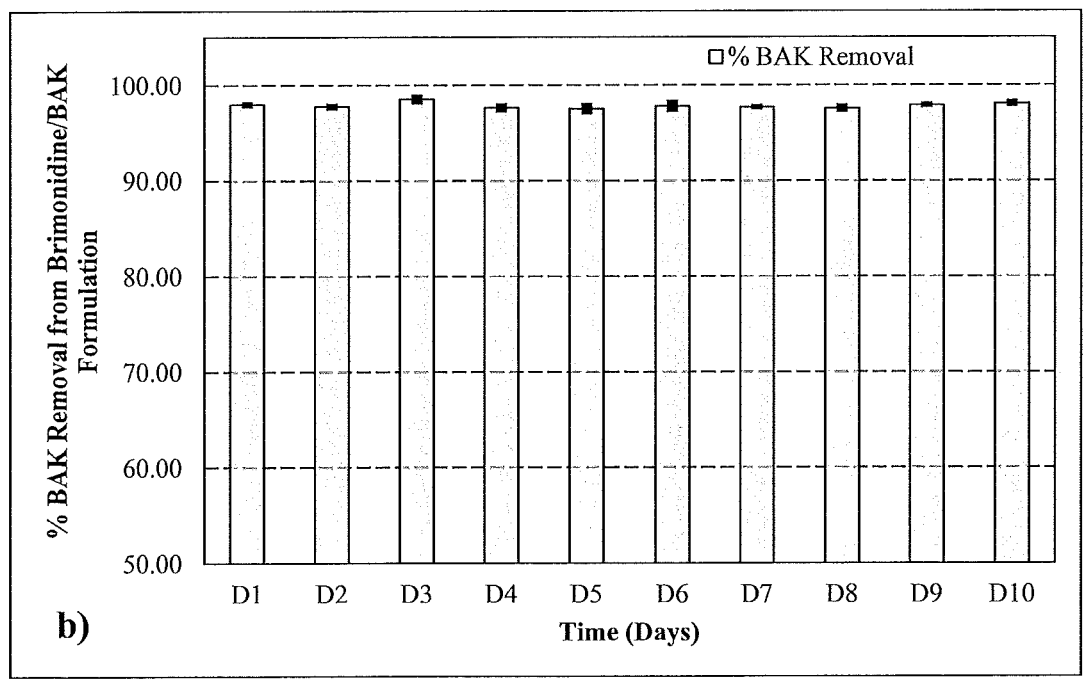
FIG. 13 is a bar chart of BAK removal upon passing 0.5 ml of (0.2%) Brimonidine/(0.01%) BAK solution through the p-HEMA (25 v/v %)/TRIS (37.5 v/v %)/Tert-Butyl Methacrylate (37.5 v/v %) particles synthesized using SR9035 as a cross linker over 10 days.
Figure 14:
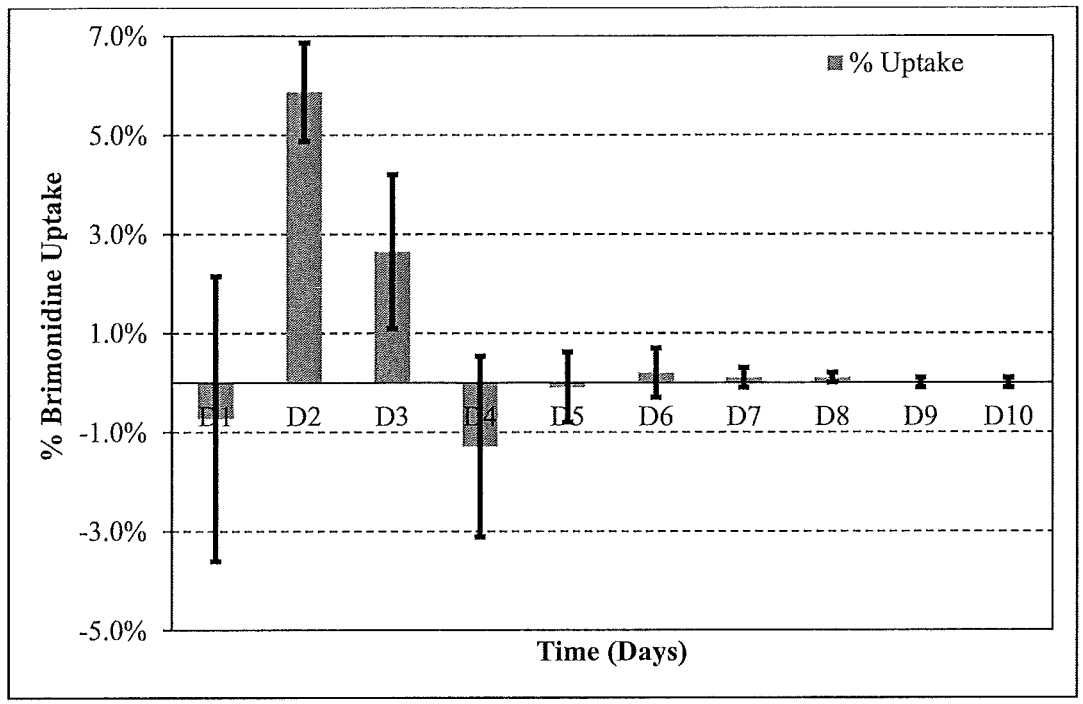
FIG. 14 is a bar chart of Brimonidine uptake profile based on passing approximately 30 μL. of lab-made (2%) Brimonidine/(0.01%) BAK solution through the packed p-HEMA/TRIS/Tert-Butyl Methacrylate particles, according to an embodiment of the disclosure, synthesized using SR9035 as a cross linker over 10 days, where the 30 μL Brimonidine formulation drop was diluted 100-fold to obtained UV-spectra of the formulation.

Without being limited by theory, to reduce this interaction a particle with more hydrophobicity than the HEMA (25 v/v %)/tert-butyl methacrylate (75 v/v %) particles was prepared. Because the partition coefficient and diffusivity of BAK in purely hydrophobic particle systems is lower than their hydrophilic counterpart, a particle matrix with a low affinity for Brimonidine without a compromise on desired constraints of high BAK removal was achieved by introducing units from methacryloxypropyltris(trimethylsiloxy)silane (TRIS), a hydrophobic monomer that is a included in many silicone hydrogels, to the HEMA and tert-butyl methacrylate monomer mixture. Keeping the volume fraction of HEMA fixed in the monomer mixture, the ratio of tert-butyl methacrylate and TRIS was optimized to achieve negligible drug uptake while retaining the high partition coefficient used to obtain high degrees of BAK removal, as indicated in FIG. 13. By UV curing a batch of 25 (v/v %) HEMA monomer, 37.5 (v/v %) TRIS, and 37.5 (v/v %) tert-butyl methacrylate forms the desired preservative removing terpolymer. FIG. 14 shows the uptake of brimonidine in the HEMA/TRIS/tert-butyl methacrylate particles. Although improved, the brimonidine is retained partially in the preservative removing polymer plug for the second and third aliquots.

In another embodiment of the disclosure, the drug uptake and BAK uptake profiles of in lab-made preservative removing copolymer with TRIS and dimethylacrylamide (DMA) were prepared using a composition of 75 (v/v %) TRIS/25 (v/v %) DMA was prepared. The uptake experiments were conducted in the presence of 3.5 mL of 0.12% (1.2 mg/ml) BAK/PBS solution with 100 μm thick copolymer films. Table 3, below, gives a calculated partition coefficient of BAK of greater than 430 in 75% TRIS hydrogels indicating the ability to form a synthetic copolymer particle for selective preservative removal.

TABLE 3

Summary of BAK loading experiments in lab made TRIS/DMA gels. Data are shown for 1 experimental run per loading BAK/PBS concentrated solution.

| BAK loading solution concentration (mg/ml) | Material A<br>75 (v/v %)TRIS/25<br>(v/v %) DMA 1.2 |
|---|---|
| Loaded BAK Content (μg) | 2255 |
| Partition coefficient of BAK (K-BAK) | 449 |
| Number of experiments | 3 |

The p-HEMA/TRIS/tert-butyl methacrylate particle system is suitable for selective preservative removal from 0.2% brimonidine tartrate ophthalmic formulations. For Combigan, a combinational therapy of timolol and brimonidine showed a 15-20% uptake of timolol for the second aliquot filtered through the particle.

According to an embodiment of the disclosure, pre-loading a batch of p-HEMA/tert-butyl methacrylate particle matrix with BAK concentration ranging from 0.3 mg/ml-0.8 mg/ml, which are 3 and 8-fold higher than the regulated concentration limit of BAK in commercial formulation is carried out to form a BAK preloaded preservative removing particle. As can be discerned from Equation 1, above, where partition coefficients are very large, greater than 300, Equation 1 can be approximated as shown in Equation 9 and 10 above.

The volume ratio between concentrated BAK loading solution and the p-HEMA/tert-butyl particle matrix is potentially advantageous to the procedure of pre-loading particles with BAK prior employing them for selective preservative removal or drug uptake studies. Since the calculated partition coefficient of p-HEMA/tert-butyl methacrylate particles is 322.94, it allows implementation of this simple yet effective pre-loading procedure without compromising the high efficacy of BAK removal by pre-loaded p-HEMA/tert-butyl methacrylate particle matrix. Based on the simple approximation given in Equation 9 and assuming particle density to be about 1 g/cc; 1 g of p-HEMA (25 v/v %)/tert-butyl methacrylate (75 v/v %) particles soaked in 15 mL of 0.02 mg/mL BAK/PBS solution, for a period that establishes the partitioning equilibrium, yields a 3×BAK pre-loading, which has a 3-fold higher BAK content within the particles than the regulated concentration limit of BAK in commercial formulations.

Figure 15:
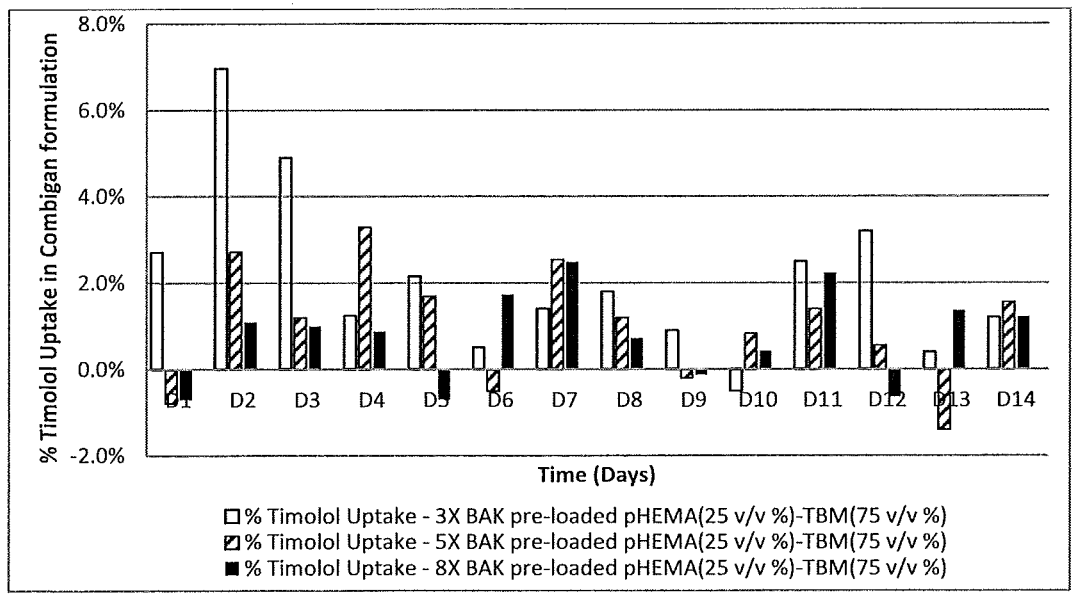
FIG. 15 is a bar chart of Timolol uptake on passing approximately 30 μL of lab-made Combigan formulation (0.2% Brimonidine/0.5% Timolol Maleate and 0.01% BAK solution) through a packed filter with 3.5, and 8 fold BAK treated p-HEMA/TRIS/Tert-Butyl Methacrylate particles synthesized using SR9035 as a cross linker over 10 individual days, where the 30 μL, formulation drop was diluted 100-fold to obtained UV-spectra of the formulation.

BAK removal from Combigan formulation was evaluated in a 30 mL eye drop bottle with a tapered plug, pre-packed with approximately 0.07 g of p-HEMA/tert-butyl methacrylate particles preloaded from a 0.8 mg/ml of BAK/PBS formulation, which establishes a BAK content in the loaded particle matrix that is 8-fold higher than the regulated concentration limit of BAK for commercial ophthalmic formulations. The 8× pre-loaded p-HEMA/tert-butyl methacrylate particles are as efficient as their p-HEMA counterpart for selective removal of preservative from ophthalmic formulations. FIG. 15 shows the removal of Timolol from a Combigan formulation having 0.2% brimonidine, 0.5% timolol Maleate, and 0.01% BAK passed through a packed filter with p-HEMA/TRIS/tert-butyl methacrylate particles, according to an embodiment of the disclosure, where the preservative removing particles were pretreated with 3×, 5×, or 8×BAK solution. The degree of BAK removal is nearly 98.04% through the fourth aliquot and remains above 96% for the subsequent aliquots over two weeks, yet more than 98% of the timolol passed through the preservative removing plug that is pretreated with an 8 fold preloading with BAK.

An eye drop bottle prototype was filled with 5 mL of drug/PBS solution, having 0.2 wt. % brimonidine tartrate in PBS ophthalmic formulation prior to mounting the plug. The UV spectral measurements of filtered formulation were obtained for each filtered drop with a time interval of a day to monitor the drug absorption by 0.1 g of p-HEMA (25 v/v %)/TRIS (37.5 v/v %)/tert-butyl methacrylate (37.5 v/v %) particles. The UV-Vis measurements carried out using a filtered drop of brimonidine tartrate (0.2 wt. %) upon a 100-fold dilution to obtain quantitative measurements. The degree of brimonidine uptake by these particles was 0.2% for the 6 drop tested and less than 6% for every aliquot of filtered solution tested. UV-spectral measurements indicated the presence of more than 99% brimonidine in the filtered drug formulation, showing no signs of uptake by p-HEMA (25 v/v %)/TRIS (37.5 v/v %)/tert-butyl methacrylate (37.5 v/v %) particles. The timolol and brimonidine uptake from approximately 30 μL filtered Combigan aliquots through 0.07 g of p-HEMA/tert-butyl methacrylate particle matrix that were pre-loading with BAK at concentrations ranging from 0.3 mg/mL-0.8 mg/mL, which is 3 to 8-fold of the regulated concentration limit of BAK in commercial formulation. The concentration of timolol and brimonidine in the filtered formulation were determined through a two-parameter least square curve fit method between the measured and reference calibration spectra of both the drugs. MATLAB's fminsearch module was used to deduce optimal values of drug concentration in the filtered solution. The degree of brimonidine and timolol uptake by particles pre-loaded with 0.8 mg/mL BAK were in the range of 1-2% for every aliquot of filtered solution. The pre-loaded particle matrix with higher BAK concentrations, show a lower brimonidine and timolol uptake.

Figure 27:
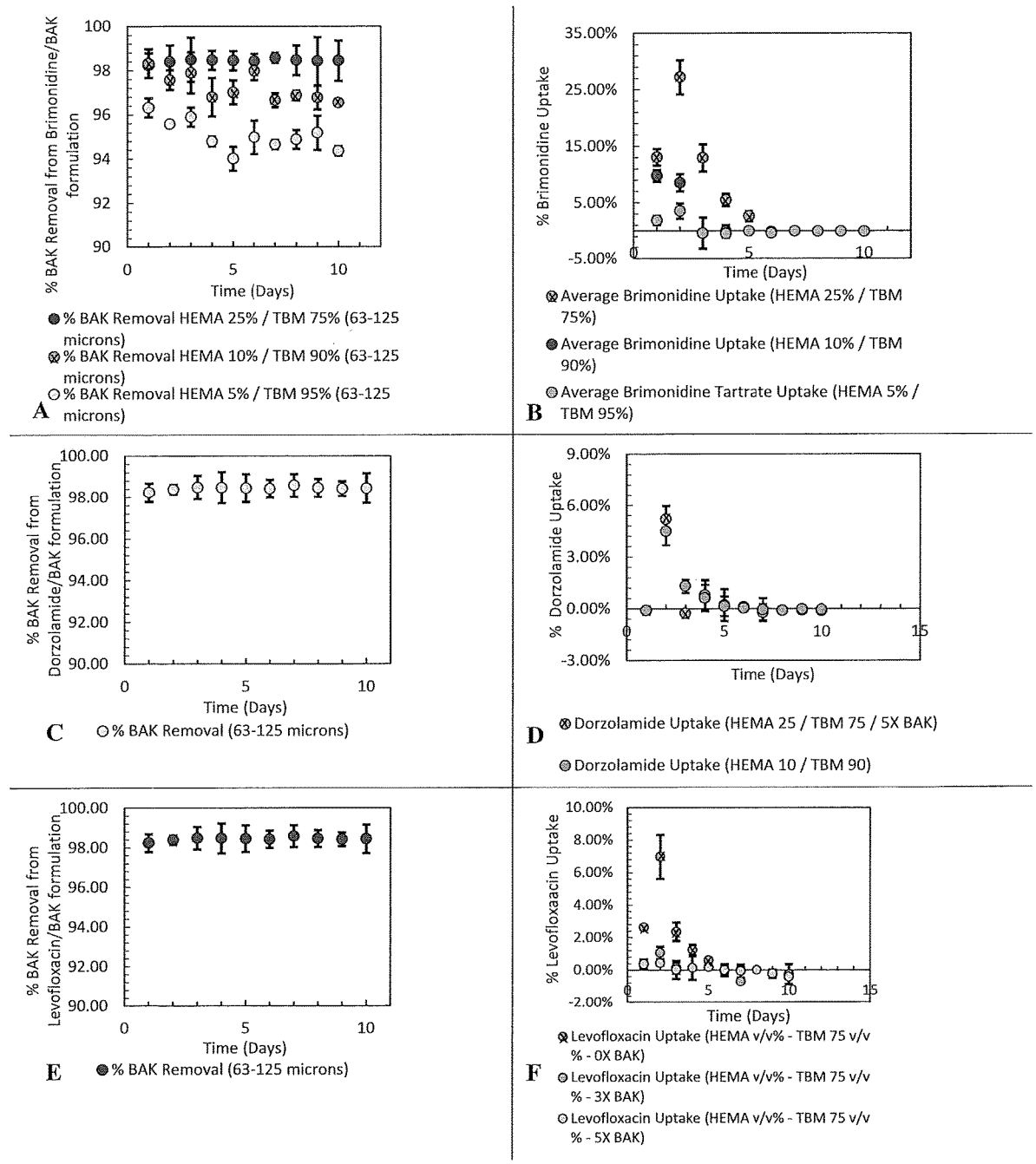
FIG. 27 shows a) Fractional BAK removal and drug uptake (b) from Brimonidine/BAK formulation from different compositions of p-HEMA/TBM filters. c) Fractional BAK removal and drug uptake (d) from Dorzolamide/BAK formulation from 25 v/v % HEMA/75 v/v % TBM and 10 v/v % HEMA/90 v/v % TBM filters. e) Fractional BAK removal from Levofloxacin/BAK formulation from 25 v/v % HEMA/75 v/v % TBM filters. f) Improved drug uptake rates of Levofloxacin in 25 v/v % HEMA/75 v/v % TBM filters pre-loaded with 3× and 5×BAK.

FIG. 27A, FIG. 27C, and FIG. 27E show the fractional removal of BAK from multiple 0.5 mL batches of both filtered brimonidine/BAK, dorzolamide/BAK formulations and levofloxacin/BAK solutions. The aqueous concentrations of levofloxacin and dorzolamide in PBS used for this study were 5 mg/mL (0.5 wt. %) and 20 mg/ml (2 wt. %) respectively along with 0.1 mg/mL of added BAK in the formulations. Consistent % BAK removal data indicate that p-HEMA/tert-butyl methacrylate particles are suitable systems for all three hydrophilic medications including brimonidine, dorzolamide, and levofloxacin. Further, the magnitude of BAK removal rates >95% validates high BAK partition of BAK in these particles systems putting them on a par with their p-HEMA counterpart. An additional characteristic feature of these particles is their smaller size (<125 μm) in comparison to the p-HEMA aggregates. This feature is beneficial for obtaining higher BAK removal rates from the drug/BAK formulations due to an increase in the contact time of aqueous solution with the filter bed without a compromise in optimum hydraulic permeability of the packed bed system. The rate of BAK removal was nearly 98.04% for the fourth batch of filtered solution (0.5 mL) and remain above 96% for the subsequent batches measured. The results from interfacial surface tension measurements validate a 96% selective BAK removal from more than 14 successive 0.5 mL batches of both levofloxacin/BAK and dorzolamide/BAK formulations, showing promise of an efficient design that could be integrated into the commercially available eye drop filter bottles.

The rate of levofloxacin and dorzolamide uptake by the 25% p-HEMA/75% TBM particles was in the range of 3-8% for the second filtered drop and negligible for the next 15 drops tested (FIG. 27I) and FIG. 27F). Pre-loading these particles with BAK concentration of 0.5 mg/ml screens potential drug binding and reduces levofloxacin uptake to <2% and dorzolamide uptake to <6%. The % drug uptake data for both levofloxacin and dorzolamide within an average standard deviation of 1.31% and 1.86% respectively, validate the low partition coefficient estimates of both levofloxacin and dorzolamide in p-HEMA/tert-butyl particle matrix. The rate of levofloxacin and dorzolamide uptake by these particles were as low as 1.52% for the 2nd drop tested for levofloxacin 0.60% for the 8th drop tested for levofloxacin and dorzolamide respectively. Inconsistencies in estimates of levofloxacin and dorzolamide uptake % indicate minor errors involved in a 100-fold dilution of the filtered drug formulation. For brimonidine (FIG. 27B), three p-HEMA/TBM compositions (25/75, 10/90, and 5/95) were tested. Though, 10/90 and 5/95 HEMA/TBM batches reduce the drug uptake to <8%, partition coefficients of <100 for these systems might reduce the capacity of filter to screen >95% BAK. Table 4 summarizes the status of formulations for brimonidine showing <15% uptake. The replacement of SR9035 cross linker with EGDMA does result in a 25% reduction in Brimonidine uptake. Pre-loading particles of this composition is to be tested.

TABLE 4

Summary formulations for Brimonidine Tartrate.

| Drug Formulation | Particle Formulation | Size Fraction of particles | Cross-linker | Pre-loaded BAK Concentration (mg/mL) | Day | Avg. Conc. (mg/mL) | Avg. % Drug | Std. dev |
|---|---|---|---|---|---|---|---|---|
| 2 mg/mL of Brimonidine Tartrate | 15%/85%-HEMA/TBM | Mixed | SR9035 | 0.3 (3X) | Day 2 | 1.755 | 87.77% | 6.36% |
| | 15%/85%-HEMA/TBM | Mixed | SR9035 | 0.5 (5X) | Day 2 | 1.686 | 84.30% | 0.85% |
| | 10%/90%-HEMA/TBM | 125-250 μm | SR9035 | 0 (0X) | Day 2 | 1.828 | 91.40% | 2.05% |

TABLE 4-continued

Summary formulations for Brimonidine Tartrate.

| Drug Formulation | Particle Formulation | Size Fraction of particles | Cross-linker | Pre-loaded BAK Concentration (mg/mL) | Day | Avg. Conc. (mg/mL) | Avg. % Drug | Std. dev |
|---|---|---|---|---|---|---|---|---|
| | 25%/75%-HEMA/TBM | 63-125 μm | EGDMA | 0 (0X) | Day 2 | 1.9 | 95% | 1% |

Preservative Removal and Drug Uptake Studies from Visine Dry Eye Formulation

Dry eye syndrome or Keratoconjunctivitis Sicca (KCS) is a tear film disorder which occurs due to tear deficiency or excessive tear evaporation. The common symptoms of patients afflicted include inflammation of the ocular interpalpebral surface and visual discomfort. The application of ophthalmic lubricant drops is a commonly recommended procedure to mitigate irritation due to inflammation of ocular surface and lacrimal glands. A commercially available ophthalmic lubricant used for treating the signs and symptoms of dry eye condition is the Visine® dry eye relief ophthalmic lubricant drops. Visine® dry eye drops help maintain a stable tear film and homeostasis of the ocular surface with minimal or no compromise in visual acuity and comfort upon administration. Since the frequency of lubricant drop application depends on the severity of the condition, a patient with severe affliction due to dry eye syndrome can be recommended frequent topical administration for managing the symptoms. In such a scenario, an increase in ocular damage due to enhanced BAK interaction with the corneal epithelium is likely, which is particularly potentially advantageous for patients with chronic dry eye syndrome. The % BAK removal was assessed for the commercially available 15 mL Visine® dry eye relief ophthalmic solution from Johnson & Johnson Inc. in this test study. Visine® dry relief eye drops are commonly lubricating saline drops containing biocompatible viscosity enhancers including Hypromellose and Polyethylene Glycol 400. These viscous ingredients provide a dual benefit in the dry eye treatment including moisturizing the tear film as well as minimizing the rate of tear film evaporation in dry eye subjects. A primary issue to be addressed in our eye drop bottle design is the increase in magnitude of applied pressure for drop administration because of enhanced viscosity of the commercial formulation. Low hydraulic permeability of viscous lubricant drops in particle packed filters can be a potentially advantageous issue for elderly patients with chronic dry eye ailments, leading to reduced patient compliance. The permeability constraint is resolved by employing large sized p-HEMA matrix particle that are about 2 mm aggregates. These 2 min aggregates were synthesized in the same manner used for smaller particles but with a lower compression force on the pestle while grinding in the mortar.

Figure 16:
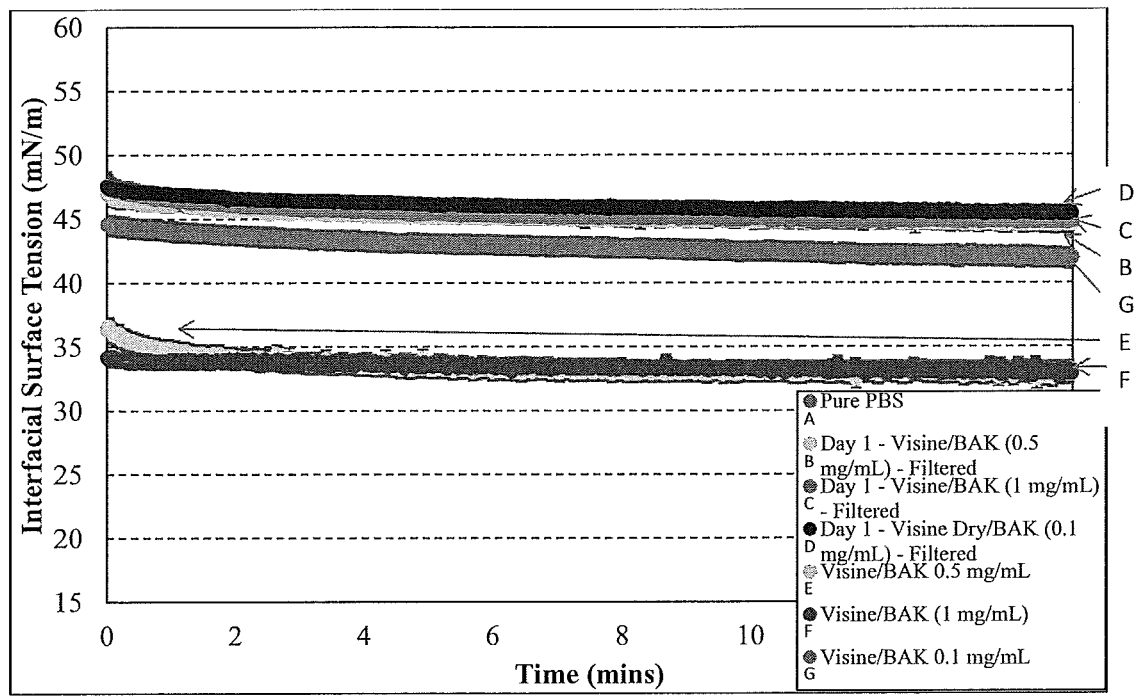
FIG. 16 shows a plot of the dynamic interfacial tension of 0.5 mL of filtered through a plug of p-HEMA and re-filtered Visine®-BAK-air interface as a function of BAK concentration in PBS as an aqueous phase where the concentration of BAK/PBS formulations explored for interfacial tension measurements range from 0.1 mg/ml to 1 mg/ml and with interfacial tension data is presented as 'mean±σ' with n=1 per calibration solution.

The commercial Visine® dry eye relief formulation contains 0.2% Glycerin, 0.2% Hypromellose, 1% Polyethylene Glycol 400, and PEG-400 as surface active ingredients in addition to the preservative benzalkonium chloride. The presence of these additional surface active ingredients pose an obstacle in accurately quantifying the fractional BAK removed from the formulation. To resolve this difficulty, the concentration of BAK was increased in the commercial formulation and conduct Interfacial measurements on Visine® dry eye formulations with BAK concentrations of 0.1 mg/ml, 0.5 mg/ml, and 1 mg/ml respectively were conducted to quantify high BAK removal rates by a p-HEMA filter. FIG. 16 shows a comparison between dynamic interfacial tension measurements of commercial Visine® formulation with BAK concentrations of 0.1 mg/ml, 0.5 mg/ml, and 1 mg/ml, respectively, and their filtered counterpart measured as a function of time. The differential static interfacial tension ~15 mN/m between the control and the filtered formulation obtained for Visine® formulation with higher BAK concentration indicates a high BAK removal rate by p-HEMA particle matrix. From the perspective of high BAK partition coefficient in p-HEMA matrix and a 1:1 volume ratio of particles to formulation entrained within the plug, the concentration of filtered BAK formulation is estimated to be less than 0.002 mg/ml for a formulation whose BAK content is 10-fold higher than the regulated concentration limit of BAK in commercial formulation.

Figure 17:
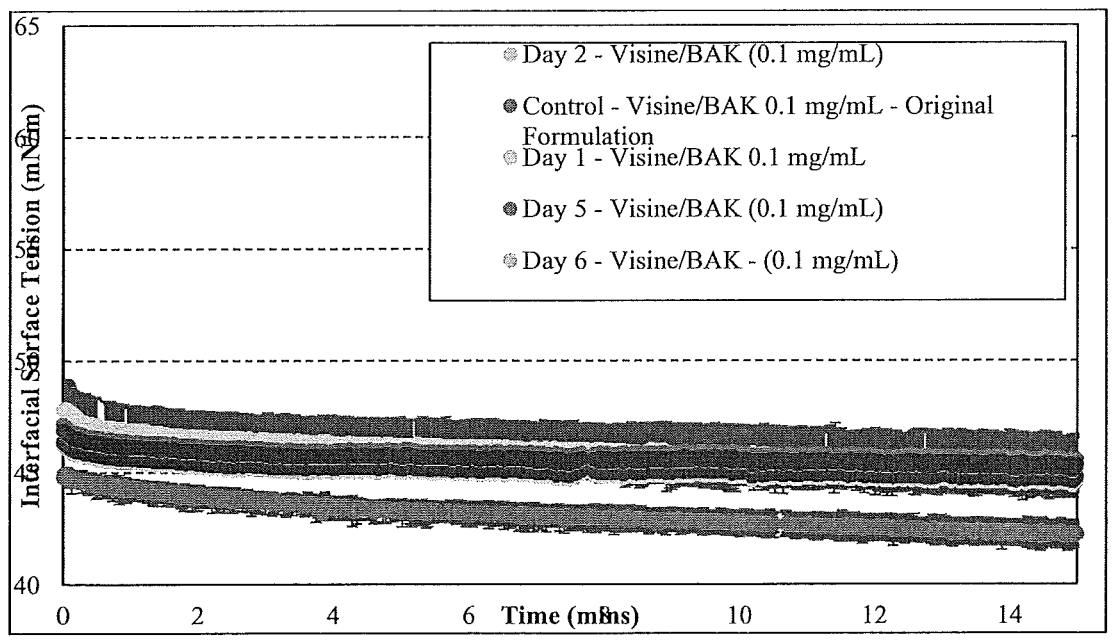
FIG. 17 shows a plot of the dynamic interfacial tension of 0.5 mL BAK-air interface as a function of BAK concentration in PBS as an aqueous phase. The concentration of BAK/PBS formulations explored for interfacial tension measurements range from 0.002 mg/ml to 2 mg/ml. Interfacial tension data is presented as 'mean±σ' with n=1 per calibration solution.
Figure 18:
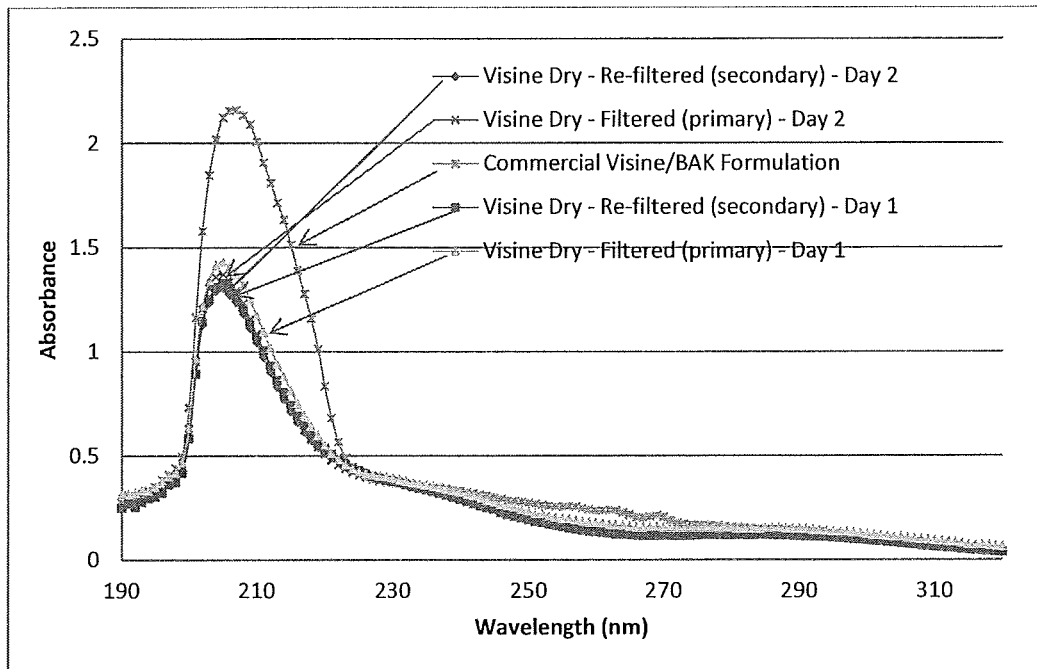
FIG. 18 shows UV spectra data for commercial, filtered and, re-filtered Visine formulation based on dosing a 300 μL (~10 drops) of commercial Visine®/(0.01%) BAK solution filtered through packed p-HEMA particles synthesized using SR9035 as a cross linker.

This rationale can be validated by measuring and comparing the dynamic surface tension of Visine® formulation with a higher BAK content to that of a formulation with a lower BAK concentration. A direct result of this comparison would indicate an overlap of dynamic surface tension curves for Visine® formulations whose initial concentration prior filtering were in the range of 0.1-1 mg/ml. FIG. 16 shows a coincidence of dynamic interfacial tension curves of filtered Visine® formulation within a standard deviation of ~1 mN/m. A secondary approach to substantiate the claim of high BAK removal efficacy was the addition of cumulative drops of Visine®/0.5 mg/ml BAK formulation to the filtered formulation to confirm a decrease in the equilibrium interfacial tension of the concentrated formulation. An overlap of dynamic surface tension data as shown in FIG. 17 for multiple 0.3 ml aliquots of filtered Visine®/BAK formulation confirming high BAK removal by p-HEMA filters. FIG. 18 plots the high removal of BAK from multiple 0.3 ml aliquots filtered through the preservative removing polymer from the Visine®/BAK formulation. The preservative removing polymer was formed as a tapered plug, pre-packed in the outlet tube where approximately 0.1 g of p-HEMA aggregates of an average size of 2 mm was used. The very high BAK removal rates of greater than 99% from the Visine® formulation appears to be enhanced due to the broad dimensions of the plug because of the longer and wider commercial drop outlet tube.

Figure 19:
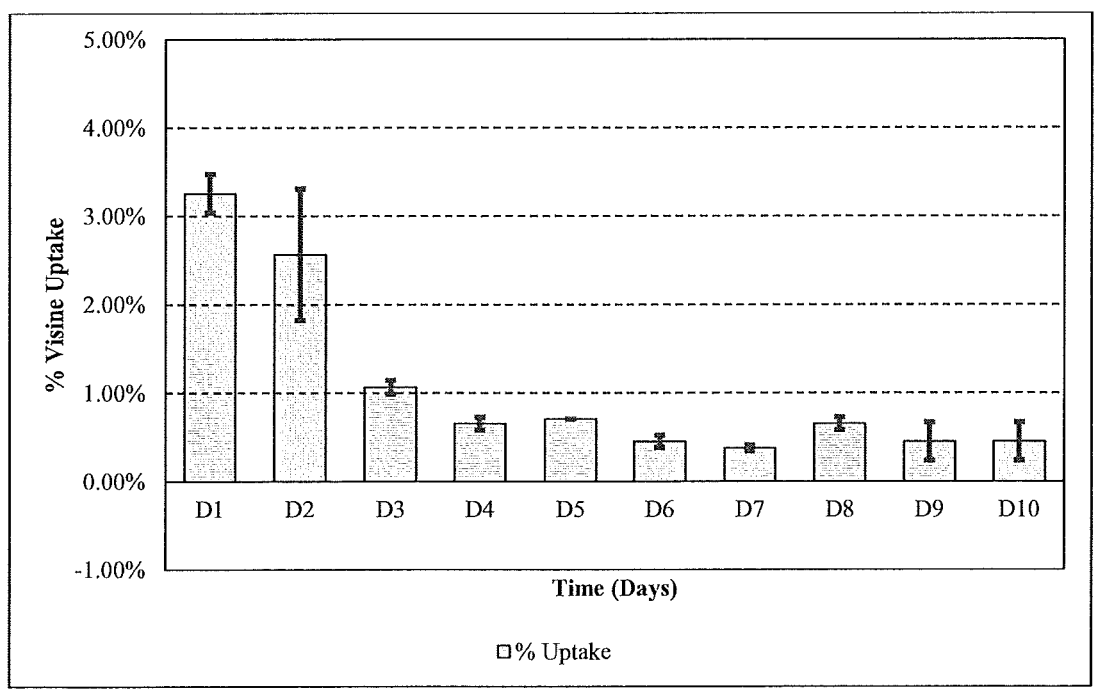
FIG. 19 shows a bar chart for Visine® uptake for aliquots 300 μL aliquots, ~10 drops, of commercial Visine®/(0.01%) BAK solution passed through packed p-HEMA particles synthesized using SR9035 as cross linker over 10 days, where the 300 μL Visine® formulation drops were re-filtered using a secondary filter to obtain a calibration UV-spectra for quantification of drug uptake.

FIG. 18 shows UV spectral data of filtered (primary) and re-filtered (secondary) Visine®/BAK formulation in range of 190-320 nm over a two day period. The Visine® partitioned into the p-HEMA particle matrix was evaluated using the initial 0.3 ml batch of re-filtered Visine® formulation as a calibration spectrum. The concentration of filtered and re-filtered Visine® formulation based on a least square curve fit method between the measured and reference calibration spectra is estimated to be 0.0967 mg/ml and 0.098 mg/ml, thereby indicating negligible drug uptake. A calculated Visine® partition coefficient of 0.04 in these p-HEMA particle systems indicate a drug uptake of 3.4% for the first aliquot tested based on a 1:1 volume ratio of particles to formulation entrained within the plug. FIG. 19 shows the degree of Visine® uptake from approximately 300 μL/day of the filtered Visine® formulation by filters packed with approximately 0.1 g of p-HEMA particles. The degree of Visine® uptake by these preservative removing particles was negligible for 9 successive aliquots of the Visine®, indicating p-HEMA particles as effective for removal of preservatives from commercial Visine® dry relief formulations.

Figure 28:
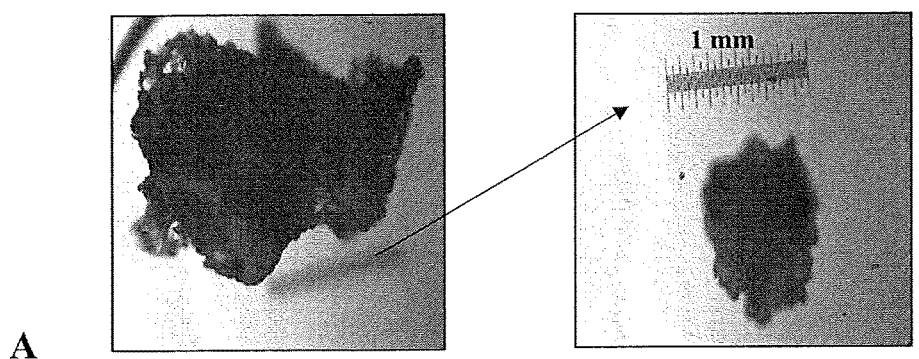
FIG. 28 shows A: p-HEMA aggregates >1 mm B: Fractional BAK removal from Visine/BAK (0.1 wt. %) formulation from p-HEMA filters and the corresponding Visine uptake C.
Figure 28:
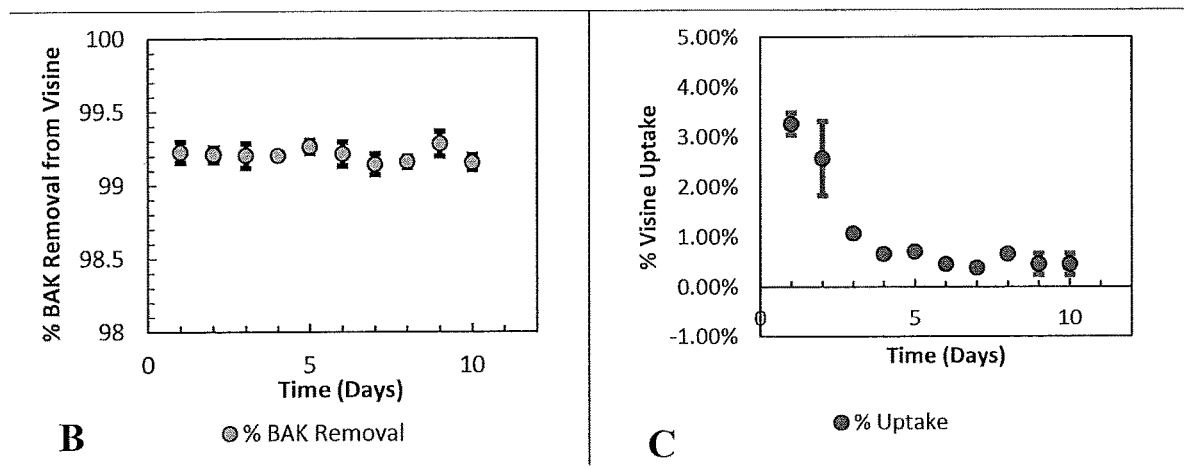
Figure 36A:
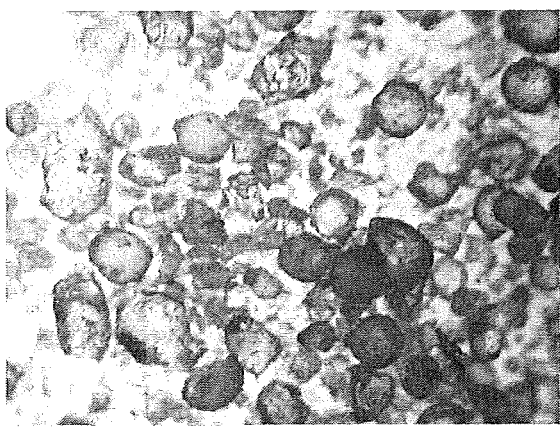
FIG. 36 shows images of 60/40 MAA/DEGDMA particles taken in (A:) high packing and (B:) spread out. Average diameter is 94±15 µm. (C:) 100 µm glass beads.
Figure 36B:
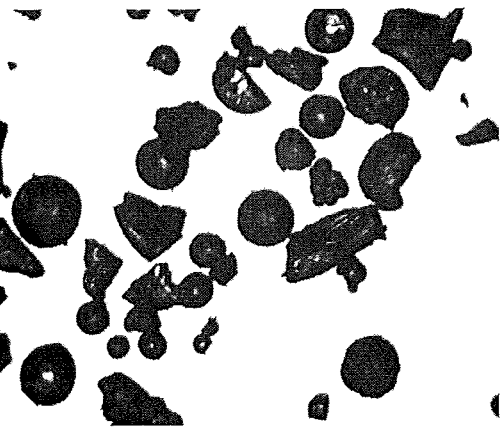
Figure 36C:
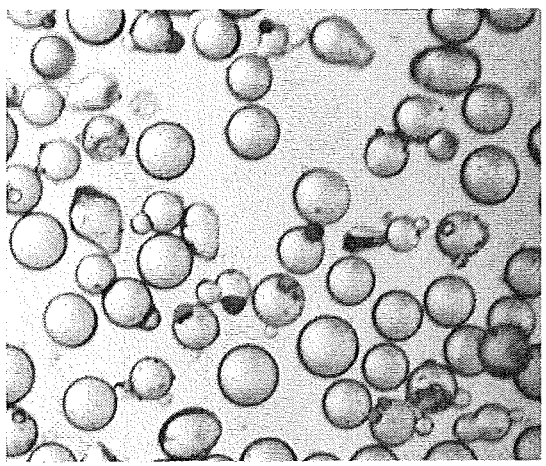

FIG. 28A-C shows optical microscope images of a 1-mm granular aggregate used of studies with commercial Visine formulation. A secondary approach employed to substantiate the claim of high BAK removal efficacy was the addition of cumulative drops of Visine/(0.5 mg/mL BAK) and Visine/(1 mg/mL BAK) formulations to the filtered batch and confirm a decreasing trend in the equilibrium interfacial tension of the filtered formulation. The concentration of BAK in the filtered Visine formulation after addition of concentrated Visine/BAK solution was calculated based on the steady state Langmuir adsorption isotherm. A consistent overlap of dynamic surface tension data as shown in FIG. 28A-C for multiple 0.3 mL batches of filtered Visine/BAK formulation for more than 7 successive measurements validates a high BAK removal rate in p-HEMA filters. Since the estimate of equilibrium surface tension for preservative-free Visine formulation was unavailable due to the absence of a calibration solution, the % BAK removal data were evaluated based on the initial 03 ml batch of filtered Visine formulation as a reference. FIG. 28B represents the fractional removal of BAK from multiple 0.3 mL batches of filtered Visine/BAK formulation. As mentioned earlier, experiments were conducted using a commercial 15 mL Visine Dry eye relief eye drop bottle with a tapered plug, pre-packed with approximately 0.1 g of p-HEMA aggregates of an average size of 2 mm. The % BAK removal data indicate the exceptional capability of p-HEMA particles to selectively remove more than 99% of BAK in the formulation even when the synthesized particle matrix is twice the size of their concomitant 1 mm p-HEMA particles. It is speculated that high BAK removal rates >99% from Visine formulation is attributed to the broad dimensions of the plug (i.e. longer and wider commercial plug). The rate of BAK removal was nearly 99% for all 10 successive batches of filtered Visine solution (10 drops~0.3 mL). These results are also validated by consistent estimates of measured interfacial tension of filtered Visine formulation, showing promise of an efficient design that could be integrated into the commercially available lubricant eye drop filter bottles. The absence of a control calibration solution of preservative-free Visine formulation posed a problem for quantifying the amount of drug partitioned into the p-HEMA particle matrix. A technique adopted to resolve this issue was a secondary filter treatment which enabled the filtered Visine formulation to be re-filtered using a 15-ml commercial Visine bottle replicate pre-packed with ~0.0.1 g of p-HEMA particles. For testing, the eye drop bottle was inverted and then squeezed to deliver an aliquot of 0.3 ml, approximately 10 drops of filtered Visine formulation. A standard quartz cuvette with a chamber volume of 300 μL and a path length of 10 mm was utilized to obtain the filtered Visine's spectra at a range of 190-400 nm. The 300 μL aliquot of filtered Visine solution was transferred to a replicate of 15 mL commercial Visine bottle with a plug pre-packed with a new cluster of ~0.1 g of dry p-HEMA particle matrix and re-filtered to obtain a secondary UV spectra. Prior to employing these particles for drug uptake studies, a batch of 2 g of p-HEMA particles were rinsed in 2 cycles of 1 L de-ionized water batches and dried. This step was employed to ensure that the absorbance of impurities leached out from these particles was <0.1, thereby enabling accurate characterization of Visine using UV spectra. The amount of Visine partitioned into the p-HEMA particle matrix was evaluated based on the initial 0.3 mL batch of re-filtered Visine formulation as a reference calibration spectrum. The concentration of filtered and re-filtered Visine formulation based on a least square curve fit method between the measured and reference calibration spectra is estimated to be 0.0967 mg/mL and 0.098 mg/mL, thereby meeting the criteria for negligible drug uptake. More details of the fit method can also be found in other references. A calculated Visine partition coefficient of 0.04 in these p-HEMA particle systems indicate a drug uptake as low as 3.4% for the first batch tested based on a 1:1 volume ratio of particles to formulation entrained within the plug. FIG. 36 shows the rate of Visine uptake from approximately 300 μL/day of the filtered Visine formulation by filters packed with approximately 0.1 g of p-HEMA particles. The rate of Visine uptake by these particles was as low as 3.4% (FIG. 28C) for the first batch tested and negligible for 9 successive batches of cumulative filtered solution (10 drops—0.3 ml) tested, indicating p-HEMA particles as candidates for selective removal of preservative from commercial Visine dry relief formulations.

Materials

2-Hydroxyethyl methacrylate (HEMA, 97%) monomer and timolol maleate (>98%) were purchased from Sigma-Aldrich Chemicals (St. Louis, Mo., USA). The cross linker ethoxylated (15) trimethylolpropane tri-acrylate (SR9035) are obtained from Sartomer (Warrington, Pa., USA). Photo initiator Darocur® 1173 was provided by Ciba Specialty Chemicals (Tarrytown, N.Y., USA. Dulbecco's phosphate buffered saline (PBS) was purchased from Mediatech, Inc. (Manassas, Va., USA). Ethanol (200 proof) was purchased from Decon Laboratories Inc. (King of Prussia, Pa., USA). All chemicals were used as received without further purification.

3-Methacryloxy-propyl-tris-(Trimethylsiloxy)-Silane or IRIS monomer was obtained from Wheaton Inc. (Millville, N.J., USA). Levofloxacin (≥98%) and brimonidine tartrate (≥97%) were obtained from Alfa Aesar (Haverhill, Mass., USA) and Asta Tech Inc. (Bristol, Pa., USA) respectively.

Preparation of Particles

HEMA monomer (1.4 ml), cross linker (SR9035) (0.1 ml), deionized (DI) water (12 ml), and photo initiator Darocur® 1173 (20 μl) were mixed in a 20-ml vial and magnetically stirred for 20 minutes at 900 rpm at room temperature. The mixture was the purged by bubbling with pure nitrogen for 30 min. After degassing, the mixture was poured into a 55×17 mm (diameter×height) Pyrex® petri dish and irradiated with UV light for 2 hours by a UVB-10 transilluminator (ULTRA-LUM INC. Carson. Calif. USA) with an intensity of 16.50 mW/cm$^2$ sharply peaked at 310 nm. During UV curing, the petri dish was covered to avoid water evaporation and oxygenation, and the mixture were stirred by a 35×6 mm magnetic stir bar at about 90 rpm. After polymerization, the p-HEMA gel particles were separated from the solution by vacuum filtration and washed with a large quantity of DI water. The p-HEMA gel was soaked in 60 mL of pure ethanol for overnight and again separated from the particles by vacuum filtration and washed with a large quantity of DI water. The p-HEMA gel was transferred to 350 ml of DI water and soaked for 24 hours. The DI water was replaced with a fresh batch of DI water every 24 hours for 4 days in succession. Finally, the p-HEMA gel particles were dried in an oven of 80° C. and crushed into finer particles using a mortar and stored for subsequent experimentation.

The same protocol was adopted to synthesize the 25 (v/v %) HEMA/75 (v/v %) tert-butyl methacrylate particle systems with the composition of the added monomers being 0.35 mL of HEMA and 1.05 mL of tert-butyl methacrylate respectively. Different formulations of specific volume fractions of methacrylate based monomers can be synthesized by adjusting the volume ratios in the monomer mixture batch prior to the free-radical polymerization process.

Eye Drop Bottle Prototype

Commercial eye drop dispensing plastic bottles used for preservative removal studies were purchased from Topwel Inc. The standard plug of the eye drop bottle was detached and filled with two layers of 111AM pore size filter paper (9/32-inch diameter punched holes) near the plug's nozzle. The layers of filter paper were placed to ensure that finer particles from the packed filter are not dispensed into the filtered eye-drop formulation. The filter papers can be replaced with suitably designed thin plastic filter to achieve the same objective. This filter can be designed to achieve minimal increase in hydraulic resistance of the entire device. Additionally the material of this filter should not bind any drug.

Approximately, 0.1 g of synthesized p-HEMA or (p-HEMA/TRIS/tert-butyl methacrylate) particles, or 0.07 g of p-HEMA/tert-butyl methacrylate particles was packed in the plug above the layers of filter paper near the nozzle. The base of the plug was covered with two additional layers of 11 µM pore size filter paper (9/32-inch diameter punched holes) before addition of a layer of filter cloth (0.7 cm×0.6 cm) to ensure that the particles stay intact within the plug. The added layer of filter cloth was tapped with a tweezer or a spatula to compress the particle bed and secure its position near the plug's base. The filter/packed plug was mounted onto the eye-drop bottle's neck to complete the proposed design. FIG. 1 shows a photographic representation of the designed eye drop filter bottle.

Figure 20:
FIG. 20 is a photograph of a retention filter prepared by 3D printing for placement in a bottle tip, according to an embodiment of the disclosure.

The filter paper at the top and the filter cloth at the bottom are potentially advantageous to ensuring the retention of the particles in the tip. The design of these filters whose purpose is to ensure retention of the particles is potentially advantageous to ensure that the hydraulic permeability is not reduced significantly and the binding of the drug to these is minimal. An example of a retention filter prepared by 3D printing for placement in a bottle tip is shown in FIG. 20. The retention filters could have circular pores of long slots to achieve high hydraulic permeability while ensuring retention of the particles. A size of 0.1 mm would be preferable to ensure that even the smallest particles do not flow out of the tip or fall down into the formulation. For particles that are larger than 0.1 mm the size of the pores in the retention filters can be increased.

Alternatively the particles could be fully enclosed on all sides and placed inside a holder that is then placed inside the tip. All constraints that are described for the retention filters are relevant to the holder assembly as well. In an alternative design, the particles can be sintered to produce a monolith. Other types of particles could be mixed in with the particles designed for BAK removal to facilitate the sintering. Other approaches such as using a suitable biocompatible glue to could be used to design the monolith. While packing particles along with the suitable retention filters and or holder assembly, it may be useful if the edge of the device is as close as possible and possibly flush with the tip exist where the drop forms. This would be important to ensure that there is no space in between the edge of the device and the exit of the tip where bacteria taken in at the time of the eye drop instillation could attach and grow. The particles in the device can be pre-loaded with BAK or an alternative preservative to minimize the possibility of growth of microorganisms inside the particle bed. If pre-loaded with BAK, the concentration of the BAK in the eluting eye drops may likely be in equilibrium with that of the pre-loaded concentration in the particles. For example if the concentration of the BAK loaded into the particles is 300 ppm and the partition coefficient of the BAK in the particles is 300, the concentration of BAK in the eluting eye drops may be at least 1 ppm.

Figure 23:
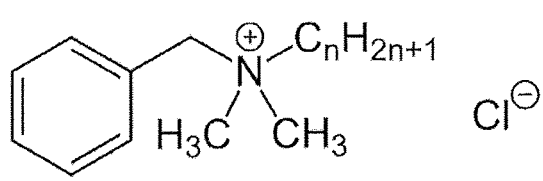
FIG. 23 shows schematic representation of the eye-drop filter bottle with a tapered plug embedded with approximately 0.1 g of p-HEMA or 0.07 g of p-HEMA/Tert-Butyl Methacrylate particle matrix. Different filter plugs and their dimensions used for the experimental study are also illustrated.
Figure 23:
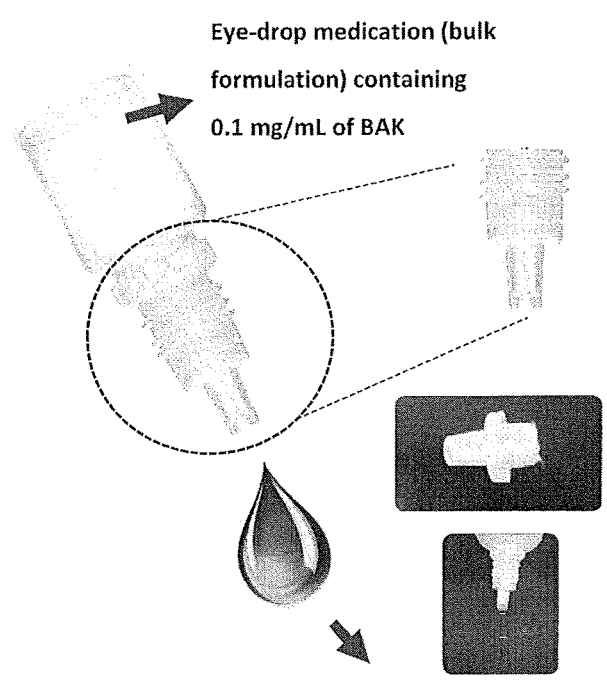
Figure 23:
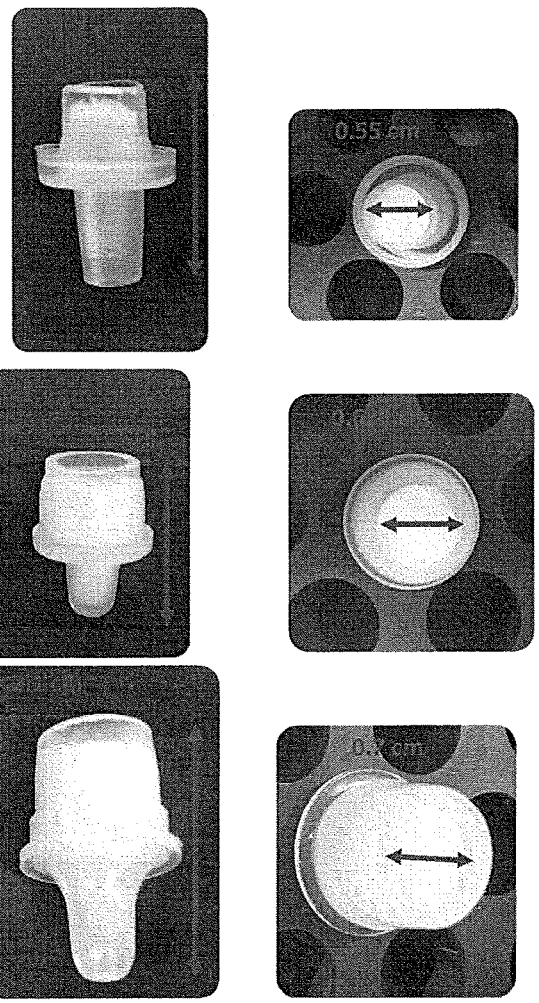

FIG. 23 shows a schematic representation of the designed eye drop filter bottle. The illustration also shows different filter plugs and their dimensions used for the experimental study. The eye drop bottle with a filter plug is designed from a thermoplastic material like polyethylene or polypropylene which exhibits elastic deformation at room temperature upon application of a sufficient load through finger manipulation. The temporary structural change of the bottle by application of a finger force compresses the air present in the eye drop bottle thus, inflicting an enhanced pressure on the active pharmaceutical formulation in the bottle. This allows one to dispense drops of pharmaceutical medication through the packed bed of particles present in the filter plug enabling selective adsorption of Benzalkonium chloride by the microparticles.

Morphology of Synthesized Particles

Figure 2A:
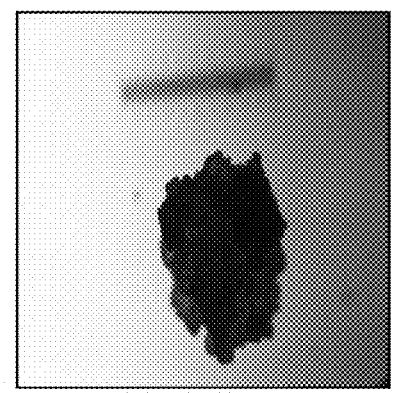
FIG. 2A shows Optical Microscope Images of irregular shaped 1-mm p-HEMA aggregate and FIG. 2B shows the p-HEMA matrix at 10× magnification formed using Tri-acrylate (SR9305) cross linker.
Figure 2B:
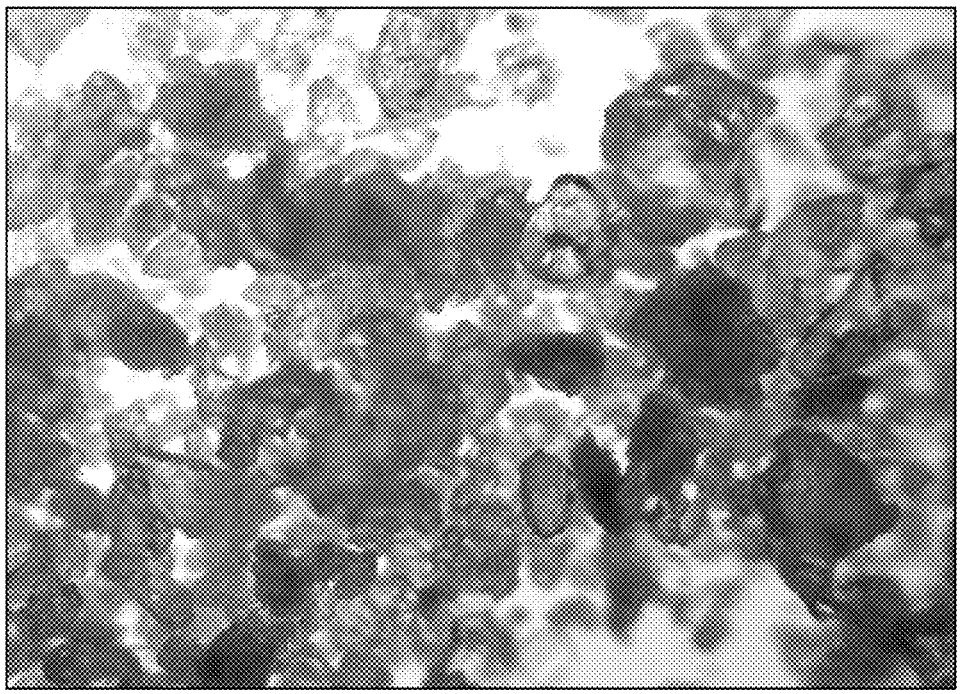
Figure 3:
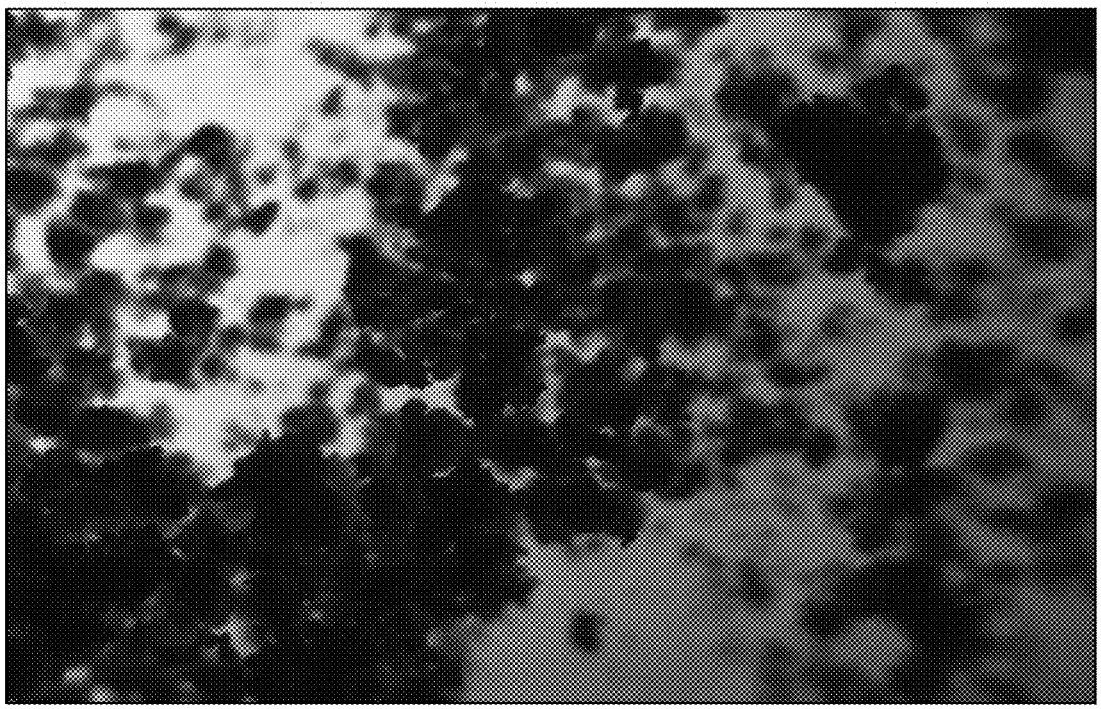
FIG. 3 shows an Optical Microscope Images of finer p-HEMA (25 v/v %)/Tert-butyl Methacrylate (75 v/v %) particle of average particle size <1 mm at 10× magnification synthesized using 2-Hydroxyethyl Methacrylate and Tert-butyl Methacrylate with Ethoxylated Trimethylolpropane Tri-acrylate (SR9305) cross linker, according to an embodiment of the disclosure.
Figure 4:
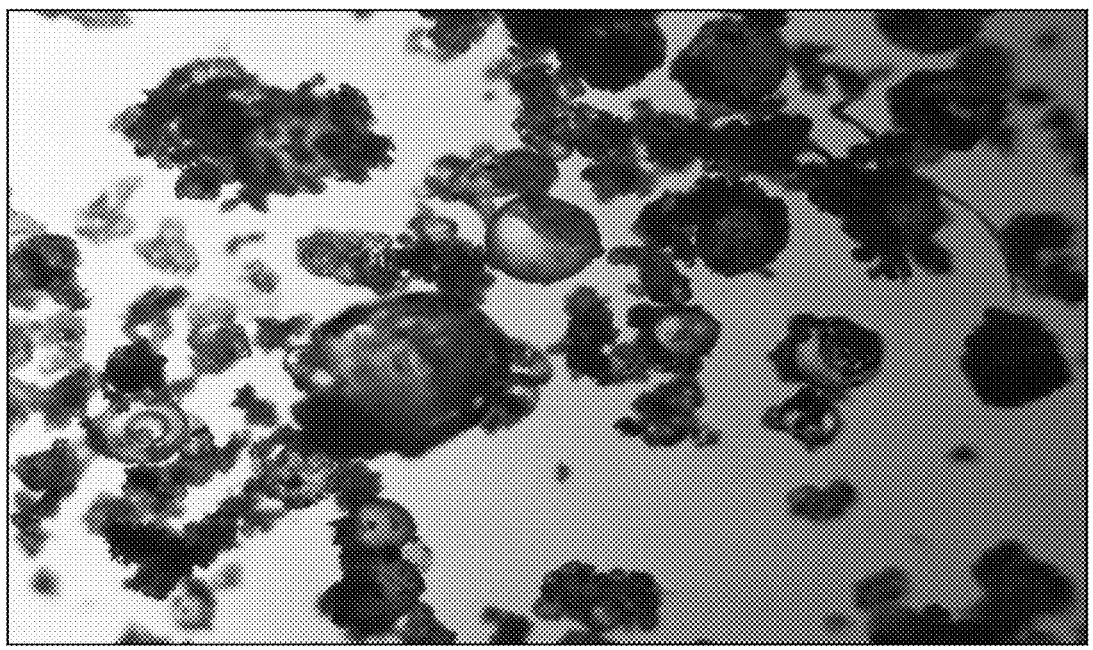
FIG. 4 shows an Optical Microscope Image of fine p-HEMA (25 v/v %)/TRIS (37.5 v/v %)/Tert-butyl Methacrylate (37.5 v/v %) particle of average particle size <1 mm at 10× magnification from 2-Hydroxyethyl Methacrylate, TRIS. Tert-butyl Methacrylate, and Ethoxylated Trimethylolpropane Tri-acrylate (SR9305) cross linker, according to an embodiment of the disclosure.

Optical Microscope images were obtained on a 10×-100× digital monocular compound microscope (Amscope) in the Chemical Engineering Department at the University of Florida, Gainesville. The synthesized particles imaged include p-HEMA, p-HEMA (25 v/v %)/Tert-butyl Methacrylate (75 v/v %), and p-HEMA (25 v/v %)/TRIS (37.5 v/v %)/Tert-butyl methacrylate particles. A batch of approximately 0.01 g of particles of different composition were placed on a pre-cleaned glass slide and imaged at a magnification range of 10×. FIG. 2A shows the Optical Microscope Images of a 1-mm p-HEMA aggregate and FIG. 2B shows an image of p-HEMA matrix at a 10× magnification. These particles are irregular-shaped rigid aggregates synthesized using 2-Hydroxyethyl methacrylate as the primary monomer and ethoxylated trimethylolpropane tri-acrylate (SR9305) cross-linker. Though the particle size distribution of the p-HEMA matrix was broad, a randomized selection of particle aggregates from the batch analyzed using ImageJ software estimated the average particle size to be 0.79-0.961 mm. FIG. 3 and FIG. 4 show images of fine p-HEMA (25 v/v %)/tert-butyl methacrylate (75 v/v %) and p-HEMA (25 v/v %)/TRIS (37.5 v/v %)/tert-butyl methacrylate particles at 10× magnification factor. Though these particles are irregular in shape, a characteristic feature of these particles is their smaller size (<1 mm and >0.5 mm) in comparison to the p-HEMA particles. This feature is beneficial for obtaining higher BAK removal rates from the drug/BAK formulations due to an increase in the contact time of aqueous solution with the filter bed.

Figure 21:
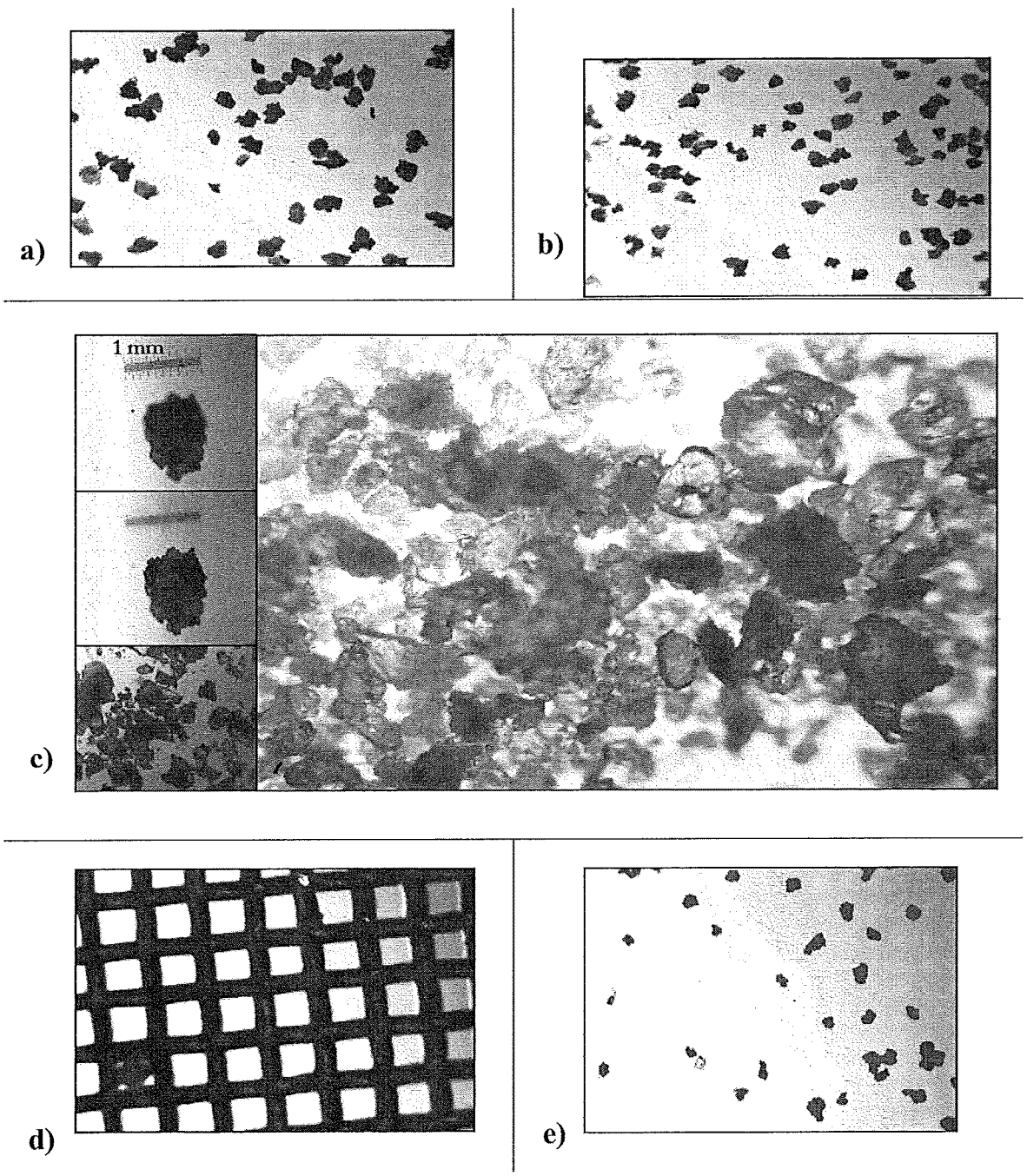
FIG. 21 shows optical microscope images of A, B: p-HEMA (25 v/v %)/Tert-butyl Methacrylate (75 v/v %) and p-HEMA (15 v/v %)/Tert-butyl Methacrylate (85 v/v %) particles of 63-125 µm size fraction at 4× magnification. C: Images of 1 mm p-HEMA aggregates and the matrix. D: Representative image of a 125 µm standard sieve used for image calibration. E: A processed threshold image of p-HEMA (25 v/v %)/Tert-butyl Methacrylate (75 v/v %) particle batch used for size characterization.
Figure 22:
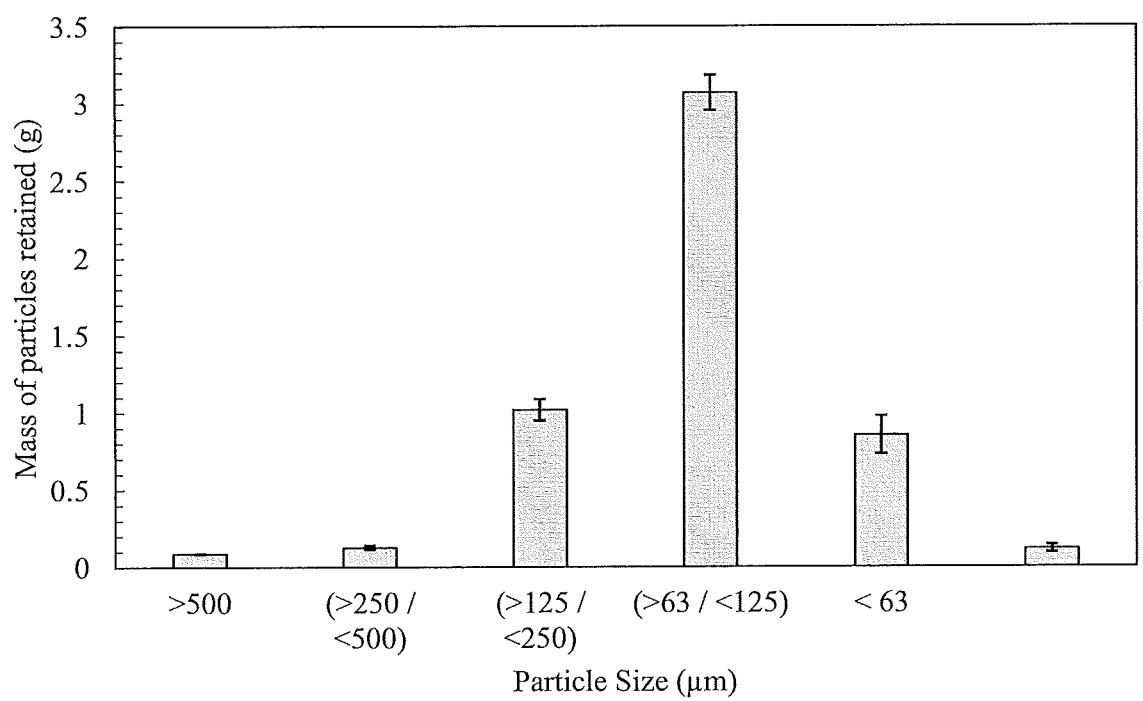
FIG. 22 shows a bar chart of effective mass of p-HEMA (15 v/v %)/TBM (85 v/v %) particles retained on standard screens or sieves with Tyler mesh size ranging from 35-230 with equivalent mesh opening ranging from 63-500 µm.

FIG. 21A-E shows the optical microscope images of a 1-mm p-HEMA aggregate (FIG. 21C) and p-HEMA matrix (FIG. 21C) at a 10× magnification. These particles are irregular-shaped rigid aggregates synthesized using 2-hydroxyethyl methacrylate as the primary monomer and ethoxylated trimethylolpropane tri-acrylate (SR9305) cross linker. FIG. 21A and FIG. 21B show the image of the finer p-HEMA (25 v/v %)/tert-butyl methacrylate (75 v/v %) and p-HEMA (15 v/v %)/tert-butyl methacrylate (85 v/v %) at a 10× magnification factor. These irregular solid particles were pulverized through compression and sifted using standard screens to yield 63-250 μm sized particles. Compression and screen analysis were explored to get a uniform particle size distribution and avoid the possibility of channeling in the packed filter bed. Images of the particle matrices analyzed using ImageJ software yielded an average Feret diameter of 60-110 μm, which agrees with the mesh diameter of the standard sieves. Results of screen analysis are presented in Table 5 and FIG. 22.

TABLE 5

Screen analysis performed for 2 different 5 g batches of p-HEMA (15 v/v %)/TBM (85 v/v %)

| Designated Mesh | Screen Opening (μm) | Particles mass retained (g) | Mass fraction, $x_i$ | Average particle diameter in increment, $\overline{D}_p$ (μm) | Cumulative fraction smaller than $\overline{D}_p$ (μm) |
|---|---|---|---|---|---|
| Batch Number: # 1 | | | | | |
| 35 | 500 | 0.0898 | 0.0167 | — | 0.9833 |
| 60 | 250 | 0.1382 | 0.0257 | 375 | 0.9743 |
| 120 | 125 | 0.9694 | 0.1799 | 187.5 | 0.8201 |
| 230 | 63 | 3.1487 | 0.5845 | 94 | 0.4155 |
| Pan | — | 0.9413 | 0.1747 | 31.5 | 0.8253 |
| Particle dust (<63 μm) lost upon sieving | | 0.1 | 0.0186 | — | 0.9814 |
| Total mass of synthesized particles (g) | | | 5.3874 | | |
| Batch Number: # 2 | | | | | |
| 35 | 500 | 0.0865 | 0.01675 | — | 0.98325 |
| 60 | 250 | 0.1182 | 0.02789 | 375 | 0.97711 |
| 120 | 125 | 1.0675 | 0.20676 | 187.5 | 0.79324 |
| 230 | 63 | 2.9878 | 0.57869 | 94 | 0.42131 |
| Pan | — | 0.7685 | 0.14885 | 31.5 | 0.85115 |
| Particle dust (<63 μm) lost upon sieving | | 0.1345 | 0.02605 | — | 0.97395 |
| Total mass of synthesized particles (g) | | | 5.163 | | |

Hydraulic Permeability of p-HEMA Particle Matrix

The hydraulic permeability of the p-HEMA particles packed in a standard 3 mL Luer lock syringe was measured by applying a weight of 0.4535 kg (1 lb.) on the syringe filled with 1.5 ml of DI water. The flow rate (Q) of water was calculated by measuring the time needed to elute the pre-filled water through the bed of p-HEMA particles. The hydraulic permeability of a 2-cm packed bed of polyhydroxyethyl methacrylate (p-HEMA) particles is calculated using Darcy's law as given by $$Q = \frac{Ak\Delta P}{\mu L}$$ (Equation 11)

$$K = \frac{V \mu L}{t(mg)},$$

where k is the Hydraulic permeability of p-HEMA particle bed, A is the cross-sectional area of the bed (m²) V is the volume of DI water eluted after applying a 1 lb. weight on the particle bed, ΔP is the pressure drop across the filter bed, L is the length of particle bed (2 cm), m is the mass of the constant load applied near the plunger's tip (1 lb. or 0.4536 kg), p is the viscosity of DI water (1 cP), and g is the acceleration due to gravity (9.81 m/s²). The hydraulic permeability of the p-HEMA particles synthesized by using SR9035 cross linker was determined to be 2.513±0.599 Darcy (mean±SD). A high hydraulic permeability estimates >1 Da of these particles satisfy the design target of a functional filter providing a low resistance to formulation flow through the packed bed.

A second method to estimate the hydraulic permeability of the filter material was devised. The eye drop bottle with a filter plug is designed from a thermoplastic material like polyethylene or polypropylene which exhibits elastic deformation at room temperature upon application of a sufficient load through finger manipulation. The temporary structural change of the bottle by application of a finger force compresses the air present in the eye drop bottle thus, inflicting an enhanced pressure on the active pharmaceutical formulation in the bottle. A pipette tip on mounted on top of the filter plug packed with 25% p-HEMA/75% TBM particles present in the eye-drop bottle and affixed using a scotch tape. The filter bottle was inverted and squeezed using a fingertip force to push 5 ml DI water in the bottle through the packed bed filter. When the applied squeezing pressure is removed, the pressure inside the bottle becomes smaller than atmospheric pressure, which causes the solution in the tip to flow back into the bottle. Since the filter tip is mounted with a transparent pipette tip, the DI water draining through this window can be visualized and recorded for analyzing flow rate of the liquid. With the filter packed with particles, the draining DI water is offered some resistance to flow by the packed bed particles and continues to drain till the air pressure inside the bottle is restored back to the atmospheric pressure. By measuring the flow rate of the solution returning to the bottle, we can calculate the hydraulic permeability of the packed particles by utilizing Darcy's law. Since the temperature change is negligible and the mass of the gas in the eye drop bottle remains constant before and after the squeeze, we know from the ideal gas law that $$P_0 V_0 = P_f(V_0 + \Delta V)$$ (Equation 12)

where $P_0$ is the pressure in the eye drop bottle before the bottle is squeezed which also equals to atmospheric pressure. $P_f$ is the pressure in the bottle after the bottle is squeezed, $V_0$ is the volume of the air before the dropper bottle with applicator is squeezed and ΔV corresponds to the volume of DI water being pushed out of the bottle. Table 2 presents the hydraulic permeability values of p-HEMA particles and different size fractions of 25%/75% p-HEMA/TBM particles. It was noticed that addition of a filter cloth used to compress and pack the particles in the plug induced additional resistance to formulation flow. This is observed for all size fractions and results in reduction of hydraulic permeability. A layer of filter cloth was replaced by a permeable filter paper to resolve the issue. A high hydraulic permeability of >1 Da for all size fractions satisfies one of the primary design constraints of a filter material.

TABLE 6

Summary of Hydraulic Permeability of p-HEMA particles and different size fractions of 25%/75% p-HEMA/TBM particles.

| Volume of liquid collected (V) - [mL] | Time (t)-[s] | Hydraulic Permeability (m²) | Hydraulic Permeability (Darcy) |
|---|---|---|---|
| 1 | 2.5 | 1.79783E−12 | 1.822 |
| 1.5 | 2.4 | 2.8091E−12 | 2.846 |
| 1.5 | 2.38 | 2.83271E−12 | 2.870 |
| Mean Hydraulic permeability (Darcy) | | | 2.513 |
| Standard Deviation | | | 0.599 |

TABLE 6-continued

Summary of Hydraulic Permeability of p-HEMA particles and different size fractions of 25%/75% p-HEMA/TBM particles.

| 25% HEMA/75% TBM particle size (μm) | Average with filter cloth (Darcy) | Calculated from Ergun Equation | Without filter cloth (Darcy) |
|---|---|---|---|
| 63-125 | 0.99 | 1.18 | 1.87 |
| 125-250 | 1.57 | 4.67 | 2.70 |
| 250-500 | 1.94 | 18.72 | 3.86 |
| >500 | 3.99 | 74.82 | 5.41 |

Interfacial Tension

The dynamic interfacial tension of filtered ophthalmic formulations was measured via pendant drop tensiometry using the commercially automated instrument named Kruss DSA 100 (Drop Shape Analyzer). A pendant drop is a drop of the filtered formulation was suspended at the tip of a 14-gauge needle with air as the surrounding phase. The silhouette of the axisymmetric formulation drop is imaged at regular time intervals and iteratively fit to Young-Laplace equation to measure its dynamic surface tension as a function of time. This robust method is commonly employed due to a high-speed and precise estimation of interfacial tension based on drop curvature and concentration of the formulation.

Figure 5:
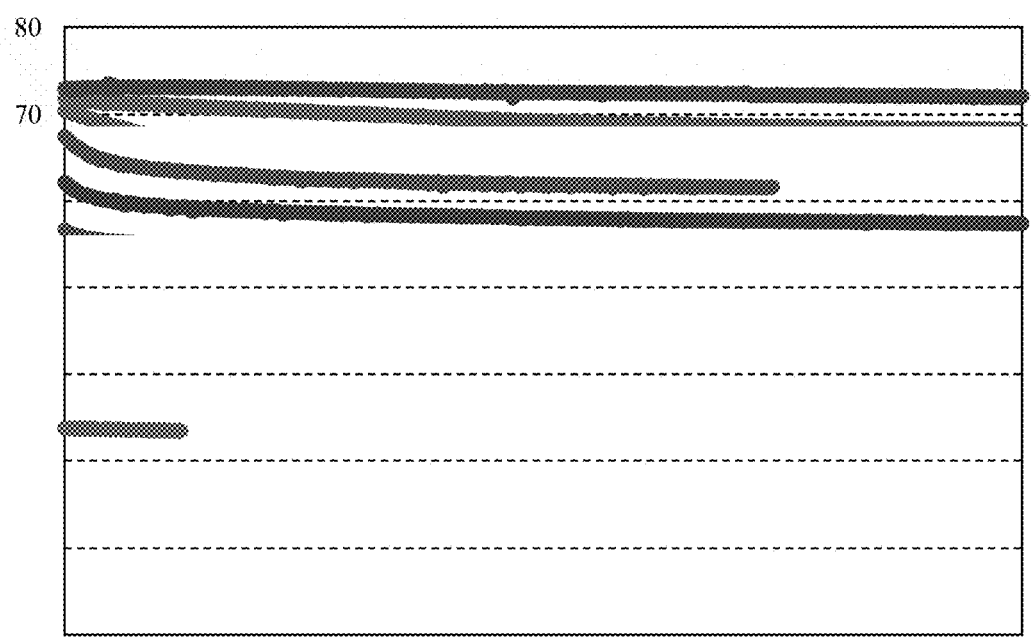
FIG. 5 shows plots of the dynamic interfacial tension of 0.5 mL BAK-air interfaces as a function of BAK concentration in PBS as an aqueous phase for BAK/PBS formulations with 0.002 mg/ml to 2 mg/ml BAK with interfacial tension data presented as 'mean±σ' with n=1 per calibration solution.
Figure 6:
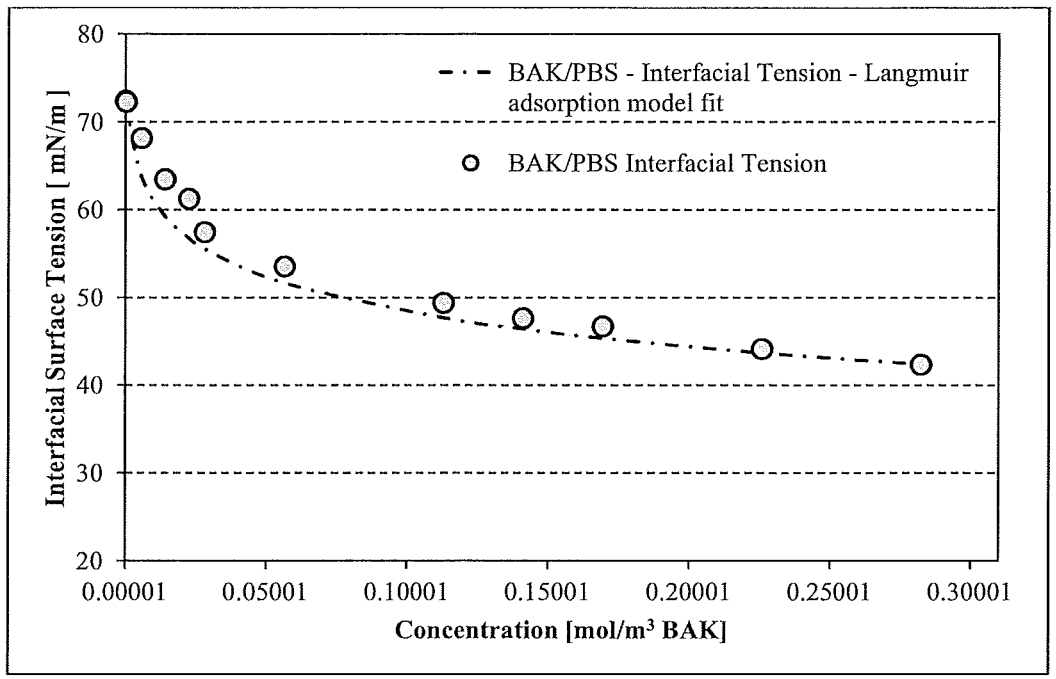
FIG. 6 is a plot of the equilibrium interfacial surface tension of BAK-air interface as a function of BAK concentration in the aqueous phase (1×-PBS) where solid black lines represents a steady state Langmuir surfactant adsorption isotherm model fit to experimental interfacial tension data of aqueous BAK formulation.
Figure 25:
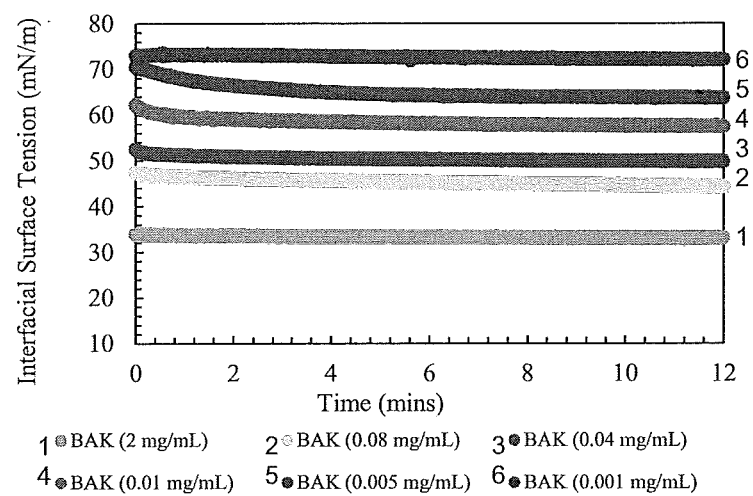
FIG. 25 shows Dynamic interfacial tension of 0.5 mL BAK-air interface as a function of BAK concentration in PBS as an aqueous phase. The concentration of BAK/PBS formulations explored for interfacial tension measurements range from 0.002 mg/mL to 2 mg/mL.

BAK is a cationic surfactant, so the surface tension of a solution containing BAK is lower than that of water, which can be used to determine the concentration of BAK in a solution. Calibration curves relating solution surface tension to the BAK concentration, were constructed by measuring the dynamic surface tension of BAK solutions for concentrations ranging from 0.002 to 2 mg/mL as shown in FIG. 5 and FIG. 25. For aqueous systems containing BAK, a cationic surfactant, the dynamic interfacial tension decreases rapidly until an equilibrium surface tension is obtained. The time scale which may be required for the formulation's dynamic surface tension to attain a state of equilibrium is approximately 12 minutes. No significant changes were observed at time intervals longer than 12 minutes. The equilibrium interfacial tension, i.e. dynamic interfacial tension of the suspended formulation after 12 minutes of interfacial surface generation was used to construct a calibration curve of equilibrium interfacial tension, as shown in FIG. 6 as a function of BAK concentration in the calibration solution. Since the dynamics of interfacial tension is rate limited by kinetics of adsorption and desorption of the free surfactant units on the interfacial surface, the steady state Langmuir adsorption isotherm model along with $$\Gamma_{eq} = \frac{\left|\left(\frac{\beta}{\alpha}\right)\Gamma\infty c\right|}{\left|\left(\frac{\beta}{\alpha}\right)c+1\right|} \quad \text{(Equation 13)}$$

the Langmuir surface equation of state is used to relate equilibrium interfacial tension and concentration of the filtered formulation. The steady state Langmuir adsorption isotherm and the equation of state is given by $$\Upsilon_0 - \gamma = -RT\Gamma\infty\ln\left(1 - \frac{\Gamma_{eq}}{\Gamma_\infty}\right) \quad \text{(Equation 14)}$$

$$\Upsilon_0 - \gamma = RT\Gamma\infty\ln\left(1 + \left(\frac{\beta}{\alpha}\right)c\right),$$

where $r_{eq}$ is the equilibrium molar surface concentration, $r_\infty$ is the maximum molar surface concentration, C is the bulk concentration of the aqueous formulation, $\alpha$ and $\beta$ are adsorption and desorption constants, R is the ideal gas constant, $\gamma_o$ is the interfacial tension of the pure solvent (PBS). $\gamma$ is the equilibrium interfacial tension recorded after 12 minutes of interfacial surface generation, and T is the operating temperature for acquisition of interfacial tension of drug/BAK formulation (recorded at room temperature, 298 K). A least square minimization protocol was used to fit the experimental equilibrium surface tension values and calculate the fit parameters in the Langmuir adsorption isotherm model. The fit parameters $r_\infty$, maximum surface coverage and $(\beta/\alpha)$, the ratio of adsorption and desorption rate constants were estimated to be 611.606 m$^3$/mol and 2.352×10 mol/m$^2$ respectively. With the potentially advantageous fit parameters including $r_\infty$, maximum surface coverage and (D/a), the ratio of rate constants evaluated, concentration of the BAK in the filtered formulation was calculated based on the steady state Langmuir adsorption isotherm.

Selective Removal of BAK

The efficacy of selective removal of BAK was evaluated by a modified 30 mL eye drop bottle with a tapered plug, pre-packed with approximately 0.1 g of p-HEMA or (p-HEMA/TRIS/tert-Butyl methacrylate) particles, or 0.07 g of p-HEMA/tert-butyl methacrylate particles. The designed eye drop bottle was filled with 10 mL of drug/PBS solution prior mounting the plug. For testing, the eye drop bottle was inverted and then squeezed to deliver an aliquot of 0.5 mL, approximately 15 drops of filtered drug formulation. A standard 5 mL vial or a microplate was used for collecting the filtered formulation for surface tension measurements. The dosed formulation was withdrawn from the vial or microplate using a graduated 3 mL Luer-lock syringe and a needle. A 30 μL pendant drop of filtered formulation suspended from a 14-gauge needle was created by maintaining the flow rate of the dosed solution at 100 μl/min. Interfacial tension measurements of the filtered drug formulation were done on the DSA Kruss Pendant drop tensiometer. A dose regimen of 24 hours was assigned between successive batches of the filtered formulation (0.5 mL) withdrawn, and their surface tension monitored. All the interfacial tension measurements were conducted at a room temperature of approximately 25° C.

UV Absorbance

The lab-made hydrophilic drug formulations used for this study include timolol maleate (0.5%), levofloxacin (0.5%), dorzolamide (2%), brimonidine tartrate (0.2%), pilocarpine (0.1 wt. %) and Combigan, a combinational therapeutic formulation of brimonidine tartrate (0.2 wt. %) and timolol maleate. Commercial formulations including Visine® Dry eye relief lubricant eye drops and timolol Maleate ophthalmic solution were used as supplied with no further processing. Aqueous solutions of the drug in PBS were prepared by subjecting them to vortex mixing for a minute to ensure complete mixing prior UV-Vis spectral measurements. An aqueous solution of dorzolamide (2%) in PBS was additionally kept for magnetic stirring overnight to ensure complete dissolution of the drug. The uptake of all the hydrophilic drugs by p-HEMA and p-HEMA (25 v/v %)/tert-butyl methacrylate (75 v/v %) particle systems during drop dosage was quantified by UV-Vis spectral analysis (GENESYS™ 10 UV, Thermo Spectronic, Rochester, N.Y., USA). The UV spectra of filtered drug/PBS formulation were obtained in the spectral range of 280-310 nm for timolol, 265-310 nm for Levofloxacin, 210-300 nm for brimonidine, 210-250 nm for pilocarpine, 210-310 for Combigan, 190-240 nm for Visine® commercial formulation, and 220-290 nm for dorzolamide respectively. The concentration of drug in the filtered formulation was determined through a least square curve fit method between the measured and reference calibration spectra. MATLAB's fminsearch module was used to deduce optimal values of drug concentration in the filtered solution.

Drug Uptake by the Particle Matrix

The uptake of hydrophilic drugs by p-HEMA. p-HEMA/tert-butyl methacrylate, and p-HEMA/tert-butyl methacrylate/TRIS particle systems was evaluated by a modified 5 mL eye drop bottle with a tapered plug, pre-packed with approximately 0.1 g of p-HEMA or (p-HEMA/tert-butyl methacrylate/TRIS) particles, or 0.07 g of p-HEMA/tert-butyl methacrylate particles. The designed eye drop bottle was filled with 5 mL of drug/PBS solution prior mounting the plug. For testing, the eye drop bottle was inverted and then squeezed with an optimal force to deliver a single drop of filtered formulation.

The UV spectral measurements of filtered formulation were obtained for each filtered drop with a time interval of a day to monitor the drug absorption by p-HEMA and p-HEMA/tert-butyl methacrylate particles. Since the UV-Vis measurements were limited by high drug concentration in the aqueous PBS solution (0.5%), the filtered drop of timolol (0.5%) and levofloxacin (0.5%) was diluted 100-fold to obtain quantitative measurements. Similarly, a 300-fold dilution was used to obtain the UV-spectra of dorzolamide/PBS solution.

Hydrophobic Drugs

Material Selection

Plugs made of pHEMA particles effectively remove BAK but the concentration of dexamethasone, a hydrophobic drug, drops substantially in the first few drops. A hydrophobic drug may not bind to a matrix that is more hydrophilic than pHEMA. One possible improvement was to testing binding of BAK and drug to methacrylic acid.

Materials:

Methacrylic acid, 2-hydroxyethyl methacrylate, and potassium persulfate were purchased from Sigma-Aldrich. Bimatoprost and latanoprost were purchased from Carbosynth. Benzalkonium chloride was purchased from MP Biomedicals. Diethylene glycol dimethacrylate (DEGDMA) was purchased from PolySciences, Inc. SR-9035 was provided by Sartomer. Damcur TPO and Damcur 1173 were provided from Ciba Specialty Chemicals. Phosphate buffered saline, 1× (PBS) was purchased from Mediatech, Inc. Glass beads (0.1 mm diameter, CAT no. 11079101) were purchased from BioSpcc.

Partition Coefficient:

Preparing flat sheets by polymerizing a monomer mixture with water is easier than making particles. Thus, prior to manufacturing particles of methacrylic acid (MAA), partition coefficient was measured by preparing 100 micron thick hydrogel sheets by photo-polymerization of a mixture of 2.7 mL monomer to 2 mL de-ionized water. 8 mg Darocur TPO was added. The gels were then cut into 1 cm×1 cm squares. After cleaning with a 24 hour soak in de-ionized water, the gels were measured to determine their wet weight. The gels were dried and weighed to determine their dry weight. After this, the gels were rehydrated with PBS, and then placed into either 100 μg mL-1 BAK/PBS solution or 250 μg mL-1 bimatoprost/PBS solution. The solution was measured every 24 hours to determine uptake. After equilibrium was reached, the gels were then placed into blank PBS to measure the release. The results could then be used to calculate partition coefficient (K). The water fraction was subtracted from the partition coefficient to give K-f.

Figure 29:
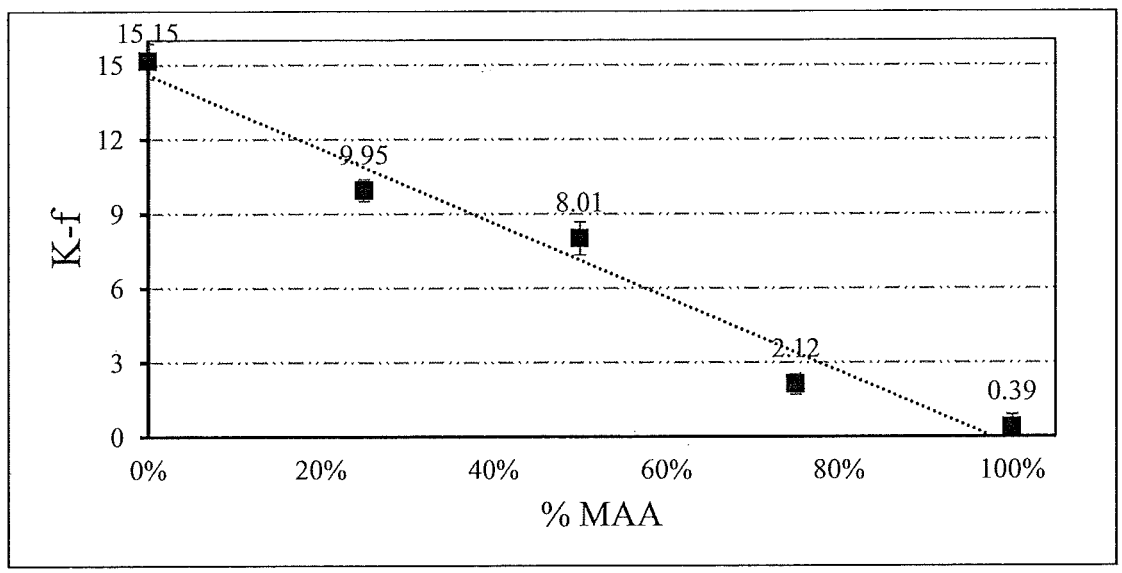
FIG. 29 shows bimatoprost partition coefficient (K-f) in HEMA/MAA hydrogels with SR-9035 cross-linker.

FIG. 29 shows the partition coefficient data of HEMA/MAA gels. Increasing MAA led to a linear decrease of drug partition coefficient. A 100% methacrylic gel (with 1% cross-linker), saw a partition coefficient of 0.39±0.15. Not shown is the partition coefficients for BAK. Pure HEMA showed a partition coefficient of roughly 400, and MAA showed a partition coefficient of roughly 800, suggesting that Methacrylic acid is superior to HEMA for removing BAK from solution.

Particle & TIP Preparation

Hydrogel particles were synthesized by mixing together 1.5 mL of monomer/cross-linker with 12 mL of de-ionized water. A high concentration of crosslinker was used because methacrylic acid (MAA) particles swell significantly which is undesirable in the TIP. Also a hydrophilic crosslinker was used because drug could potentially bind at high concentrations to the hydrophobic crosslinkers. The solution was purged with nitrogen for 30 minutes. For photo-initiation, 20 μL of Darocur 1173 was added. The solution was then irradiated with UV light for 6 hours by a UVB-10 transilluminator (ULTRA•LUM INC, Carson, Calif., USA) with an intensity of 16.50 mW/cm2 sharply peaked at 310 nm. The solution was mixed with a stir bar at 300 rpm. For thermal-initiation, 8 mg of potassium persulfate were added. The solution was then placed in a hot water bath at 60° C. and was mixed with a stir bar at 300 rpm.

After polymerization, the solution was cleaned with multiple de-ionized water soaks. After each soak, the particles were vacuum pumped and dried. The fine grain sire of the thermo-initiated particles used required a larger mesh size to be used to prevent clogging of the filter. After 5 washes, 0.1 g of particles were removed and placed in 3 mL of PBS and left for 24 hours. The solution was then analyzed to determine the level of hydrogel material leeching into solution. If the absorbance peak was above 0.1, then the particles were returned to undergo 5 additional washes.

After the particles were cleaned and dried for the final time, a filter tip was manufactured by first placing two layers of filter paper into the tip, filling it with 0.1-0.15 g of material, and then placing two more layers of filter paper into the tip.

BAK Uptake by Particles Packed in TIP

The uptake of benzalkonium chloride through a filter was measured using 0.1 mg mL-1 BAK/PBS solution. An eye drop bottle was filled with 5 mL of BAK solution and then capped with the tip and filter. Five drops were then eluted into a 200 μL cuvette, and then the eluted volume was measured using UV-vis spectrophotometry. The process was repeated 24 hours later. This gave the rate of 5 drops eluted in quick succession per day.

The measured results could then be analyzed using a two-fit parameter of benzalkonium chloride and another of the hydrogel material. The hydrogel material UV-vis spectra were collected by flowing PBS through a filter.

Drug Uptake by Particles Packed in TIP

The uptake of drug used 250 μg mL-1 bimatoprost/PBS solution and 50 μg mL-1 latanoprost/PBS solution. The uptake was analyzed on a single drop basis. A single drop was eluted into a 200 μL cuvette while the cuvette was placed on a scale. This allowed for the measuring of the eluted mass. The drop was diluted with PBS to attain the volume for measurement. For bimatoprost, a single eluted drop was diluted 10-fold. For latanoprost, a single eluted drop was diluted 4-fold, requiring a stand to elevate the platform of the cuvette.

After dilution, the samples were measured with UV-vis spectrophotometry. The measured results could then be fitted with a two parameter fit, similar to how BAK was analyzed.

Figure 30:
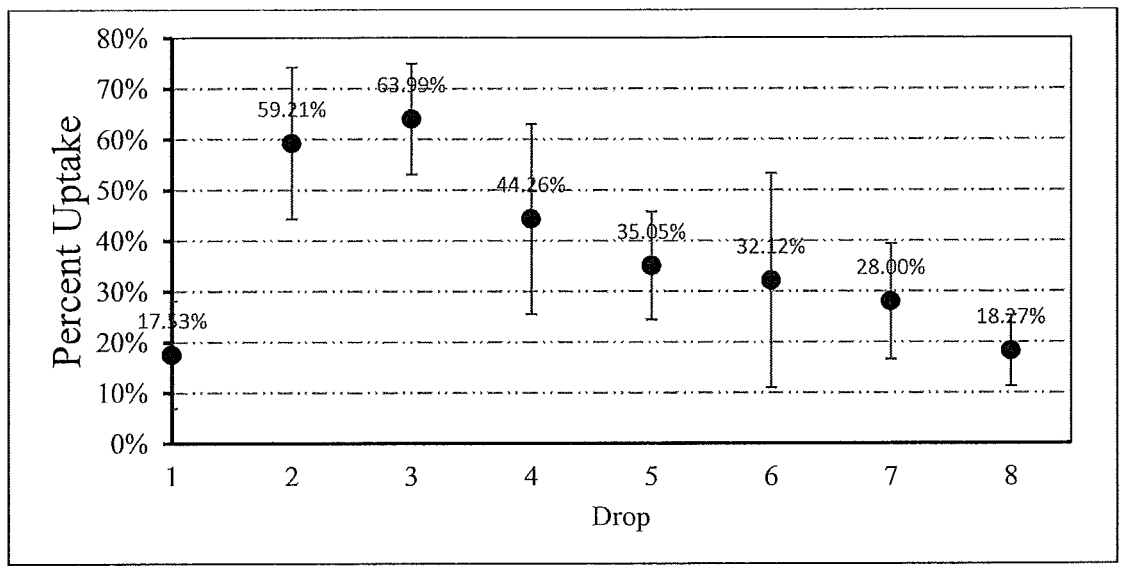
FIG. 30 shows uptake of bimatoprost from 0.1 g 75/25 methacrylic acid/HEMA with SR9035 cross-linker filter. Particles were photo-initiated.

FIG. 30 examines the uptake of bimatoprost of a 75/25 MAA/HEMA filter. The maximum uptake was measured to be approximately 64.0%, which is in agreement with the measured partition coefficient of a 75/25 fraction, which would predict a 67.9% uptake on the second drop. However, such an uptake is too high above the acceptable goal of <5%.

Figure 31:
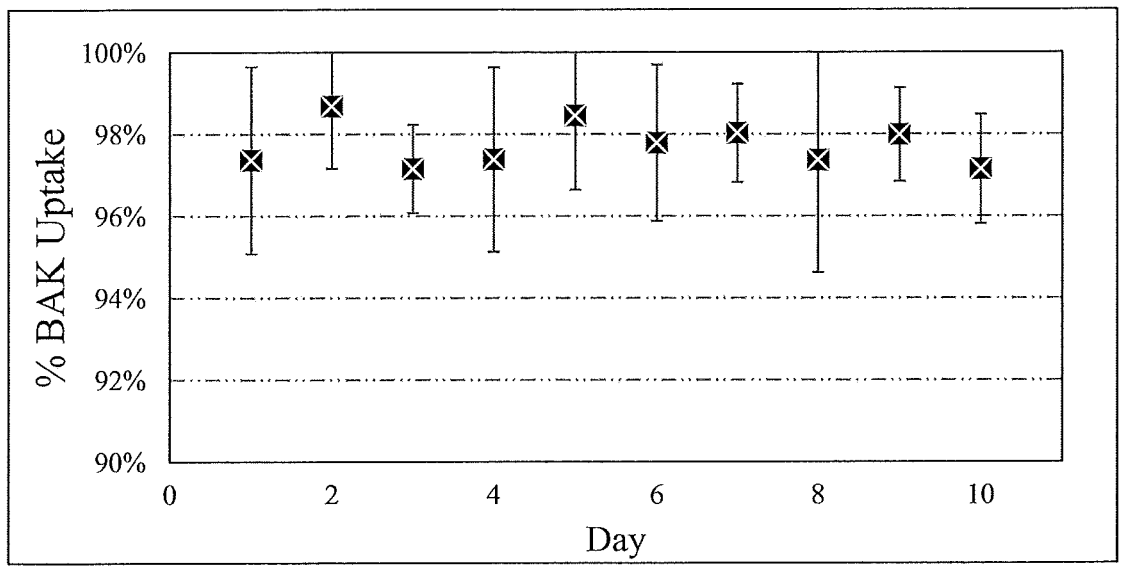
FIG. 31 shows uptake of benzalkonium chloride from 0.1 g 60/40 methacrylic acid/DEGDMA filter. Particles were thermal-initiated
Figure 32A:
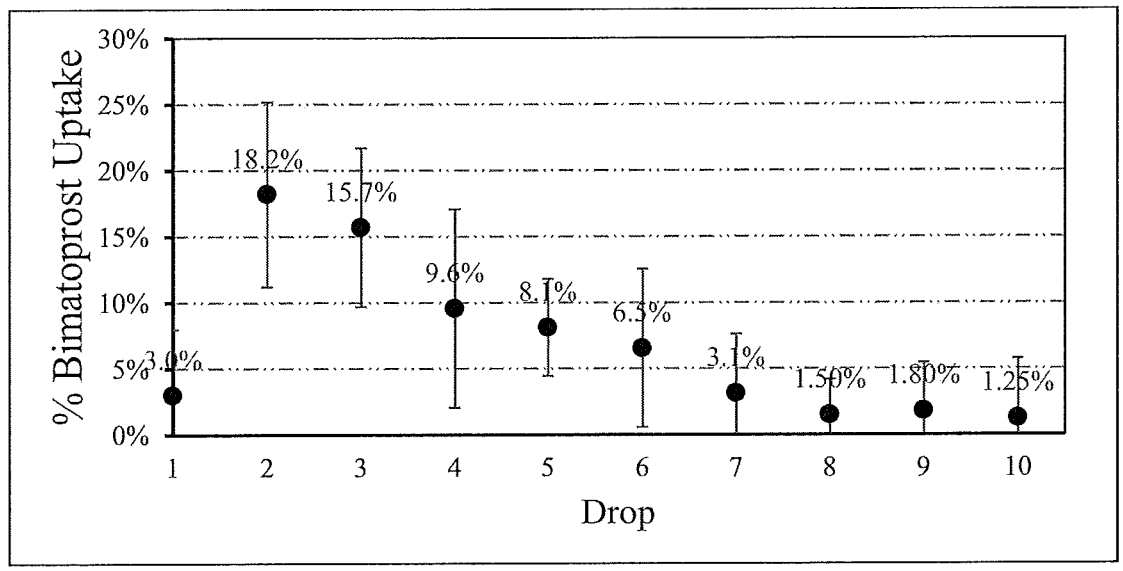
FIG. 32 shows uptake of drugs [A: bimatoprost at 250 µg mL$^{-1}$ and B: latanoprost at 50 µg mL$^{-1}$] from 0.1 g 60/40 methacrylic acid/DEGDMA particles. Particles were thermal-initiated.
Figure 32B:
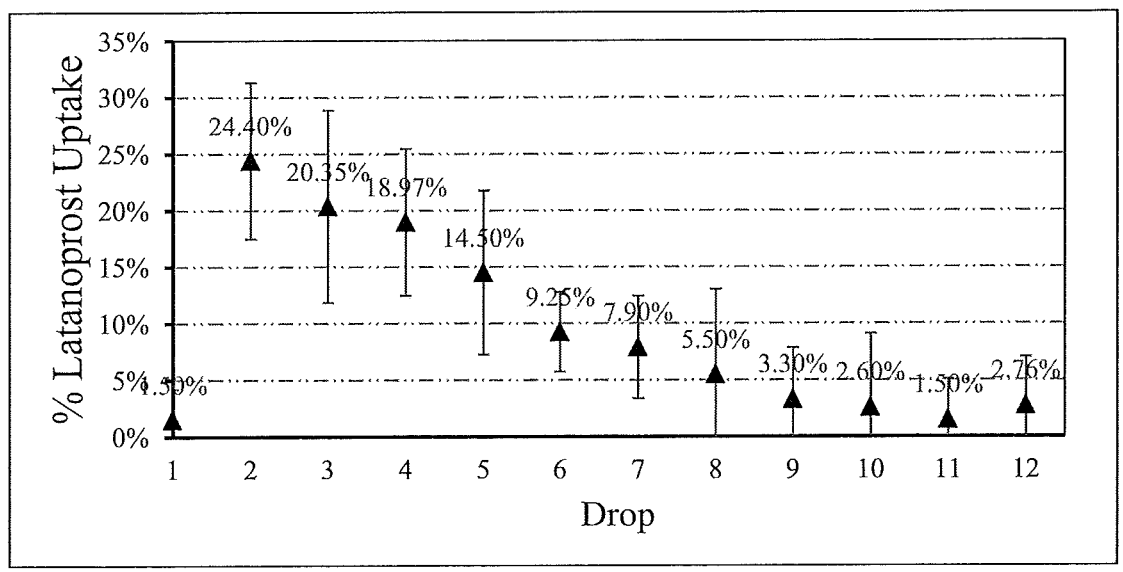
Figure 33:
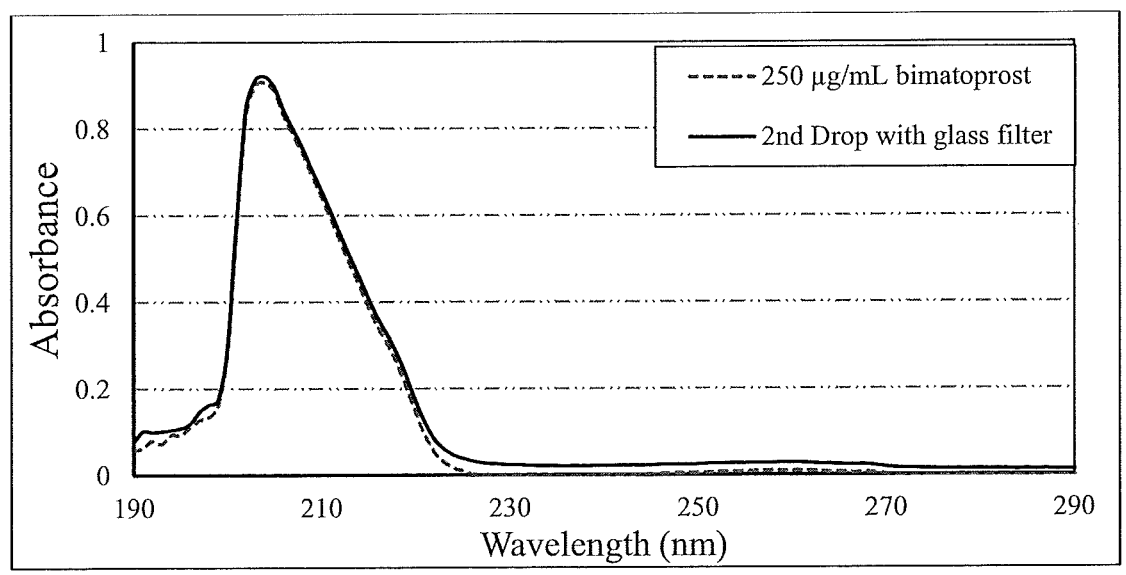
FIG. 33 shows spectra of 2nd drop (+24 hours from 1st drop) through 0.2 g glass bead filter compared to control.

Because of this high uptake. HEMA was completely removed from filter formulations. The high swelling of MAA led to higher amounts of cross-linker, so a hydrophilic cross-linker of DEGDMA was selected and added in weight fractions from 20% to 80%. Fractions above 50% cross-linker began to have insufficient uptake of BAK, most likely due to a decrease in dynamic time. A fraction of 60% MAA and 40% cross-linker was pursued. FIG. 31 shows that this filter has sufficient uptake of BAK (>95%). FIG. 32 shows that uptake of both drugs is reduced from previous cases, but the maximum uptake of 18%±7% (n=12) for bimatoprost and 24%±10% (n=9) for latanoprost were still above the acceptable limit. Filters of pure glass beads saw negligible uptake of bimatoprost (FIG. 33) and were mixed with 60/40 MAA/DEGDMA particles to attempt to reduce drug uptake.

Figure 34A:
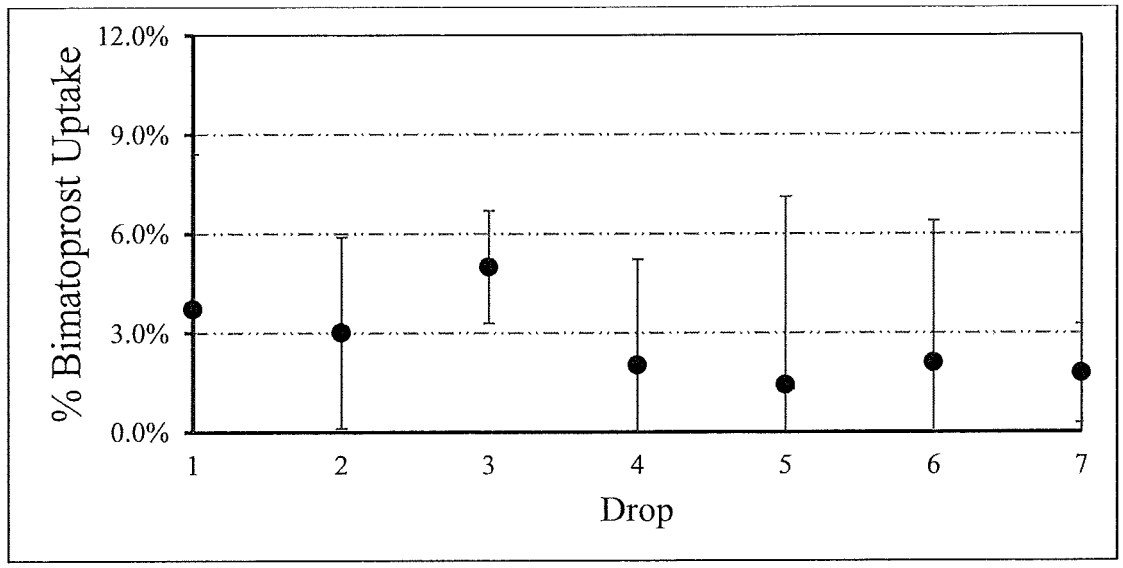
FIG. 34 shows uptake of drugs from particle/glass filters. A: Bimatoprost at 250 µg mL-1 with 0.15 g of 50/50 (60/40 methacrylic acid/DEGDMA)/glass filter. B: Latanoprost at 50 µg mL-1 with 0.15 g of 40/60 (60/40 methacrylic acid/DEGDMA)/glass filler. Particles were thermal-initiated.
Figure 34B:
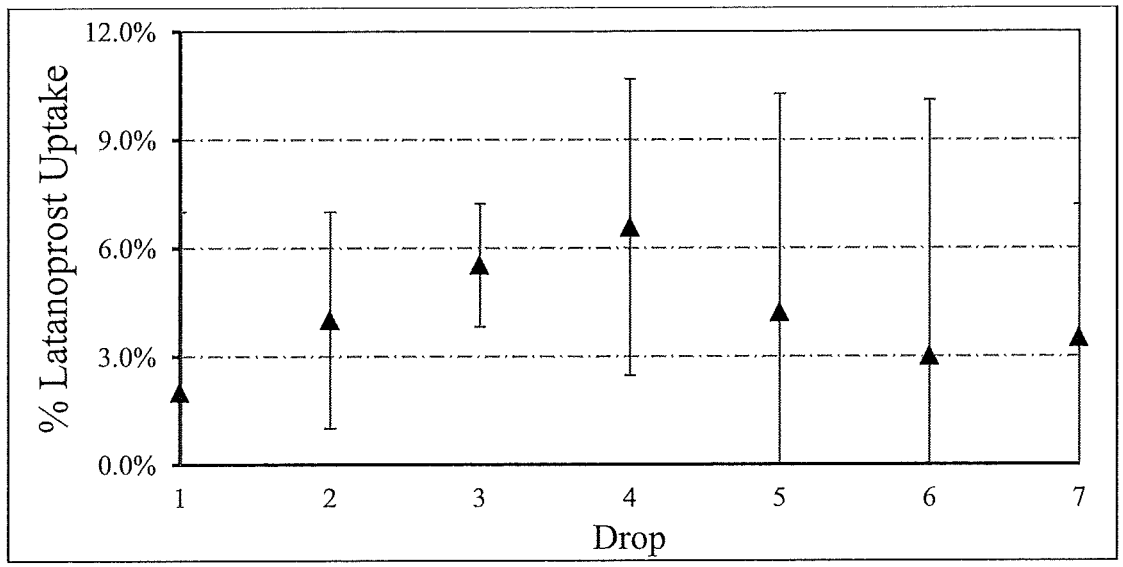
Figure 35:
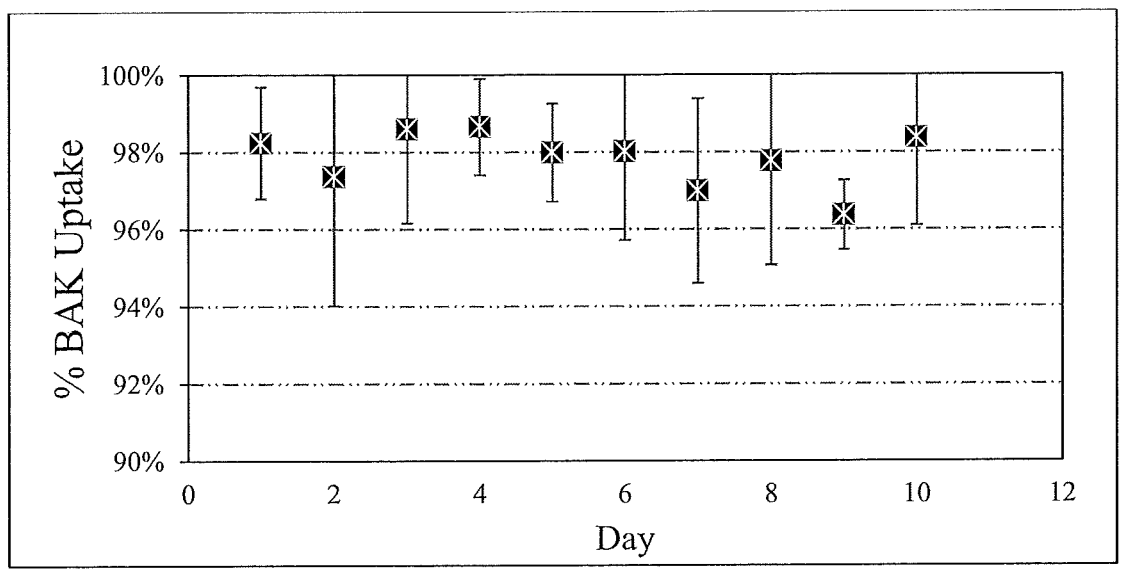
FIG. 35 shows uptake of benzalkonium chloride from 0.1 g 50/50 (60/40 MAA/DEDMGA particles)/glass. Particles were thermal-initiated.

FIG. 34 shows that drug uptake by the presence of glass beads was reduced for both drugs to <10%. Without intending to be bound by theory, this large reduction is believed to be, in part, because the glass beads do not leech material, meaning that the results reported without glass have more interference due to particle material and are thus over-reporting the uptake. FIG. 35 shows that BAK uptake (>95%) was still maintained with a 50/50 hydrogel/glass filter. However, the introduction of glass into the particles could have resulted in non-uniform mixing, so it is possible that such filters have inconsistent fractions of the two filter materials.

Size Analysis

Particles were sieved to collect particles in the range of 63-125 μm in diameter. The mesh of the 125 μm spacer was then used as a calibration curve to determine the average diameter of the particles.

FIG. 36 shows images of the 60/40 MAA/DEGDMA (thermos-initiated) particles and the 0.1 mm glass beads. The hydrogel particles are glassy in appearance and appear to be either spherical or shards of larger particles that were ground down to the specified size. An ImageJ analysis showed an average size of 94±15 μm in diameter. Many of the particles formed through thermos-initiation did not need crushing to fit through the 125 μm sieve.

Other hydrophilic monomers can also be investigated. Other hydrophilic contact lens monomers include N-vinyl-pyrrolidone (NVP) and N,N-dimethylacrylamide (DMA). A single, preliminary partition coefficient analysis showed NVP to have a higher uptake of BAK than MAA. A single run of a gel of 80% DMA, 20% SR-9035 was found to have a K for bimatoprost of 0.22.

Figure 37:
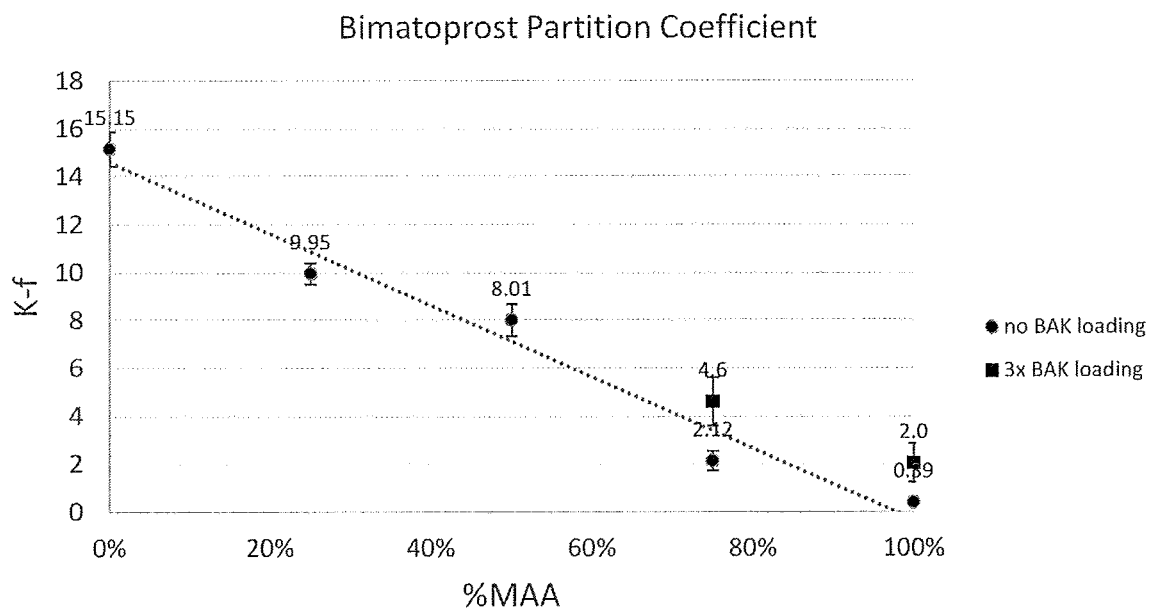
FIG. 37 is a plot of the partition coefficient of Bimatoprost in various copolymer compositions for particulate gels of HEMA and MAA.
Figure 38:
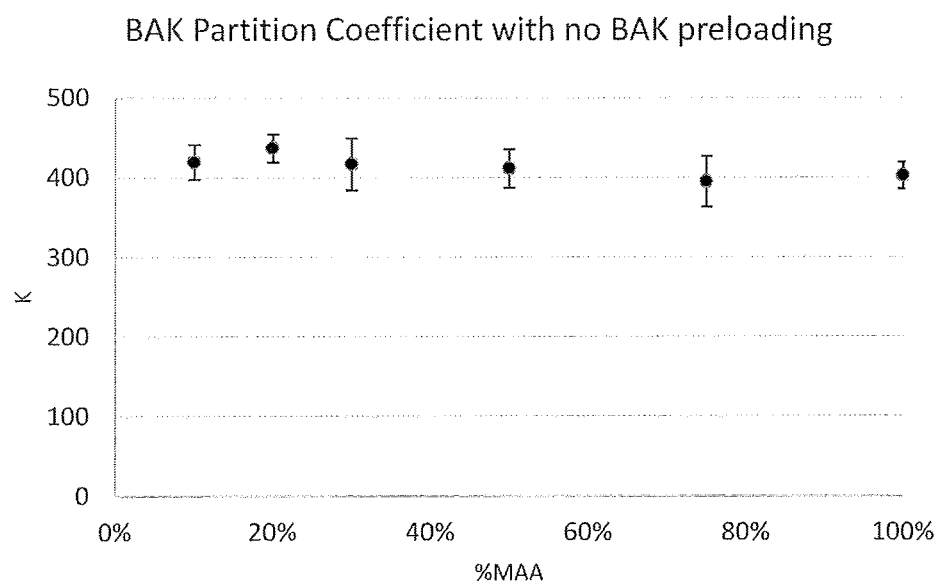
FIG. 38 is a plot of the partition coefficient of BAK in various copolymer compositions for particulate gels of HEMA and MAA.

BAK Removal from Bimatoprost Solutions by pHEMA-MMA Particles Integrated into Eye Drop Bottle Prototype Gels of pHEMA-MMA were synthesized using 2 mL monomer solution, 2.7 mL of water, 10 μL of ethylene glycol dimethacrylate as crosslinker, and 6 mg of Darocur TPO as a photoiniator. The monomer solution had different fractions of HEMA and MAA (i.e. 60% MAA would be 1.2 mL MAA and 0.8 mL HEMA). Gels were cured under UV light in 100 micron thick molds and subsequently cut into pieces approximately 50 mg in mass. Some gels were loaded with BAK to give a 3× (or 300 ppm) initial concentration and placed into 3 mL solution (either 0.025% bimatoprost/PBS 1× or 0.2% BAK/PBS). The concentrations in solution were measured using UV-vis spectrophotometry. Upon achieving equilibrium, the gels were placed in 3 mL blank PBS, and release was monitored by UV-vis spectrophotometry. Uptake and release equilibrium concentrations were used to calculate partition coefficients. FIGS. 37 and 38 are plots of the partition coefficient for bimatoprost and BAK for various gel copolymer compositions. At higher MAA concentrations the bimatoprost tends to remain in solution, whereas BAK strongly partitions into the gel for all gel copolymer compositions.

Bimatoprost Concentration in Eluting Drops from a Bottle Packed with 0.06 g of p-HEMA Particles A gel was prepared from 1.4 ml of HEMA monomer, 0.1 ml of a cross linker (SR9035), 12 ml of deionized (DI) water, and 20 μl of photo initiator Darocur® 1173 that were mixed in a 20-ml vial and put under UV light and constant stirring to produce particles. A filter tip was prepared by inserting in a layer of 11 micron pore size filter paper and 0.06 g of p-HEMA particles were placed into the filter tip. The particles were compressed and then covered with filter cloth. The bottle was then filled with 5 mL of 0.01% bimatoprost/PBS 1×.

Figure 39:
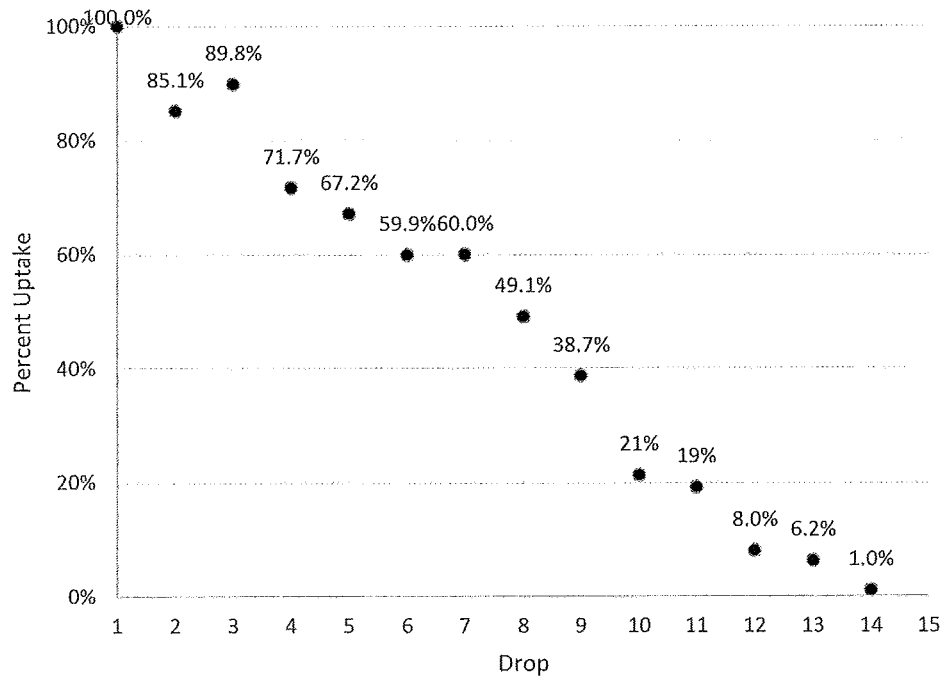
FIG. 39 is a plot of the percent uptake of Bimatoprost in particulate gels of HEMA and MAA from drops passed through the particles packed in a dropper tip.

A drop was dosed out and measured using UV-vis spectrophotometry and compared to a drop that did not pass through a filter to determine percent uptake of drug and BAK. As illustrated in FIG. 39, after dispensing of 14 drops, little or no additional bimatoprost absorbed in the gel particles.

Figure 40:
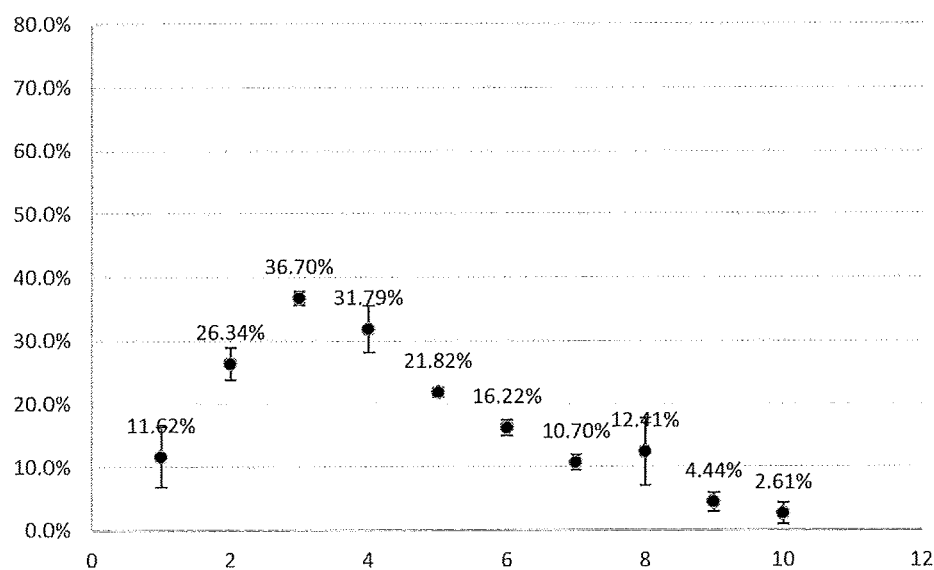
FIG. 40 is a plot of the percent uptake of Bimatoprost in particulate gels of HEMA and MAA from drops passed through the particles packed in a dropper tip.

Bimatoprost Concentration in Eluting Drops from a Bottle Packed with 0.1 g of 75:25 HEMA-MAA Particles A gel 75:25 HEMA-MAA was prepared using 0.35 mL of HEMA monomer, 1.05 mL of MAA monomer, 1 mL of a cross linker (SR9035), 12 mL of deionized (DI) water, and 20 μl of photo initiator Darocur® 1173 that were mixed in a 20-ml vial and put under UV light and constant stirring to produce particles. A filter tip was prepared by first inserting in a layer of 11 micron pore size filter paper and 0.06 g of p-HEMA particles. The particles were compressed and then covered with filter cloth. The bottle was then filled with 5 mL of 0.01% bimatoprost/PBS 1×. Drops was dosed out and measured by UV-vis spectrophotometry and the percent uptake was determined relative to that of a drop that did not pass through a filter. As illustrated in FIG. 40, after dispensing of 10 drops, little or no additional bimatoprost absorbed in the gel particles.

Figure 41:
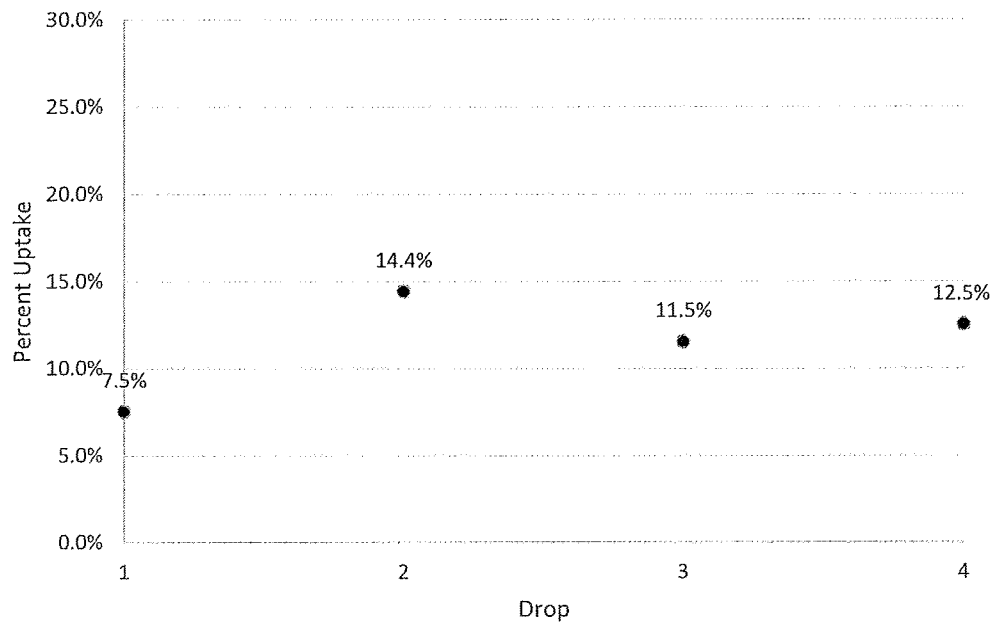
FIG. 41 shows a plot of the percent uptake of Bimatoprost in particulate gels of 25175 pMAA/tBM from drops passed through the particles packed in a dropper tip.

Bimatoprost Concentration in Eluting Drops from a Bottle Packed with 0.1 g of 75:25 HEMA-MAA Particles Loaded with 300 ppm BAK A gel 75:25 HEMA-MAA was prepared using 0.35 mL of HEMA monomer, 1.05 mL of MAA monomer, 1 mL of a cross linker (SR9035), 12 mL of deionized (DI) water, and 20 μl of photo initiator Darocur® 1173 that were mixed in a 20-ml vial and put under UV light and constant stirring to produce particles. A 1 g portion of the particles were placed into 3 g of 1×BAK/water solution. Full uptake of the BAK after 10 days yielded a concentration of 3× on the particles. A filter tip was prepared by first inserting in a layer of 11 micron pore size filter paper and 0.06 g of p-HEMA particles. The particles were compressed and then covered with filter cloth. The bottle was then filled with 5 mL of 0.01% bimatoprost/PBS 1×. Drops was dosed out and measured by UV-vis spectrophotometry and the percent uptake was determined relative to that of a drop that did not pass through a filter. As illustrated in FIG. 41, after dispensing of 8 drops, most bimatoprost passed the gel particles.

Partition Coefficient of Bimatoprost in 25:75 HEMA-MAA Gel Particles

A partition coefficient for bimatoprost in 25/75 pHEMA/MAA gels found that the gels had a very low partition coefficient (K) for bimatoprost of 0.2-0.1 and a partition coefficient of 0.5±0.2 with 3×BAK.

Bimatoprost Concentrations in Eluting Drops from a Bottle Packed with 0.1 g of 75:25 HEMA-MAA Gel Particles A gel was prepared from 1.5 mL tBM and 0.5 mL MAA, with 10 µL of diethylene glycol dimethacrylate and 6 mg of Darocur TPO upon curing in 50 micron thick molds under U V light. The polymerized mixture was pulverized into a fine powder. A filter tip was prepared by inserting in a layer of 11 micron pore size filter paper and placing 0.06 g of p-HEMA particles into filter tip. These particles were compressed and then covered with filter cloth. A bottle was then filled with 5 mL of 0.01% bimatoprost/PBS 1× and drops were dosed and measured using UV-vis spectrophotometry with comparison to a drop that was not passed through the filter. As shown in FIG. 41, only small amounts of bimatoprost were absorbed in the gel particles.

BAK Removal from Commercial Eye-Drop Formulations

Figure 42:
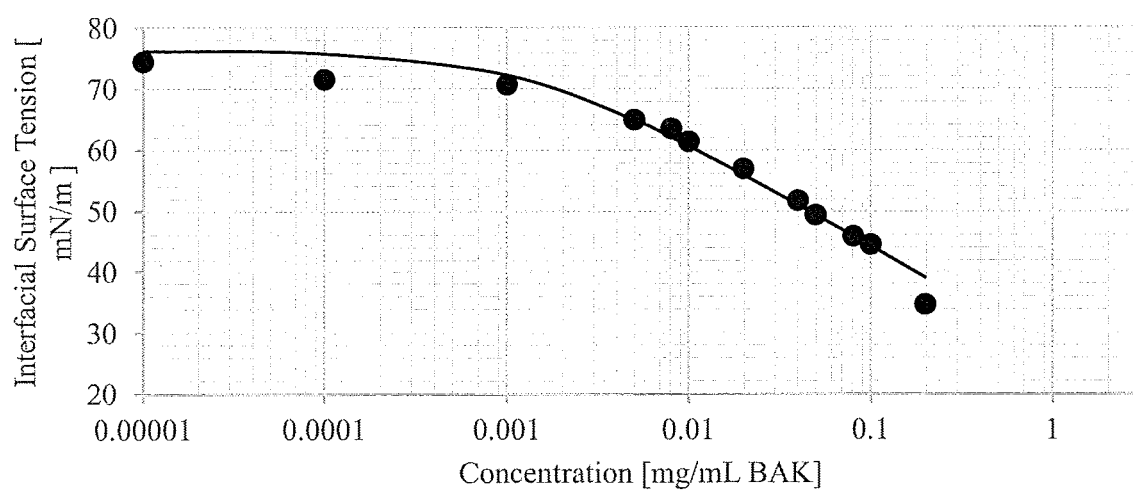
FIG. 42 is a plot of the equilibrium interfacial surface tension of BAK solutions that fits a Langmuir surfactant adsorption isotherm model for estimation of BAK concentrations.

An eye drop bottle's plug (tip) was packed with 0.1 g of p-HEMA particles for timolol Maleate commercial formulation (Sandoz Inc.) and 0.1 g of p-HEMA/MAA particles for bimatoprost commercial formation (Allegran Inc.). Approximately 0.5 mL of commercial formulation was dosed from the eye drop bottle for each measurement with 0.5 mL of a filtered formulation withdrawn by a standard 3 mL syringe for pendant drop measurements. A drop shape analysis was conducted by the Tensiometer to extract surface tension data of the filtered formulation. A calibration curve with equilibrium interfacial surface tension data as a function of BAK concentration was used to estimate concentrations and fractional BAK removal from the filtered eye drop formulation. Periodic surface tension measurements of the formulations were done to monitor fractional BAK removal. FIG. 42 shows the interfacial surface tension of that fits a Langmuir surfactant adsorption isotherm model that allows estimation of BAK concentrations by the surface tension.

The steady state Langmuir adsorption isotherm model and Langmuir surface equation of state were used to fit the equilibrium interfacial surface tension data are given below:

$$\Gamma_{eq} = \frac{[(\frac{\beta}{\alpha})\Gamma_\infty c]}{[(\frac{\beta}{\alpha})\Gamma_\infty c + 1]}$$

$$\gamma_0 - \gamma = -RT\Gamma_\infty \ln\left(1 - \frac{\Gamma_{eq}}{\Gamma_\infty}\right) \rightarrow \gamma_0 - \gamma = RT\Gamma_\infty \ln\left(1 + (\frac{\beta}{\alpha})c\right)$$

Where a least square error minimization protocol was used to fit the experimental equilibrium surface tension values and the calculated estimates using the above model. The fit parameters $r_\infty$ (maximum surface coverage) and $\beta/\alpha$ (ratio of kinetic rate constants) were estimated to be 0.003309 mol/m$^2$ and 462.14 m$^3$/mol respectively.

Benzalkonium Chloride Removal from Commercial Bimatoprost Formulation (Allegran Inc.)

Figure 43:
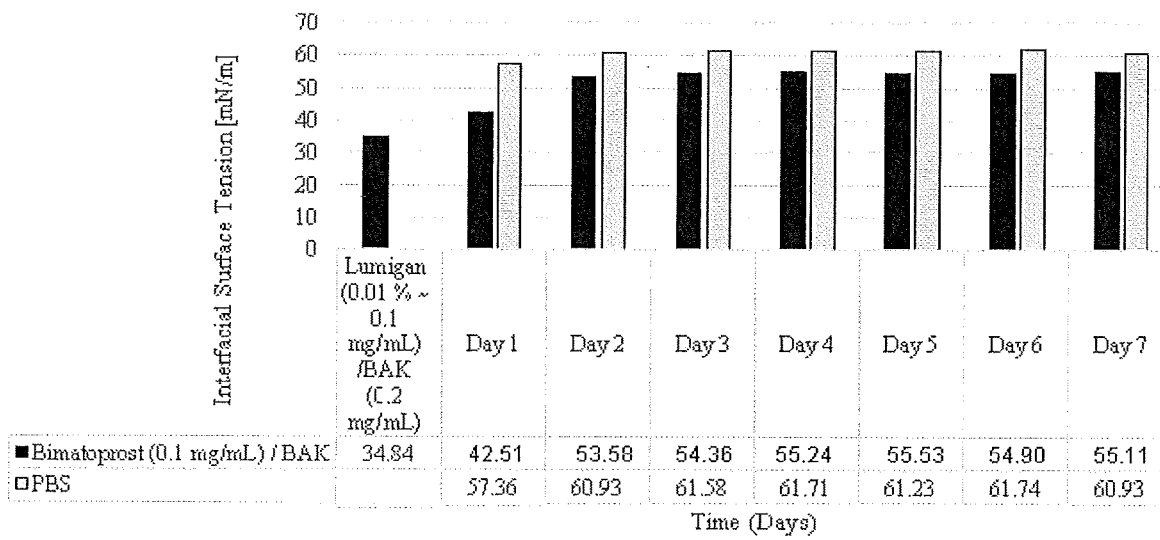
FIG. 43 shows a plot of the equilibrium interfacial surface tension data for commercial Bimatoprost/BAK solutions from Allegran over the period of a week.
Figure 44:
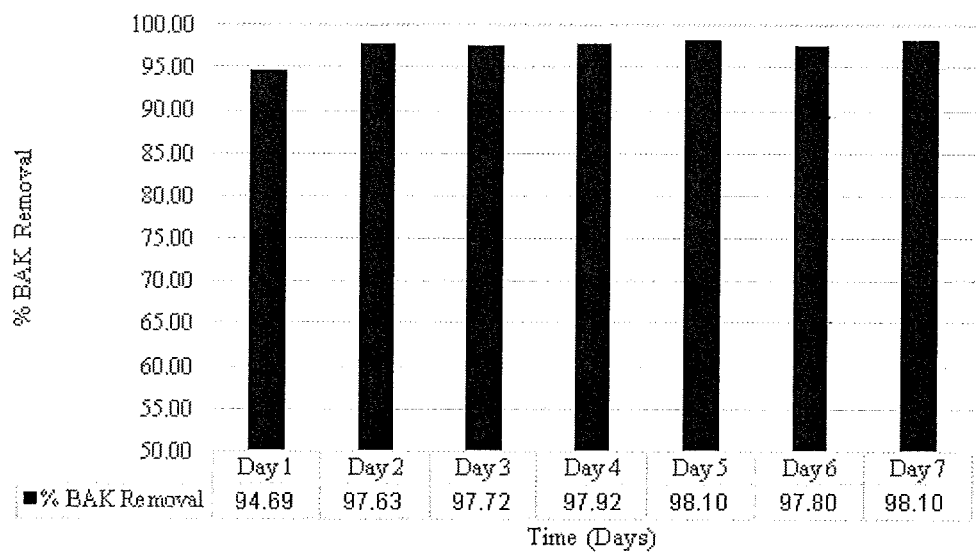
FIG. 44 shows a bar chart of the calculated BAK removal from equilibrium interfacial surface tension data for commercial Bimatoprost/BAK solutions from Allegran over the period of a week.

A particulate gel comprising 25 v/v % HEMA and 75 v/v % MAA was prepared and tested for the removal of BAK using a commercial bimatoprost formulation having 0.1 mg/mL bimatoprost and 0.2 mg/mL BAK in a pH 7±0.5 sodium phosphate buffer. FIG. 43 shows the interfacial surface tension measured for 15 drops of 33.33 µL and FIG. 44 the % BAK removed, measured using UV-vis spectrophotometry, from the solution on passing through a tip loaded with the pulverized particulate gel. The polymerized mixture was pulverized into a fine powder. Again high levels of BAK removal were observed.

A SOP for Drop Measurement is Below.

Single Eye Drop Measurement and Analysis by UV-Vis Spectrophotometry.

1. Purpose

This Standard Operating Procedure (SOP) describes the equipment and process used to analyze the concentration of a reagent (or multiple reagents) in a single drop released from an eye drop bottle. This SOP is applicable to eye drop bottles with or without filters. The quantification of the concentration in the eye drop allows for the calculation of percent uptake of the reagent by an inserted filter.

2. Materials
   2.1. Eye drop bottle
   22. Eye drop bottle tip (with or without filter)
   2.3. Eye drop bottle cap
   2.4. 0.5-5 mL Pipette (Fisherbrand Elite)
   2.5. 100-1000 µL Pipette (Fisherbrand Elite)
   2.6. 20-200 µL Pipette (Fisherbrand Elite)
   2.7. Pipette tips (Fisherbrand Elite)
   2.8. Micro Quartz Cuvette, White Wall, 0.4 mL, 10 mm, Cell, Cuvettes. Spectrometer, 1 cm (Science Outlet)
   2.9. Mass balance (Denver Instrument M-220D)
   2.10. UV-Vis Spectrophotometer (ThermoSpectronic Genesys 10UV)

3. Reagents
   3.1. Phosphate Buffered Saline, 1×[PBS] (Corning)
   3.2. Ethanol (200 proof, Fisher Scientific)
   3.3. De-Ionized Water [DI Water]
   3.4. Eye drop bottle formulation (varies per experiment)

4. Procedure
   4.1. Cleaning Cuvette
   This section's steps may be repeated throughout the procedure. When used, this section is referenced
      4.1.1. Remove any residual liquid inside of cuvette
      4.1.2. Fill cuvette with DI water, then empty cuvette
      4.1.3. Fill cuvette second time with DI water, then empty cuvette
      4.1.4. Fill cuvette with ethanol, then empty cuvette
      4.1.5. Fill cuvette with DI water, then empty cuvette
      4.1.6. Fill cuvette with DI water, then empty cuvette
      4.1.7. Air dry cuvette until dry
   4.2. Eye drop bottle assembly
      4.2.1. If not previously assembled, gather eye drop bottle, tip, and formulation
      4.2.2. Insert formulation into eye drop bottle
      4.2.3. Insert tip into bottle
      4.2.4. Cap bottle
      4.2.5. If equilibration is required, proceed to section 4.3. If not, skip to 4.4
   4.3. Equilibration (filter only)
   Equilibration allows for contact time between the formulation and the filter to saturate the filter with the desired reagent to prevent uptake during eye drop use.
      4.3.1. Carefully invert bottles so that cap and tip are pointed downward
      4.3.2. Mark start time and keep inverted for desired period of time
      4.3.3. Periodically examine bottles to ensure no leakage of formulation 4.3.4. After desired timespan, return eye drop bottles to upright position
4.3.5. Proceed to section 4.4 to measure eye drop
4.4. Eye Drop Measurement
4.4.1. Clean outside of cuvette with DI water
4.4.2. Follow section 4.1 for cleaning interior of cuvette
4.4.3. Fill cuvette with PBS
4.4.4. Insert cuvette into UV-vis spectrophotometer
4.4.5. Close UV-vis spectrophotometer and set blank
Note: Wavelength and UV-vis settings may depend upon formulation used
4.4.6. After blank is set, remove cuvette
4.4.7. Follow section 4.1 for cleaning procedure
4.4.8. Place clean cuvette on mass balance
4.4.9. Tare
4.4.10. Take eye drop bottle, invert, and hold over cuvette
4.4.11. Gently squeeze eye drop bottle until a single drop falls into the cuvette
4.4.12. Record mass of drop in cuvette
4.4.13. Return eye drop bottle to storage
4.4.14. Calculate required mass of PBS for dilution
Note: This amount of added PBS may vary based on desired dilution
4.4.15. Add required mass of PBS into cuvette using appropriate pipet and pipet tip, record added mass
4.4.16. Gently shake cuvette to mix
4.4.17. Place cuvette inside of UV-vis spectrophotometer
4.4.18. Close UV-vis and measure sample
4.4.19. Record data
4.4.20. Remove cuvette and clean following section 4.1.
4.4.21. If measuring second sample with same formulation, start at step 4.4.8

5. Data Analysis

This procedure collects the spectra of a diluted drop of formulation solution after exiting an eye drop bottle. In order to calculate the concentration, the spectra may be compared to a calibration curve, which is the measured spectrum of a known concentration solution. The two are compared to find the ratio between the spectra height of the measured curve and the calibration curve, which is the same ratio as their concentrations. For this procedure, the calibration curve was gathered by the procedure laid out in section 4.4, but on a solution of known concentration, usually the starting solution. This solution was not sent through any filter and showed the case of no uptake of solution. Once a drop has been measured and compared with the calibration curve, it can be converted into concentration, which, when accounting for dilution, can show the amount of drug taken up. This fraction of disappeared mass is considered the percent uptake by the filter.

Standard Operating Procedure for BAK Removal.
Purpose/Background

The purpose of this procedure is to provide information for evaluation of Benzalkonium chloride removal from commercial eye drop formulations. Commercial multi-dose ophthalmic formulations have an added preservative content, namely Benzalkonium chloride to maintain sterility of the formulation. A high frequency of administration of multi-dose formulation leads to an increase in systemic uptake of such preservatives. This causes irreversible damage to the cornea. A filter made from p-HEMA or p-HEMA/MAA particles is designed for delivering safe multi-dose preservative-free formulations. Since the concentration of BAK is significantly low in the filtered formulation, interfacial surface tension data is used to evaluate the fractional removal of preservative from the formulation. The procedure uses only a minimal amount of background in pendant drop tensiometer to follow the protocols, while at the same time a sufficiently complete description to perform detailed surface tension measurements used for evaluation of BAK removal.

Chemicals:
Monomer: 2-hydroxyethyl methacrylate (HEMA, 97%) monomer and Methacrylic acid (99%) from Sigma-Aldrich Chemicals (St. Louis, Mo. USA)
Crosslinker: ethoxylated (15) trimethylolpropane triacrylate (SR9035) obtained from Sartomer (Warrington, Pa., USA)
Photo-initiator: Photo-initiators Darocur® 1173 by Ciba Specialty Chemicals (Tarrytown, N.Y., USA)
Ethanol (200 proof) from Decon Laboratories Inc. (King of Prussia. Pa., USA)
Benzalkonium chloride from MP Biomedicals, LLC
De-ionized water Materials and Equipment:
Whatman® International limited filter paper size 1(11 cm diameter, 11 μm pore size)
Luer Lok tip syringes from BD, Franklin Lakes, N.J., USA
14-gauge, 1.5" precision applicator dispenser needle from Creative Hobbies
Standard 30 ml eye-drop bottle from Topwell Inc., Lexington, Ky., USA Procedures
Preparation of the Filter Bed
Detach the standard tip or plug of the designed eye drop bottle.
Check the plug (dropper tip) to make sure that it is not chipped or cracked.
Fill the plug's nozzle with two layers of filter paper. Make sure that the filter paper (pre-cut based on nominal diameter of the plug's nozzle) covers the nozzle. This is to ensure that finer particles from the packed filter are not dispensed along with the filtered eye-drop formulation.
Measure approximately 0.1 g of pre-made p-HEMA or p-HEMA/MAA particles. Pack the area beneath the plug's nozzle with the particles.
Cover the base of the plug with a layer of filter cloth to ensure that they stay intact within the plug.
Gently tap the layer of filter cloth with a tweezer to ensure that it stays intact near the plug's base.
Mount the filter/packed plug on to the eye-drop bottle's neck to complete the proposed design.
Make sure all eye-drop bottles are labelled with contents and the type of packed particles.

General Guidelines for Cleaning Particles
Detach the plug packed with particles from the designed eye drop bottle.
Transfer 10-15 ml of Dulbecco's phosphate buffered saline (PBS) into the eye drop bottle and mount the packed plug back on to the bottle.
Gently squeeze the eye-drop bottle to withdraw 10 ml of the transferred phosphate buffered saline from the eye-drop bottle. This step ensures that impurities in the filter bed gets leached out upon exposure to PBS.
Remove the cleaned filter from the designed eye drop bottle.
Rinse the eye-drop bottle with DI water and air-dry it prior transferring the eye-drop formulation.

Transfer 10-15 ml of commercial eye-drop formulation (0.01% Benzalkonium chloride) into the eye drop bottle and mount the cleaned filter back on to the bottle.

Guidelines Prior Surface Tension Measurements

Gently squeeze the eye-drop bottle with an embedded filter to withdraw 0.5 ml of the commercial eye-drop formulation. An initial dose of 0.5 ml is withdrawn to avoid dilution of the filtered formulation.

Dose out a volume of 0.5 mL (approximately 15 drops of 33 µl each) for measuring the surface tension of the filtered formulation. After a period of 24 hours, withdraw another batch of filtered formulation (0.5 mL) and monitor the surface tension of filtered formulation.

Standard 5 ml vial or a microplate is used for collecting the filtered formulation for surface tension measurements. Rinse the vial or the surface of the microplate with acetone and DI water prior collecting the dosed formulation.

Using a new Luer lock syringe and a needle, withdraw the dosed formulation from the vial or microplate.

Surface Tension Measurements Using Pendant Drop Tensiometer

This section is intended for users of DSA Kruss Pendant drop tensiometer and DSA v 1.9 Drop Shape Analyzer, helping them perform interfacial surface tension measurements.

Switch on the DSA100 Pendant drop tensiometer. At the time of writing, DSA v. 1.9 is the software package used to operate the tensiometer for surface tension measurements. Start the DSA1 software with shortcut symbol. The following illustration shows the user interface of the DSA software.

Ensure that the angle of inclination of the tilt is set to 0°

Select the following menu item FG>Acquire to set image transmission to live mode. Alternatively, the shortcut key F5 can also be used to do the same.

In the menu under Options, select in sequence the options Drop Type and Sub Type. Make sure that the drop type is selected as Pendant Drop [PD] and for subtype; the configuration of the drop is set as Top->Bottom.

Fit the Luer lock syringe containing the dosed formulation in the manual deposition system. The following illustration shows a pre-filled syringe positioned in the deposition system. If the tip of the syringe's plunger is misaligned with the deposition system, click on Refill tab under the DSA device control panel. This moves the position of the knob present in the deposition system upwards to allow space for the plunger.

Move the position of the needle downwards until it appears in the image. This can be done by adjusting the position of the scroll bar present in the device control panel. Alternatively, the position of the needle can also be controlled by the shortcut keys Page Up and Page Down.

Regulate lens zoom so that the image of the needle occupies the center of the frame. This is done by rotating the "Zoom" knob at the top left of the DSA 100 equipment. To adjust the sharpness of the image, click on Options>Focusing Assistant and tune the focus knob at the top left of the DSA100 equipment. The field "Median" is color coded and should appear in green, indicating a large numerical value. A good range for the median value is 75-80. Alternatively, the focal length can be adjusted by using the shortcut keys Home and End respectively.

Select the Dosing tab in the device control panel. The formulation in the syringe can be dosed out using the two action buttons present in the dosing tab. The direction of the arrows corresponds to the movement of the syringe plunger. Click on the button marked with up arrow to dose out a drop from the syringe.

Make sure that the dosing mode is set to continuous. The dosing speed can be entered by using the input field or the sliding controller. Since the volume of the filtered formulation in the syringe is only 0.5 mil, the recommended flow rates to be set is from 20-200 µl/min. A higher dosing speed is not suitable for drop production but only for emptying the contents in the syringe.

Adjust the zoom and needle height so that the drop occupies as much as 80% of the whole frame height. The image contains three colored lines. These lines define the region of drop curvature that the software uses to evaluate the surface tension of the formulation. They can be moved by keeping the mouse key pressed down.

Make sure that the top two lines are positioned within the region of the needle. The width of the needle is measured between these two lines. The lower line is placed slightly below the transition point between the formulation drop and the needle. The software uses the drop curvature below this line for evaluation of surface tension.

Manual Calibration based on needle width: A standard image of the drop contains 768 pixels with respect to a horizontal width of 8 inches of the image. The nominal outer diameter of the 14-gauge 1.5" precision needle used for the pendant drop measurements is 0.5144 mm. A custom software can be used to import the drop image and estimate the needle's width in inches. The scale of the image or magnification factor is calculated based on the needle diameter.

$$\text{Magnification factor } [MAG] = \frac{\text{Number of pixels contained in the image with respect to horizontal width } [768]}{\text{Horizontal width of the drop image } [8'']} \times \frac{\text{Needle width based on the region it occupies in the drop image } [x'']}{\text{Nominal outer diameter of the 14-gauge needle } [0.5144 \text{ mm}]} = Y \text{ pixels/mm}$$

In the menu under Options, click on Drop Info and check the values of parameters under their respective input fields. Make sure that the needle diameter and the calculated magnification factor are set to the right values. If the surface tension of the formulation is measured based on fluid-air interface, the density of the embedding phase is set to the density of air.

Once all the parameters are set, click on the symbol present in the symbol bar beneath the menu. DSA1 determines and extracts the drop shape which is indicated by a green/red contour surrounding the drop.

Click on the symbol in the symbol bar. The surface tension of the formulation is calculated using a Young-Laplace fit. The measured value appears in the Results window.

To monitor the surface tension of the formulation as a function time i.e., measure the dynamic surface tension of the formulation, click on Tracker-man under options. Enter the duration of the dynamic measurement and make sure that the following item "Extract Profile and Calculation" is checked. Start the feature to obtain the estimates of interfacial surface tension of the formulation at regular time intervals.

After a period of 24 hours, withdraw another batch of filtered formulation, 0.5 ml (approximately 15 drops of 33 µl each) and monitor the surface tension of filtered formulation. Repeat the measurements till 10 ml of the formulation is dosed out.

Below is a SOP for the preparation of hydrogel particles.

Preparation of Hydrogel Particles for Eye Drop Filters 1.0 Purpose

This SOP describes the production with multiple ratios of methacrylic acid (MAA) and 2-hydroxyethylmethacrylate (HEMA) to make particles for the uptake of benzalkonium chloride (BAK) in filter tips designed for ophthalmic drug solutions.

2.0 Reagents and Materials
  2.1 Chemicals
    2.1.1 Monomer: 2-hydroxyethyl methacrylate (HEMA, 97%) monomer and Methacrylic acid (99%) from Sigma-Aldrich Chemicals (St. Louis. Mo., USA).
    2.1.2 Crosslinker: ethylated (15) trimethylolpropane triacrylate (SR9035) obtained from Sartomer (Warrington, Pa., USA)
    2.1.3 Photo-initiator: Photo-initiators Darocur® 1173 by Ciba Specialty Chemicals (Tarrytown, N.Y., USA).
    2.1.4 Ethanol (200 proof) from Decon Laboratories Inc. (King of Prussia. Pa., USA).
    2.1.5 De-ionized water.
  2.2 Materials and equipment:
    2.2.1 liter beaker (Fisher Industries)
    2.2.2 Magnetic stirrer (approximately 5 cm*0.6 cm)
    2.2.3 Spatula
    2.2.4 Para-film (Bemis laboratory film 4'*4')
    2.2.5 Mortar (13 cm*5 cm) and pestle (13 cm*3 cm)
    2.2.6 Whatman® International limited filter paper size 1(11 cm diameter, 1 µm pore size)
    2.2.7 55×17 mm (diameter×height) Pyrex® petri dish.
    2.2.8 UVB-10 transilluminator (ULTRA.LUM INC, Carson, Calif., USA) with an intensity of 16.50 mW/cm$^2$ sharply peaked at 310 nm.
    2.2.9 Welch 2546B-01 Standard duty vacuum filter.
    2.2.10 Nalgene® 180 PVC non-toxic autoclavable LAB/FDA/USP VI grade (⅜" ID).
    2.2.11 Corning Pyrex® 125 ml micro-filter conical flask.
    22.12 Coors Coorstek® 320 ml 90 mm ceramic porcelain Buchner vacuum filter funnel.
3.0 Procedure
  3.1 Particle Preparation Steps (50 g batch size) (Monomer—100% HEMA)
    3.1.1 Mix 42 ml (1 T) of HEMA monomer, 3 ml (0.07 T) of crosslinker SR9035, 360 ml (8.5 T) of deionized (DI) water in a 1 liter beaker.
    3.1.2 Stir the mixture using a magnetic stirrer for 20 minutes at 900 rpm at room temperature.
    3.1.3 Deoxygenate the mixture by bubbling with pure nitrogen for 30 min.
    3.1.4 After the degassing step, add 300 µl (0.007 T) of photoinitiator Darocur® 1173.
    3.1.5 The mixture is then irradiated with UV light for 2 hours by a UVB-10 transilluminator (ULTRA-LUM INC, Carson. Calif. USA) with an intensity of 16.50 mW/cm$^2$ sharply peaked at 310 nm.
    3.1.6 During the UV curing, make sure that the top of the beaker is covered with parafilm sheet to avoid water evaporation and oxygenation. Also, the mixture is continuously stirred using a magnetic stirring bar at about 90 rpm.
    3.1.7 After the polymerization step, the mixture is stirred at about 1500 rpm (using big motor stirrer) to disintegrate the gel so formed.
    3.1.8 The gel is then separated from the solution by vacuum filtration method and washed with a large quantity of DI water.
    3.1.9 The gel is then left to dry for 24 hrs. at 130-140° F.
    3.1.10 Crush the gel so obtained using a mortar and pestle to obtain the particles.
  3.2 Particle Preparation Stems (50 g batch size) (Monomers—50% HEMA+50% Methacrylic Acid)
    3.2.1 Mix 42 ml (1 T) of the 2 monomers (21 ml HEMA+21 ml Methacrylic Acid), 3 ml (0.07 T) of crosslinker SR9035, 360 ml (8.5 T) of deionized (DI) water in a 1 liter beaker.
    3.2.2 Stir the mixture using a magnetic stirrer for 20 minutes at 900 rpm at room temperature.
    3.2.3 Deoxygenate the mixture by bubbling with pure nitrogen for 30 min.
    3.2.4 After the degassing step, add 300 µl (0.007 T) of photoinitiator Darocur® 1173.
    3.2.5 The mixture is then irradiated with UV light for 2 hours by a UVB-10 transilluminator (ULTRA. LUM INC, Carson, Calif., USA) with an intensity of 16.50 mW/cm$^2$ sharply peaked at 310 nm.
    3.2.6 During the UV curing, make sure that the top of the beaker is covered with parafilm sheet to avoid water evaporation and oxygenation. Also, the mixture is continuously stirred using a magnetic stirring bar at about 90 rpm.
    3.2.7 After the polymerization step, the mixture is stirred at about 1500 rpm (using big motor stirrer) to disintegrate the gel so formed.
    3.2.8 The gel is then separated from the solution by vacuum filtration method and washed with a large quantity of DI water.
    3.2.9 The gel is then left to dry for 24 hrs. at 130-140° F.
    3.2.10 Crush the gel so obtained using a mortar and pestle to obtain the particles.
  3.3 Particle Preparation Steps (50 g batch size) (Monomers—75% Methacrylic Add+25% HEMA)
    3.3.1 Mix 42 ml (1 T) of the 2 monomers (31.5 ml Methacrylic Acid+10.5 ml HEMA), 3 ml (0.07 T) of crosslinker SR9035, 360 ml (8.5 T) of deionized (DI) water in a 1 liter beaker.
    3.3.2 Stir the mixture using a magnetic stirrer for 20 minutes at 900 rpm at room temperature.
    3.3.3 Deoxygenate the mixture by bubbling with pure nitrogen for 30 min.
    3.3.4 After the degassing step, add 300 µl (0.007 T) of photoinitiator Darocur® 1173.
    3.3.5 The mixture is then irradiated with UV light for 2 hours by a UVB-10 transilluminator (ULTRA. LUM INC, Carson, Calif., USA) with an intensity of 16.50 mW/cm$^2$ sharply peaked at 310 nm.

3.3.6 During the UV curing, make sure that the top of the beaker is covered with parafilm sheet to avoid water evaporation and oxygenation. Also, the mixture is continuously stirred using a magnetic stirring bar at about 90 rpm.

3.3.7 After the polymerization step, the mixture is stirred at about 1500 rpm (using big motor stirrer) to disintegrate the gel so formed.

3.3.8 The gel is then separated from the solution by vacuum filtration method and washed with a large quantity of DI water.

3.3.9 The gel is then left to dry for 24 hrs. at 130-140° F.

3.3.10 Crush the gel so obtained using a mortar and pestle to obtain the particles.

3.4 Particle Cleaning Steps
(Common for all)

3.4.1 To remove the unreacted monomer part and other impurities, soak the freshly crushed particles in 800 ml (19 T) of ethanol for 2 days while stirring the mixture at 300 rpm using a magnetic stirrer. Make sure to change the solvent every day. Separate the particles from ethanol using vacuum filtration and dry them for 24 hrs. at 130-140° F.

3.4.2 After ethanol washing, soak the particles in 800 ml (19 T) of DI water for 4 days (changing water every day) while stirring the mixture at 300 rpm using a magnetic stirrer. Separate the particles from water using vacuum filtration and dry them for 24 hrs. at 130-140° F. to obtain the final cleaned particles.

Illustrative solutions, emulsions, or suspensions which can be used in aspects of the pharmaceutical formulation disclosed herein are shown in Tables 1 to 4. Example solutions, emulsions, or suspensions in the table below may be integrated into preservative removing devices and methods of removing a preservative of the present disclosure. One or more embodiments, variations, and examples of the preservative removing devices, matrices, and methods described herein may be incorporated into an eye drop dispensing system, which system may comprise a squeezable bottle. A squeezable bottle may comprise a reservoir in which a fluid may be stored. A fluid stored in the reservoir may comprise an embodiment, variation, or example of solutions, emulsions, or suspensions described herein, including those examples provided in Tables 7 to 10.

TABLE 7

Pharmaceuticals Sorted by Indication

| Market Name | Drug | % Active Ingredient | Formulation Type | Indication | Preservative |
|---|---|---|---|---|---|
| Dry Eye | | | | | |
| Restasis | Cyclosporine | 0.05% | emulsion | keratoconjunctivitis sicca | none |
| Xiidra | Lifitegrast | 5% | solution | keratoconjunctivitis sicca | none |
| Visine | Tetrahydrozoline | | | keratoconjunctivitis sicca | |
| Bacterial Infection | | | | | |
| Bleph 10 | sulfacetamide sodium | 10% | solution | conjunctivitis and other ocular infections | benzalkonium chloride 0.005% |
| Blephamide | sulfacetamide sodium - prednisolone acetate | 10%/0.2% | suspension | bacterial ocular infection | benzalkonium chloride 0.004% |
| Ocuflox | Ofloxacin | 0.3% | solution | bacterial ocular infection; corneal ulcers | benzalkonium chloride (0.005%) |
| Polytrim | polymyxin B sulfate and trimethoprim | polymyxin B sulfate 10,000 units/mL; trimethoprim sulfate equivalent to 1 mg/mL | solution | ocular bacterial infections; conjunctivitis; blepharoconjunctivitis | benzalkonium chloride 0.04 mg/mL |
| Zymaxid | Gatifloxacin | 0.3% and 0.5% | solution | bacterial conjunctivitis | benzalkonium chloride 0.005% |
| Zymar | Gatifloxacin | 0.3% | solution | bacterial conjunctivitis | benzalkonium chloride 0.005%; |
| Ciloxan | Ciprofloxacin | 0.3% | solution | bacterial conjunctivitis | None |
| Moxeza | Moxifloxacin | 0.5% | solution | bacterial conjunctivitis | none |
| Tobrex | Tobramycin | 0.3% | solution | infections of the eye and its adnexa caused by susceptible bacteria | benzalkonium chloride 0.01% |
| Vigamox | Moxifloxacin | 0.5% | solution | bacterial conjunctivitis | none |
| Iquix | Levofloxacin | 1.5% | solution | bacterial conjunctivitis | benzalkonium chloride 0.005% |

TABLE 7-continued

Pharmaceuticals Sorted by Indication

| Market Name | Drug | % Active Ingredient | Formulation Type | Indication | Preservative |
|---|---|---|---|---|---|
| Quixin | Levofloxacin | 0.5% | solution | bacterial conjunctivitis | benzalkonium chloride 0.005% |
| Glaucoma or Hypertension | | | | | |
| Alphagan | brimonidine tartrate | 0.01% | solution | open-angle glaucoma or ocular hypertension | Purite ® 0.005% (0.05 mg/mL) |
| Lumigan | Bimatroprost | 0.01% | solution | open angle glaucoma or ocular hypertension | benzalkonium chloride 0.2 mg/mL |
| Betagan | levobunolol hydrochloride | 0.5% | solution | chronic open-angle glaucoma or ocular hypertension | benzalkonium chloride 0.004% |
| Combigan | brimonidine tartrate/timolol maleate | 0.2%/0.5% | solution | glaucoma or ocular hypertension who require adjunctive or replacement therapy due to inadequately controlled IOP | benzalkonium chloride 0.005% |
| Azopt | Brinzolamide | 1% | suspension | ocular hypertension or open-angle glaucoma | benzalkonium chloride 0.1 mg |
| Betoptic S | betaxolol hydrochloride | 0.25% and 0.5% | suspension | ocular hypertension or chronic open angle glaucoma | benzalkonium chloride 0.1 mg in 1 mL |
| Isopto Carpine | pilocarpine hydrochloride | 1%, 2% and 4% | solution | IOP reduction; open-angle glaucoma or ocular hypertension; acute angle-closure glaucoma; induction of miosis | benzalkonium chloride 0.01% |
| Iopidine | Apraclonidine | 0.5% and 1.0% | solution | Short term adjunctive therapy in patients on maximally tolerated medical therapy who require additional IOP reduction | benzalkonium chloride 0.01% |
| Simbrinza | brinzolamide/ brimonidine tartrate | 1%/0.2% | suspension | reduction of elevated IOP in patients with open-angle glaucoma or ocular hypertension | benzalkonium chloride 0.03 mg |
| Travatan Z | Travoprost | 0.004% | solution | open-angle glaucoma or ocular hypertension who are intolerant of other intraocular pressure lowering medications | ionic buffered system, sofZia |
| Isralol | Timolol maleate | 0.5% | solution | ocular hypertension or open-angle glaucoma | benzalkonium chloride 0.05 mg/mL |
| Xalatan | Latanoprost | approximately 1.5 µg per drop | solution | open-angle glaucoma or ocular hypertension | benzalkonium chloride, 0.02% |
| Trusopt | dorzolamide hydrochloride | 2% | solution | ocular hypertension or open-angle glaucoma | benzalkonium chloride 0.0075% |
| Timoptic | timolol maleate | 0.25% and 0.5% | solution | ocular hypertension or open-angle glaucoma | benzalkonium chloride |
| Ziotan | Tafluprost | 0.0015% | solution | open-angle glaucoma or ocular hypertension | none |
| Vesneo | Latanoprostene Bunod | | | glaucoma | |
| Vyzulta | Latanoprostene Bunod | | | glaucoma | |

TABLE 7-continued

Pharmaceuticals Sorted by Indication

| Market Name | Drug | % Active Ingredient | Formulation Type | Indication | Preservative |
|---|---|---|---|---|---|
| Cosopt | Dorzolamide + Timolol | | | Glaucoma | |
| | | | Inflammation | | |
| Acular LS | ketorolac tromethamine | 0.4% | solution | ocular pain and burning/stinging following corneal refractive surgery | benzalkonium chloride 0.006% |
| Acular | ketorolac tromethamine | 0.5% | solution | inflammation following cataract surgery; relief of ocular itching due to seasonal allergic conjunctivitis | benzalkonium chloride 0.01% |
| Acuvail | ketorolac tromethamine | 0.45% | solution | treatment of pain and inflammation following cataract surgery | none |
| FML Forte | Fluorometholone | 0.25% | ointment | corticosteroid-responsive inflammation of the palpebral and bulbar conjunctiva, cornea and anterior segment of the globe | benzalkonium chloride 0.005% |
| FML | Fluorometholone | 0.1% | suspension | corticosteroid-responsive inflammation of the palpebral and bulbar conjunctiva, cornea and anterior segment of the globe | benzalkonium chloride 0.004% |
| Pred Forte | prednisolone acetate | 1% | suspension | steroid-responsive inflammation of the palpebral and bulbar conjunctiva, cornea, and anterior segment of the globe | benzalkonium chloride |
| Pred Mild | prednisolone acetate | 0.12% | suspension | mild to moderate noninfectious allergic and inflammatory disorders of the lid, conjunctiva, cornea, and sclera, including chemical and thermal burns | benzalkonium chloride |
| Pred-G | gentamicin and prednisolone acetate | 0.3%/1% | suspension | steroid-responsive inflammatory; bacterial infection; thermal burns or penetration of foreign bodies | Benzalkonium chloride 0.005% |
| Durezol | Difluprednate | 0.05% | emulsion | inflammation and pain associated with ocular surgery | sorbic acid 0.1% |
| Flarex | fluorometholone acetate | 0.1% | suspension | steroid-responsive inflammatory conditions of the palpebral and bulbar conjunctiva, cornea and anterior segment of the eye | benzalkonium chloride 0.01% |
| Ilevro | Nepafenac | 0.3% | suspension | pain and inflammation associated with cataract surgery | benzalkonium chloride 0.005% |

TABLE 7-continued

Pharmaceuticals Sorted by Indication

| Market Name | Drug | % Active Ingredient | Formulation Type | Indication | Preservative |
|---|---|---|---|---|---|
| Maxidex | Dexamethasone | 0.1% | suspension | Steroid responsive inflammatory conditions; corneal injury from chemical, radiation, or thermal burns, or penetration of foreign bodies | benzalkonium chloride 0.01% |
| Maxitrol | neomycin and polymyxin B sulfates and dexamethasone | neomycin sulfate equivalent to neomycin 3.5 mg, polymyxin B sulfate 10,000 units, dexamethasone 0.1% | solution | steroid-responsive inflammatory ocular conditions for which a corticosteroid is indicated and where bacterial infection or a risk of bacterial ocular infection exists | methylparaben 0.05%, propylparaben 0.01% |
| Nevanac | Nepafenac | 0.1% | suspension | pain and inflammation associated with cataract surgery | benzalkonium chloride 0.005% |
| Omnipred | prednisolone acetate | 1.0% | suspension | steroid responsive inflammatory conditions; corneal injury from chemical, radiation, or thermal burns, or penetration of foreign bodies | benzalkonium chloride 0.01% |
| Tobradex ST | tobramycin/ dexamethasone | 0.3%/0.05% | suspension | steroid-responsive inflammatory ocular conditions for which a corticosteroid is indicated and where superficial bacterial ocular infection exists | benzalkonium chloride 0.1 mg |
| Voltaren Ophthalmic | diclofenac sodium | 0.1% | solution | inflammation from cataract extraction; temporary relief of pain and photophobia following corneal refractive surgery | None |
| Bromday | Bromfenac | 0.09% | solution | postoperative inflammation in patients who have undergone cataract extraction | benzalkonium chloride 0.05 mg/mL |
| Xibrom | Bromfenac | 0.09% | solution | postoperative inflammation in patients who have undergone cataract extraction | benzalkonium chloride (0.05 mg/mL) |
| Xibrom | Bromfenac | 0.09% | solution | postoperative inflammation in patients who have undergone cataract extraction | benzalkonium chloride 0.05 mg/mL |
| Allergic Conjunctivitis | | | | | |
| Alocril | nedocromil sodium | 2% | solution | itching associated with allergic conjunctivitis | benzalkonium chloride 0.01% |
| Elestat | epinastine HCl | 0.05% | suspension | itching associated with allergic conjunctivitis | Benzalkonium chloride 0.01%; |
| Lastacaft | Alcaftadine | 0.25% | solution | itching associated with allergic conjunctivitis | benzalkonium chloride 0.005% |

TABLE 7-continued

Pharmaceuticals Sorted by Indication

| Market Name | Drug | % Active Ingredient | Formulation Type | Indication | Preservative |
|---|---|---|---|---|---|
| Alomide | lodoxamide tromethamine | 0.1% | solution | vernal keratoconjunctivitis; giant papillary conjunctivitis; allergic/atopic conjunctivitis | benzalkonium chloride 0.007% w/v |
| Emadine | emedastine difumarate | 0.5% | solution | allergic conjunctivitis | benzalkonium chloride, 0.01% |
| Pataday | olopatadine hydrochloride | 0.2% | solution | ocular itching associated with allergic conjunctivitis | benzalkonium chloride 0.01% |
| Pazeo | olopatadine hydrochloride | 0.7% | solution | ocular itching associated with allergic conjunctivitis | benzalkonium chloride 0.015% |
| Hair Growth | | | | | |
| Latisse | Bimatoprost | 0.03% | solution | hypotrichosis of the eyelashes | benzalkonium chloride 0.05 mg/mL |
| Local Anesthetic | | | | | |
| Alcaine | proparacaine hydrochloride | 0.5% | solution | topical anesthesia - removal of foreign bodies; measurement of intraocular pressure; conjunctive scraping procedures | benzalkonium chloride 0.01% |
| Tetracaine | Tetracaine hydrochloride | 0.5% | solution | procedures requiring a rapid and short acting topical ophthalmic anesthetic | None |
| Pupil Dilation | | | | | |
| Cyclogyl | cyclopentolate hydrochloride | 0.5%, 1.0% or 2.0% | solution | pre- and post-operative states when mydriasis is required and when a shorter acting mydriatic and cycloplegic is needed in the therapy of iridocyclitis | Benzalkonium chloride 0.1 mg in 1.0 mL |
| Cyclomydril | cyclopentolate hydrochloride and phenylephrine hydrochloride | 0.2%/1.0% | solution | For the production of mydriasis (pupil dilation) | Benzalkonium chloride 0.01% |
| Isopto Atropine | atropine sulfate | 1% | solution | mydriasis; cycloplegia; penalization of the healthy eye in the treatment of amblyopia | benzalkonium chloride 0.01% |
| Mydriacyl | Tropicamide | 0.5% or 1.0% | solution | mydriasis and cycloplegia | benzalkonium chloride 0.01% |
| Fungal infection | | | | | |
| Natacyn | Natamycin | 5% | suspension | anti-fungal; fungal blepharitis, conjunctivitis, and keratitis | benzalkonium chloride 0.02% |

TABLE 8

Experimental Presbyopia Formulations.

| Drug Code | Drug | % Active Ingredient | Formulation Type | Indication | Preservative |
|---|---|---|---|---|---|
| Presbyopia | | | | | |
| EV06/ UNR844 | lipoic acid choline ester chloride | 3.0% | solution | presbyopia | benzalkonium chloride, 0.01% |
| PRX-100 | aceclidine/ tropicamide | 0.25-2.0%/ 0.025-0.1% | Solution or suspension | presbyopia | benzalkonium chloride, 0.02% |
| CSF-1 | sodium hyaluronate/ diclofenac sodium/ pilocarpine HCl | 0.1-0.9%/ 0.006-0.012%/ 0.2-0.4% | Solution or suspension | presbyopia | Any, benzalkonium chloride, 0.01% |
| AAGN-199201 | Pilocarpine and/or oxymetazoline | 0.1%-1% | Solution or suspension | presbyopia | Any, benzalkonium chloride, 0.01% |
| AAGN-190584 | keterolac | 0.1%-1% | Solution or suspension | presbyopia | Any, benzalkonium chloride, 0.01% |

TABLE 9

Additional Pharmaceuticals

| Market Name | Drug | % Active Ingredient | Formulation Type | Indication | Preservative |
|---|---|---|---|---|---|
| Restasis | cyclosporine | 0.05% | emulsion | keratoconjunctivitis sicca | none |
| Latisse | bimatoprost | 0.03% | solution | hypotrichosis of the eyelashes | benzalkonium chloride 0.05 mg/mL |
| Alphagan | brimonidine Tartrate | 0.01% | solution | open-angle glaucoma or ocular hypertension | Purite ® 0.005% (0.05 mg/mL) |
| Lumigan | bimatroprost | 0.01% | solution | open angle glaucoma or ocular hypertension | benzalkonium chloride 0.2 mg/mL |
| Acular LS | ketorolac tromethamine | 0.4% | solution | ocular pain and burning/stinging following corneal refractive surgery | benzalkonium chloride 0.006% |
| Acular | ketorolac tromethamine | 0.5% | solution | inflammation following cataract surgery; relief of ocular itching due to seasonal allergic conjunctivitis | benzalkonium chloride 0.01% |
| Acuvail | ketorolac tromethamine | 0.45% | solution | treatment of pain and inflammation following cataract surgery | none |
| Alocril | nedocromil sodium | 2% | solution | itching associated with allergic conjunctivitis | benzalkonium chloride 0.01% |
| Betagan | levobunolol hydrochloride | 0.5% | solution | chronic open-angle glaucoma or ocular hypertension | benzalkonium chloride 0.004% |
| Bleph 10 | sulfacetamide sodium | 10% | solution | conjunctivitis and other ocular infections | benzalkonium chloride 0.005% |
| Blephamide | sulfacetamide sodium-prednisolone acetate | 10%/0.2% | suspension | bacterial ocular infection | benzalkonium chloride 0.004% |

TABLE 9-continued

Additional Pharmaceuticals

| Market Name | Drug | % Active Ingredient | Formulation Type | Indication | Preservative |
|---|---|---|---|---|---|
| Combigan | brimonidine tartrate/timolol maleate | 0.2%/0.5% | solution | glaucoma or ocular hypertension who require adjunctive or replacement therapy due to inadequately controlled iop | benzalkonium chloride 0.005% |
| Elestat | epinastine HCl | 0.05% | suspension | itching associated with allergic conjunctivitis | benzalkonium chloride 0.01%; |
| FML Forte | fluorometholone | 0.25% | ointment | corticosteroid-responsive inflammation of the palpebral and bulbar conjunctiva, cornea and anterior segment of the globe | benzalkonium chloride 0.005% |
| FML | fluorometholone | 0.1% | suspension | corticosteroid-responsive inflammation of the palpebral and bulbar conjunctiva, cornea and anterior segment of the globe | benzalkonium chloride 0.004% |
| Lastacaft | alcaftadine | 0.25% | solution | itching associated with allergic conjunctivitis | benzalkonium chloride 0.005% |
| Ocuflox | ofloxacin | 0.3% | solution | bacterial ocular infection; corneal ulcers | benzalkonium chloride (0.005%) |
| Polytrim | polymyxin B sulfate and trimethoprim | polymyxin B sulfate 10,000 units/mL; trimethoprim sulfate equivalent to 1 mg/mL | solution | ocular bacterial infections; conjunctivitis; blepharo-conjunctivitis | benzalkonium chloride 0.04 mg/mL |
| Pred Forte | prednisolone acetate | 1% | suspension | steroid-responsive inflammation of the palpebral and bulbar conjunctiva, cornea, and anterior segment of the globe | benzalkonium chloride |
| Pred Mild | prednisolone acetate | 0.12% | suspension | mild to moderate noninfectious allergic and inflammatory disorders of the lid, conjunctiva, cornea, and sclera, including chemical and thermal burns | benzalkonium chloride |
| Pred-G | gentamicin and prednisolone acetate | 0.3%/1% | suspension | steroid-responsive inflammatory; bacterial infection; thermal burns or penetration of foreign bodies | benzalkonium chloride 0.005% |
| Zymaxid | gatifloxacin | 0.3% and 0.5% | solution | bacterial conjunctivitis | benzalkonium chloride 0.005% |
| Zymar | gatifloxacin | 0.3% | solution | bacterial conjunctivitis | benzalkonium chloride 0.005%; |
| Alcaine | proparacaine hydrochloride | 0.5% | solution | topical anesthesia-removal of foreign bodies; measurement of intraocular pressure; conjunctive scraping | benzalkonium chloride 0.01% |

TABLE 9-continued

Additional Pharmaceuticals

| Market Name | Drug | % Active Ingredient | Formulation Type | Indication | Preservative |
|---|---|---|---|---|---|
| Alomide | lodoxamide tromethamine | 0.1% | solution | vernal keratoconjunctivitis; giant papillary conjunctivitis; allergic/atopic conjunctivitis | benzalkonium chloride 0.007% w/v |
| Azopt | brinzolamide | 1% | suspension | ocular hypertension or open-angle glaucoma | benzalkonium chloride 0.1 mg |
| Betoptic S | betaxolol hydrochloride | 0.25% and 0.5% | suspension | ocular hypertension or chronic open angle glaucoma | benzalkonium chloride 0.1 mg in 1 mL |
| Ciloxan | ciprofloxacin | 0.3% | solution | bacterial conjunctivitis | None |
| Cyclogyl | cyclopentolate hydrochloride | 0.5%, 1.0% or 2.0% | solution | pre- and post-operative states when mydriasis is required and when a shorter acting mydriatic and cycloplegic is needed in the therapy of iridocyclitis | benzalkonium chloride 0.1 mg in 1.0 mL |
| Cyclomydril | cyclopentolate hydrochloride and phenylephrine hydrochloride | 0.2%/1.0% | solution | for the production of mydriasis (pupil dilation) | benzalkonium chloride 0.01% |
| Durezol | difluprednate | 0.05% | emulsion | inflammation and pain associated with ocular surgery | sorbic acid 0.1% |
| Emadine | emedastine difumarate | 0.5% | solution | allergic conjunctivitis | benzalkonium chloride, 0.01% |
| Flarex | fluorometholone acetate | 0.1% | suspension | steroid-responsive inflammatory conditions of the palpebral and bulbar conjunctiva, cornea and anterior segment of the eye | benzalkonium chloride 0.01% |
| Ilevro | nepafenac | 0.3% | suspension | pain and inflammation associated with cataract surgery | benzalkonium chloride 0.005% |
| Iopidine | apraclonidine | 0.5% and 1.0% | solution | short term adjunctive therapy in patients on maximally tolerated medical therapy who require additional iop reduction | benzalkonium chloride 0.01% |
| Isopto Atropine | atropine sulfate | 1% | solution | mydriasis; cycloplcgia; penalization of the healthy eye in the treatment of amblyopia | benzalkonium chloride 0.01% |
| Isopto Carpine | pilocarpine hydrochloride | 1%, 2% and 4% | solution | iop reduction; open-angle glaucoma or ocular hypertension; acute angle-closure glaucoma; induction of miosis | benzalkonium chloride 0.01% |
| Maxidex | dexamethasone | 0.1% | suspension | steroid responsive inflammatory conditions; corneal injury from chemical, radiation, or thermal burns, or penetration of foreign bodies | benzalkonium chloride 0.01% |

TABLE 9-continued

Additional Pharmaceuticals

| Market Name | Drug | % Active Ingredient | Formulation Type | Indication | Preservative |
|---|---|---|---|---|---|
| Maxitrol | neomycin and polymyxin B sulfates and dexamethasone | neomycin sulfate equivalent to neomycin 3.5 mg, polymyxin B sulfate 10,000 units, dexamethasone 0.1% | solution | steroid-responsive inflammatory ocular conditions for which a corticosteroid is indicated and where bacterial infection or a risk of bacterial ocular infection exists | methylparaben 0.05%, propylparaben 0.01% |
| Moxeza | moxifloxacin | 0.5% | solution | bacterial conjunctivitis | None |
| Mydriacyl | tropicamide | 0.5% or 1.0% | solution | mydriasis and cycloplegia | benzalkonium chloride 0.01% |
| Natacyn | natamycin | 5% | suspension | anti-fungal; fungal blepharitis, conjunctivitis, and keratitis | benzalkonium chloride 0.02% |
| Nevanac | nepafenac | 0.1% | suspension | pain and inflammation associated with cataract surgery | benzalkonium chloride 0.005% |
| Omnipred | prednisolone acetate | 1.0% | suspension | steroid responsive inflammatory conditions; corneal injury from chemical, radiation, or thermal burns, or penetration of foreign bodies | benzalkonium chloride 0.01% |
| Pataday | olopatadine hydrochloride | 0.2% | solution | ocular itching associated with allergic conjunctivitis | benzalkonium chloride 0.01% |
| Pazeo | olopatadine hydrochloride | 0.7% | solution | ocular itching associated with allergic conjunctivitis | benzalkonium chloride 0.015% |
| Simbrinza | brinzolamide/ brimonidine tartrate | 1%/0.2% | suspension | reduction of elevated iop in patients with open-angle glaucoma or ocular hypertension | benzalkonium chloride 0.03 mg |
| Tetracaine | hydrochloride | 0.5% | solution | procedures requiring a rapid and shortacting topical ophthalmic anesthetic | None |
| Tobradex ST | tobramycin/ dexamethasone | 0.3%/0.05% | suspension | steroid-responsive inflammatory ocular conditions for which a corticosteroid is indicated and where superficial bacterial ocular infection exists | benzalkonium chloride 0.1 mg |
| Tobrex | tobramycin | 0.3% | solution | infections of the eye and its adnexa caused by susceptible bacteria | benzalkonium chloride 0.01% |
| Travatan Z | travoprost | 0.004% | solution | open-angle glaucoma or ocular hypertension who are intolerant of other intraocular pressure lowering medications | ionic buffered system, sofZia |
| Vigamox | moxifloxacin | 0.5% | solution | bacterial conjunctivitis | None |

TABLE 9-continued

Additional Pharmaceuticals

| Market Name | Drug | % Active Ingredient | Formulation Type | Indication | Preservative |
|---|---|---|---|---|---|
| Voltaren Ophthalmic | diclofenac sodium | 0.1% | solution | inflammation from cataract extraction; temporary relief of pain and photophobia following corneal refractive surgery | None |
| Trusopt | dorzolamide hydrochloride | 2% | solution | ocular hypertension or open-angle glaucoma | benzalkonium chloride 0.0075% |
| Timoptic | timolol maleate | 0.25% and 0.5% | solution | ocular hypertension or open-angle glaucoma | benzalkonium chloride |
| Ziotan | tafluprost | 0.0015% | solution | open-angle glaucoma or ocular hypertension | none |
| Xalatan | latanoprost | approximately 1.5 µg per drop | solution | open-angle glaucoma or ocular hypertension | benzalkonium chloride, 0.02% |
| Bromday | bromfenac | 0.09% | solution | postoperative inflammation in patients who have undergone cataract extraction | benzalkonium chloride 0.05 mg/mL |
| Isralol | timolol maleate | 0.5% | solution | ocular hypertension or open-angle glaucoma | benzalkonium chloride 0.05 mg/mL |
| Xibrom | bromfenac | 0.09% | solution | postoperative inflammation in patients who have undergone cataract extraction | benzalkonium chloride (0.05 mg/mL) |
| Iquix | levofloxacin | 1.5% | solution | bacterial conjunctivitis | benzalkonium chloride 0.005% |
| Quixin | levofloxacin | 0.5% | solution | bacterial conjunctivitis | benzalkonium chloride 0.005% |
| Xibrom | bromfenac | 0.09% | solution | postoperative inflammation in patients who have undergone cataract extraction | benzalkonium chloride 0.05 mg/mL |
| Xiidra | lifitegrast | 5% | solution | Dry Eye | None |

TABLE 10

Other Pharmaceuticals

| Code of Drug in Clinical Trial | Drug | % Active Ingredient | Formulation Type | Indication | Preservative |
|---|---|---|---|---|---|
| EV06/ UNR844 | lipoic acid choline ester chloride | 3.0% | solution | presbyopia | benzalkonium chloride, 0.01% |
| PRX-100 | aceclidine/ tropicamide | 0.25-2.0%/ 0.025-0.1% | Solution or suspension | presbyopia | benzalkonium chloride, 0.02% |
| SF-1 | sodium hyaluronate/ diclofenac sodium/ pilocarpine HCl | 0.1-0.9%/ 0.006-0.012%/ 0.2-0.4% | Solution or suspension | presbyopia | Any, benzalkonium chloride, 0.01% |
| ECF843 | | 0.1%-1% | Solution or suspension | Dry eye | Any, benzalkonium chloride, 0.01% |

TABLE 10-continued

Other Pharmaceuticals

| Code of Drug in Clinical Trial | Drug | % Active Ingredient | Formulation Type | Indication | Preservative |
|---|---|---|---|---|---|
| None | rebamipide | 1%, 2% | solution | Dry eye (keratoconjunctivitis sicca) | Any, benzalkonium chloride, 0.01% |
| AAGN-199201 | Pilocarpine and/or oxymetazoline | 0.1%-1% | Solution or suspension | presbyopia | Any, benzalkonium chloride, 0.01% |
| AAGN-190584 | keterolac | 0.1%-1% | Solution or suspension | presbyopia | Any, benzalkonium chloride, 0.01% |
|  | pilocarpine | 0.3% | Solution or suspension | presbyopia | Any, benzalkonium chloride, 0.01% |
|  | pilocarpine | varies with severity of presbyopia, 0.3%-2.2% | Solution or suspension | presbyopia | Any, benzalkonium chloride, 0.01% |

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A preservative removing device, comprising microparticles of a copolymer comprising a least one hydrophilic repeating unit and at least one hydrophobic repeating unit, wherein the microparticles are rigid aggregates,
wherein the at least one hydrophilic repeating unit comprises one or more of a hydrophilic acrylate, a hydrophilic pyrrolidone, or a hydrophilic acrylamide;
wherein the at least one hydrophobic repeating unit comprises a hydrophobic acrylate,
wherein the microparticles form a particulate plug having a hydraulic permeability greater than 0.01 Da,
wherein the particulate plug fits an outlet of a container for a solution, emulsion, or suspension comprising an ionic preservative and a therapeutic agent,
wherein the particulate plug is configured to remove at least 50 percent of the ionic preservative and retain at least 50 percent of the therapeutic agent within the solution, emulsion, or suspension during a time scale to form a drop at the outlet of the container.

2. The preservative removing device of claim 1, further comprising a hydrophilic cross-linker and wherein the hydrophilic cross linker comprises diethylene glycol dimethacrylate (DEGDMA).

3. The preservative removing device of claim 1, further comprising a hydrophobic cross-linker and wherein the hydrophobic cross-linker comprises ethoxylated (15) trimethylolpropane triacrylate or ethylene glycol dimethacrylate (EDGMA).

4. The preservative removing device of claim 1, wherein the at least one hydrophilic repeating unit comprises one or more of hydroxyethyl methacrylate (HEMA), methacrylic acid (MAA), N-vinyl-pyrrolidone (NVP), or dimethylacrylamide (DMA).

5. The preservative removing device of claim 1, wherein the at least one hydrophobic repeating unit comprises one or more of t-butyl methacrylate (TBM) or Methacryloxypropyltris(trimethylsiloxy)silane (TRIS).

6. The preservative removing device of claim 1, wherein the at least one hydrophilic repeating unit comprises HEMA and the at least one hydrophobic repeating unit comprises TBM.

7. The preservative removing device of claim 6, comprising 5% to 25% HEMA and the 75% to 95% TBM.

8. The preservative removing device of claim 1, wherein the at least one hydrophilic repeating unit comprises MAA and the at least one hydrophobic repeating unit comprises TBM.

9. The preservative removing device of claim 8, comprising 5% to 25% MAA and 75% to 95% TBM.

10. The preservative removing device of claim 1, wherein the at least one hydrophilic repeating unit comprises HEMA and the at least one hydrophobic repeating unit comprises TRIS.

11. The preservative removing device of claim 1, wherein the at least one hydrophilic repeating unit comprises DMA and the at least one hydrophobic repeating unit comprises TRIS.

12. The preservative removing device of claim 1, wherein the rigid aggregates are rough edged particles and the rough edged particles comprise a diameter less than 250 microns.

13. The preservative removing device claim 1, wherein the ionic preservative comprises Benzalkonium chloride.

14. The preservative removing device of claim 1, wherein the ionic preservative is a solution of borate, sorbitol, propylene glycol, and zinc or stabilized oxychloro complex.

15. The preservative removing device of claim 1, wherein the therapeutic agent comprises at least one of Timolol Maleate, Levofloxacin, Dorzolamide, Brimonidine Tartrate, Bimatoprost, Tetrahydrozolin, or Olopatadine.

16. The preservative removing device of claim 15, wherein the therapeutic agent comprises Timolol Maleate and Brimonidine Tartrate.

17. The device of claim 1, wherein the particulate plug selectively removes at least 90% of the ionic preservative, while at least 90% of the therapeutic agent is retained in the solution, emulsion, or suspension.

18. The device of claim 17, wherein the preservative removing device is an eye drop bottle for dispensing drops of the solution, emulsion, or suspension and wherein the concentration of the therapeutic agent in a dispensed drop is at least 90% of that of the solution, emulsion, or suspension inside the eye drop bottle, for every drop of the solution, emulsion, or suspension passed through the plug.

19. The preservative removing device of claim 1, wherein the hydrophilic acrylate is hydroxyethyl methacrylate (HEMA) or methacrylic acid (MAA), wherein the hydrophilic pyrrolidone is N-vinyl-pyrrolidone (NVP), and wherein the hydrophilic acrylamide is dimethylacrylamide (DMA).

20. The preservative removing device of claim 1, wherein the hydrophobic acrylate is t-butyl methacrylate (TBM) or Methacryloxypropyltris(trimethylsiloxy)silane (TRIS).

21. A method of removing a preservative from a drug solution, suspension, or emulsion, comprising:
providing a container having an extended outlet and a chamber for holding the drug solution, suspension, or emulsion, the drug solution, suspension, or emulsion comprising at least one drug and an ionic preservative; wherein the container comprises a particulate plug for removing the ionic preservative from the solution, suspension, or emulsion, the particulate plug within the extended outlet; wherein the particulate plug comprises microparticles of a copolymer comprising a least one hydrophilic repeating unit and at least one hydrophobic repeating unit, wherein the microparticles are rigid aggregates; wherein the particulate plug is configured to remove at least 50 percent of the ionic preservative and retain at least 50 percent of the drug within the solution, emulsion, or suspension during a time scale to form a drop at the outlet of the container;
wherein the at least one hydrophilic repeating unit comprises one or more of a hydrophilic acrylate, a hydrophilic pyrrolidone, or a hydrophilic acrylamide;
wherein the at least one hydrophobic repeating unit comprises a hydrophobic acrylate; and
forcing the drug solution, suspension, or emulsion through the particulate plug.

22. A device for delivery of a pharmaceutical formulation, comprising the particulate plug and a pharmaceutical formulation comprising one or more active components and an ionic preservative, wherein the particulate plug comprises microparticles of a copolymer comprising at least one hydrophilic repeating unit and at least one hydrophobic repeating unit, wherein the microparticles are rigid aggregates;
wherein the at least one hydrophilic repeating unit comprises one or more of a hydrophilic acrylate, a hydrophilic pyrrolidone, or a hydrophilic acrylamide;
wherein the at least one hydrophobic repeating unit comprises a hydrophobic acrylate;
wherein when the pharmaceutical formulation is forced through the particulate plug at least 90% of the ionic preservative is selectively removed while at least 90% of all active components are retained in the delivered pharmaceutical formulation.

* * * * *

UNITED STATES PATENT AND TRADEMARK OFFICE
CERTIFICATE OF CORRECTION

PATENT NO. : 11,033,457 B2
APPLICATION NO. : 16/388470
DATED : June 15, 2021
INVENTOR(S) : Anuj Chauhan et al.

Page 1 of 1

It is certified that error appears in the above-identified patent and that said Letters Patent is hereby corrected as shown below:

In the Claims

At Column 81, Line 64, "comprising a least" should be -- comprising at least --.

At Column 82, Line 63, "HEMA and the 75%" should be -- HEMA and 75% --.

At Column 83, Line 14, "The preservative removing device claim" should be -- The preservative removing device of claim --.

At Column 83, Line 22, "Tetrahydrozolin," should be -- Tetrahydrozoline, --.

At Column 83, Line 26, "The device of claim" should be -- The preservative removing device of claim --.

At Column 83, Line 30, "The device of claim" should be -- The preservative removing device of claim --.

At Column 84, Line 11, "comprising a least" should be -- comprising at least --.

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*